(12) United States Patent
Schobel et al.

(10) Patent No.: US 12,023,309 B2
(45) Date of Patent: *Jul. 2, 2024

(54) ENHANCED DELIVERY EPINEPHRINE COMPOSITIONS

(71) Applicant: AQUESTIVE THERAPEUTICS, INC., Warren, NJ (US)

(72) Inventors: Alexander Mark Schobel, Vero Beach, FL (US); Stephanie Marie Varjan, Oradell, NJ (US); Stephen Paul Wargacki, Pittstown, NJ (US)

(73) Assignee: AQUESTIVE THERAPEUTICS, INC., Warren, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/835,442

(22) Filed: Jun. 8, 2022

(65) Prior Publication Data

US 2023/0138361 A1    May 4, 2023

Related U.S. Application Data

(63) Continuation of application No. 17/514,805, filed on Oct. 29, 2021, now abandoned, which is a continuation of application No. 15/587,364, filed on May 4, 2017, now Pat. No. 11,191,737.

(60) Provisional application No. 62/331,996, filed on May 5, 2016.

(51) Int. Cl.
| | |
|---|---|
| *A61K 31/137* | (2006.01) |
| *A61J 1/03* | (2023.01) |
| *A61J 1/05* | (2006.01) |
| *A61J 7/00* | (2006.01) |
| *A61K 9/00* | (2006.01) |
| *A61K 9/70* | (2006.01) |
| *A61K 31/085* | (2006.01) |
| *A61K 36/61* | (2006.01) |
| *A61K 47/10* | (2017.01) |
| *A61K 47/12* | (2006.01) |
| *A61K 47/22* | (2006.01) |
| *A61K 47/38* | (2006.01) |

(52) U.S. Cl.
CPC ............ *A61K 31/137* (2013.01); *A61J 1/03* (2013.01); *A61J 1/05* (2013.01); *A61J 7/0076* (2013.01); *A61K 9/006* (2013.01); *A61K 9/7007* (2013.01); *A61K 31/085* (2013.01); *A61K 36/61* (2013.01); *A61K 47/10* (2013.01); *A61K 47/12* (2013.01); *A61K 47/22* (2013.01); *A61K 47/38* (2013.01)

(58) Field of Classification Search
CPC .... A61K 31/137; A61K 9/7007; A61K 47/10; A61K 47/12; A61K 47/14; A61K 47/32; A61K 47/38; A61K 2300/00

See application file for complete search history.

(56) References Cited

U.S. PATENT DOCUMENTS

| | | |
|---|---|---|
| 26,401 A | 12/1859 | Brashear et al. |
| 307,537 A | 11/1884 | Foulks |
| 476,085 A | 5/1892 | Smith |
| 492,417 A | 2/1893 | McAlister |
| 503,070 A | 8/1893 | Broadwell et al. |
| 596,302 A | 12/1897 | McMahon |
| 688,446 A | 12/1901 | Stempel, Jr. |
| 1,110,546 A | 9/1914 | Hewitt |
| 1,827,354 A | 10/1931 | Cooper |
| 2,142,537 A | 1/1939 | Tiaxa |
| 2,277,038 A | 3/1942 | Curtis |
| 2,352,691 A | 7/1944 | Curtis |
| 2,376,656 A | 5/1945 | Leonia |
| 2,501,544 A | 3/1950 | Shrontz |
| 2,612,165 A | 9/1952 | Szukerski |
| 2,980,554 A | 4/1961 | Gentile et al. |
| 3,007,848 A | 11/1961 | Stroop |
| 3,044,338 A | 7/1962 | Horton et al. |
| 3,131,068 A | 4/1964 | Grief |
| 3,142,217 A | 7/1964 | Busse |
| 3,189,174 A | 6/1965 | Cormack |
| 3,237,596 A | 3/1966 | Grass, Jr. et al. |
| 3,242,959 A | 3/1966 | Glass |
| 3,249,109 A | 5/1966 | Maeth et al. |
| 3,324,754 A | 6/1967 | Peavy |
| 3,370,497 A | 2/1968 | Busse |
| 3,419,137 A | 12/1968 | Walck, III |
| 3,444,858 A | 5/1969 | Russell |
| 3,451,539 A | 6/1969 | Wysocki |
| 3,536,809 A | 10/1970 | Applezwig |
| 3,539,605 A | 11/1970 | Oberhofer |
| 3,551,556 A | 12/1970 | Kliment et al. |
| 3,598,122 A | 8/1971 | Zaffaroni |
| 3,610,248 A | 10/1971 | Davidson |
| 3,625,351 A | 12/1971 | Eisenberg |

(Continued)

FOREIGN PATENT DOCUMENTS

| | | |
|---|---|---|
| AU | 741362 B2 | 11/2001 |
| CA | 2274910 A1 | 6/1998 |

(Continued)

OTHER PUBLICATIONS

PCT/US02/32575, Oct. 11, 2002.
PCT/US02/32594, Oct. 11, 2002.
PCT/US04/17076, May 28, 2004.
PCT/US07/79357, Sep. 25, 2007.
PCT/US11/36244, May 12, 2011.
Bioadhesive Drug Delivery Systems (Lenaerts, V. and Gurny, R. (eds.)), Ch. 6, pp. 106-136 (1990).

(Continued)

*Primary Examiner* — Mina Haghighatian
*Assistant Examiner* — Nathan W Schlientz
(74) *Attorney, Agent, or Firm* — Honigman LLP

(57) ABSTRACT

Pharmaceutical compositions having enhanced active component permeation properties are described.

33 Claims, 22 Drawing Sheets

(56) References Cited

U.S. PATENT DOCUMENTS

| | | |
|---|---|---|
| 3,632,740 A | 1/1972 | Robinson et al. |
| 3,640,741 A | 2/1972 | Etes |
| 3,641,237 A | 2/1972 | Gould et al. |
| 3,650,461 A | 3/1972 | Hutcheson |
| 3,677,866 A | 7/1972 | Pickett et al. |
| 3,731,683 A | 5/1973 | Zaffaroni |
| 3,753,732 A | 8/1973 | Boroshok |
| 3,755,558 A | 8/1973 | Scribner |
| 3,768,725 A | 10/1973 | Pilaro |
| 3,795,527 A | 3/1974 | Stone et al. |
| 3,797,494 A | 3/1974 | Zaffroni |
| 3,809,220 A | 5/1974 | Arcudi |
| 3,809,714 A | 5/1974 | Hussain |
| 3,814,095 A | 6/1974 | Lubens |
| 3,825,014 A | 7/1974 | Wroten |
| 3,835,995 A | 9/1974 | Haines |
| 3,840,657 A | 10/1974 | Norfleet |
| 3,892,905 A | 7/1975 | Albert |
| 3,911,099 A | 10/1975 | DeFoney et al. |
| 3,933,245 A | 1/1976 | Mullen |
| 3,972,995 A | 8/1976 | Tsuk et al. |
| 3,979,839 A | 9/1976 | Blanie |
| 3,996,934 A | 12/1976 | Zaffaroni |
| 3,998,215 A | 12/1976 | Anderson et al. |
| 4,015,023 A | 3/1977 | Lamberti et al. |
| 4,022,924 A | 5/1977 | Mitchell et al. |
| 4,029,757 A | 6/1977 | Mlodozeniec et al. |
| 4,029,758 A | 6/1977 | Mlodozeniec et al. |
| 4,031,200 A | 6/1977 | Reif |
| 4,049,848 A | 9/1977 | Goodale et al. |
| 4,053,046 A | 10/1977 | Roark |
| 4,067,116 A | 1/1978 | Bryner et al. |
| 4,105,116 A | 8/1978 | Jones et al. |
| 4,123,592 A | 10/1978 | Rainer et al. |
| 4,126,503 A | 11/1978 | Gardner |
| 4,128,445 A | 12/1978 | Sturzenegger et al. |
| 4,136,145 A | 1/1979 | Fuchs et al. |
| 4,136,162 A | 1/1979 | Fuchs et al. |
| 4,139,627 A | 2/1979 | Lane et al. |
| 4,145,441 A | 3/1979 | Bodor |
| 4,202,966 A | 5/1980 | Misaki et al. |
| 4,226,848 A | 10/1980 | Nagai et al. |
| 4,249,531 A | 2/1981 | Heller et al. |
| 4,251,400 A | 2/1981 | Columbus |
| 4,251,561 A | 2/1981 | Gajewski |
| 4,284,194 A | 8/1981 | Flatau |
| 4,284,534 A | 8/1981 | Ehrlich |
| 4,292,299 A | 9/1981 | Suzuki et al. |
| 4,294,820 A | 10/1981 | Keith et al. |
| 4,302,465 A | 11/1981 | AF Ekenstam et al. |
| 4,307,075 A | 12/1981 | Martin |
| 4,307,117 A | 12/1981 | Leshik |
| 4,325,855 A | 4/1982 | Dickmann et al. |
| 4,341,563 A | 7/1982 | Kurihara et al. |
| 4,365,423 A | 12/1982 | Arter et al. |
| 4,373,036 A | 2/1983 | Chang et al. |
| 4,390,450 A | 6/1983 | Gibson et al. |
| 4,406,708 A | 9/1983 | Hesselgren |
| 4,432,975 A | 2/1984 | Libby |
| 4,438,258 A | 3/1984 | Graham |
| 4,451,260 A | 5/1984 | Mitra |
| 4,460,532 A | 7/1984 | Cornell |
| 4,460,562 A | 7/1984 | Keith et al. |
| 4,466,973 A | 8/1984 | Rennie |
| 4,478,658 A | 10/1984 | Wittwer |
| 4,483,846 A | 11/1984 | Koide et al. |
| 4,503,070 A | 3/1985 | Eby, III |
| 4,511,592 A | 4/1985 | Percel et al. |
| 4,515,162 A | 5/1985 | Yamamoto et al. |
| 4,517,173 A | 5/1985 | Kizawa et al. |
| 4,529,301 A | 7/1985 | Rountree |
| 4,529,601 A | 7/1985 | Broberg et al. |
| 4,529,748 A | 7/1985 | Wienecke |
| 4,562,020 A | 12/1985 | Hijiya et al. |
| 4,568,535 A | 2/1986 | Loesche |
| 4,569,837 A | 2/1986 | Suzuki et al. |
| 4,572,832 A | 2/1986 | Kigasawa et al. |
| 4,582,835 A | 4/1986 | Lewis et al. |
| 4,585,452 A | 4/1986 | Sablotsky |
| 4,588,592 A | 5/1986 | Elias |
| 4,593,053 A | 6/1986 | Jevne et al. |
| 4,598,089 A | 7/1986 | Hadvary et al. |
| 4,608,249 A | 8/1986 | Otsuka et al. |
| 4,613,497 A | 9/1986 | Chavkin |
| 4,615,697 A | 10/1986 | Robinson |
| 4,619,701 A | 10/1986 | Angrick et al. |
| 4,621,482 A | 11/1986 | Crevasse et al. |
| 4,623,394 A | 11/1986 | Nakamura et al. |
| 4,631,837 A | 12/1986 | Magoon |
| 4,639,367 A | 1/1987 | Mackles |
| 4,648,509 A | 3/1987 | Alves |
| 4,659,714 A | 4/1987 | Watt-Smith |
| 4,661,359 A | 4/1987 | Seaborne et al. |
| 4,675,009 A | 6/1987 | Hymes et al. |
| 4,695,465 A | 9/1987 | Kigasawa et al. |
| 4,704,119 A | 11/1987 | Shaw et al. |
| 4,705,174 A | 11/1987 | Goglio |
| 4,712,460 A | 12/1987 | Allen et al. |
| 4,713,239 A | 12/1987 | Babaian et al. |
| 4,713,243 A | 12/1987 | Schiraldi et al. |
| 4,713,251 A | 12/1987 | Seighman |
| 4,716,802 A | 1/1988 | O'Connor et al. |
| 4,722,761 A | 2/1988 | Cartmell et al. |
| 4,727,064 A | 2/1988 | Pitha |
| 4,740,365 A | 4/1988 | Yukimatsu et al. |
| 4,748,022 A | 5/1988 | Busciglio |
| 4,752,465 A | 6/1988 | Mackles |
| 4,762,230 A | 8/1988 | Croce |
| 4,764,378 A | 8/1988 | Keith et al. |
| 4,765,983 A | 8/1988 | Takayanagi et al. |
| 4,772,470 A | 9/1988 | Inoue et al. |
| 4,777,046 A | 10/1988 | Iwakura et al. |
| 4,780,309 A | 10/1988 | Geria et al. |
| 4,781,294 A | 11/1988 | Croce |
| 4,787,517 A | 11/1988 | Martin |
| 4,789,667 A | 12/1988 | Makino et al. |
| 4,802,924 A | 2/1989 | Woznicki et al. |
| 4,828,841 A | 5/1989 | Porter et al. |
| 4,849,246 A | 7/1989 | Schmidt |
| 4,851,394 A | 7/1989 | Kubodera |
| 4,860,754 A | 8/1989 | Sharik et al. |
| 4,861,632 A | 8/1989 | Caggiano |
| RE33,093 E | 10/1989 | Schiraldi et al. |
| 4,872,270 A | 10/1989 | Fronheiser et al. |
| 4,876,092 A | 10/1989 | Mizobuchi et al. |
| 4,876,970 A | 10/1989 | Bolduc |
| 4,880,416 A | 11/1989 | Horiuchi et al. |
| 4,888,354 A | 12/1989 | Chang et al. |
| 4,894,232 A | 1/1990 | Reul et al. |
| 4,900,552 A | 2/1990 | Sanvordeker et al. |
| 4,900,554 A | 2/1990 | Yangibashi et al. |
| 4,900,556 A | 2/1990 | Wheatley et al. |
| 4,910,247 A | 3/1990 | Haidar et al. |
| 4,915,950 A | 4/1990 | Miranda et al. |
| 4,925,670 A | 5/1990 | Schmidt |
| 4,927,634 A | 5/1990 | Sorrentino et al. |
| 4,927,636 A | 5/1990 | Hijiya et al. |
| 4,929,447 A | 5/1990 | Yang |
| 4,937,078 A | 6/1990 | Mezei et al. |
| 4,940,587 A | 7/1990 | Jenkins et al. |
| 4,948,580 A | 8/1990 | Browning |
| 4,958,580 A | 9/1990 | Asaba et al. |
| 4,978,531 A | 12/1990 | Yamazaki et al. |
| 4,980,169 A | 12/1990 | Oppenheimer et al. |
| 4,981,693 A | 1/1991 | Higashi et al. |
| 4,981,875 A | 1/1991 | Leusner et al. |
| 4,993,586 A | 2/1991 | Taulbee et al. |
| 5,023,082 A | 6/1991 | Friedman et al. |
| 5,023,271 A | 6/1991 | Vigne et al. |
| 5,024,701 A | 6/1991 | Desmarais |
| 5,025,692 A | 6/1991 | Reynolds |
| 5,028,632 A | 7/1991 | Fuisz |
| 5,044,241 A | 9/1991 | Labrecque |
| 5,044,761 A | 9/1991 | Yuhki et al. |

(56) References Cited

U.S. PATENT DOCUMENTS

| | | |
|---|---|---|
| 5,045,445 A | 9/1991 | Schultz |
| 5,047,244 A | 9/1991 | Sanvordeker et al. |
| 5,049,322 A | 9/1991 | Devissaguet et al. |
| 5,056,584 A | 10/1991 | Seaton |
| 5,064,717 A | 11/1991 | Suzuki et al. |
| 5,072,842 A | 12/1991 | White |
| 5,078,734 A | 1/1992 | Noble |
| 5,089,307 A | 2/1992 | Ninomiya et al. |
| 5,100,591 A | 3/1992 | Leclef et al. |
| 5,107,734 A | 4/1992 | Armbruster |
| 5,116,140 A | 5/1992 | Hirashima |
| 5,118,508 A | 6/1992 | Kikuchi et al. |
| 5,126,160 A | 6/1992 | Giddey et al. |
| 5,137,729 A | 8/1992 | Kuroya et al. |
| 5,158,825 A | 10/1992 | Altwirth |
| 5,166,233 A | 11/1992 | Kuroya et al. |
| 5,176,705 A | 1/1993 | Noble |
| 5,184,771 A | 2/1993 | Jud et al. |
| 5,186,938 A | 2/1993 | Sablotsky et al. |
| 5,188,838 A | 2/1993 | Deleuil et al. |
| 5,196,436 A | 3/1993 | Smith |
| 5,229,164 A | 7/1993 | Pins et al. |
| 5,230,441 A | 7/1993 | Kaufman et al. |
| 5,234,957 A | 8/1993 | Mantelle |
| 5,264,024 A | 11/1993 | Bosvot et al. |
| 5,271,940 A | 12/1993 | Cleary et al. |
| 5,272,191 A | 12/1993 | Ibrahim et al. |
| 5,273,758 A | 12/1993 | Royce |
| 5,293,699 A | 3/1994 | Faust et al. |
| 5,316,717 A | 5/1994 | Koepff et al. |
| 5,325,968 A | 7/1994 | Sowden |
| 5,328,942 A | 7/1994 | Akhtar et al. |
| 5,344,676 A | 9/1994 | Kim et al. |
| 5,346,701 A | 9/1994 | Heiber et al. |
| 5,354,551 A | 10/1994 | Schmidt |
| 5,360,629 A | 11/1994 | Milbourn et al. |
| 5,369,131 A | 11/1994 | Poli et al. |
| 5,375,930 A | 12/1994 | Tani |
| 5,380,529 A | 1/1995 | Heusser et al. |
| 5,393,528 A | 2/1995 | Staab |
| 5,405,637 A | 4/1995 | Martinez et al. |
| 5,407,278 A | 4/1995 | Beer |
| 5,411,945 A | 5/1995 | Ozaki et al. |
| 5,413,792 A | 5/1995 | Ninomiya et al. |
| 5,422,127 A | 6/1995 | Dube et al. |
| 5,423,423 A | 6/1995 | Sato et al. |
| 5,433,960 A | 7/1995 | Meyers |
| 5,451,419 A | 9/1995 | Schwab et al. |
| 5,455,043 A | 10/1995 | Fischel-Ghodsian |
| 5,458,884 A | 10/1995 | Britton et al. |
| 5,462,749 A | 10/1995 | Rencher |
| 5,472,704 A | 12/1995 | Santus et al. |
| 5,479,408 A | 12/1995 | Will |
| 5,489,436 A | 2/1996 | Hoy et al. |
| 5,506,046 A | 4/1996 | Andersen et al. |
| 5,506,049 A | 4/1996 | Swei et al. |
| 5,518,902 A | 5/1996 | Ozaki et al. |
| 5,529,782 A | 6/1996 | Staab |
| 5,530,861 A | 6/1996 | Diamant et al. |
| 5,550,178 A | 8/1996 | Desai et al. |
| 5,551,033 A | 8/1996 | Foster et al. |
| 5,552,152 A | 9/1996 | Shen |
| 5,553,835 A | 9/1996 | Dresie et al. |
| 5,560,538 A | 10/1996 | Sato et al. |
| 5,567,237 A | 10/1996 | Kapp-Schwerer et al. |
| 5,567,431 A | 10/1996 | Vert et al. |
| 5,573,783 A | 11/1996 | Desieno et al. |
| 5,582,342 A | 12/1996 | Jud |
| 5,587,175 A | 12/1996 | Viegas et al. |
| 5,588,009 A | 12/1996 | Will |
| 5,589,357 A | 12/1996 | Martinez et al. |
| 5,593,697 A | 1/1997 | Barr et al. |
| 5,595,980 A | 1/1997 | Brode et al. |
| 5,601,605 A | 2/1997 | Crowe et al. |
| 5,605,696 A | 2/1997 | Eury et al. |
| 5,605,698 A | 2/1997 | Ueno |
| 5,613,779 A | 3/1997 | Niwa |
| 5,614,212 A | 3/1997 | D'Angelo et al. |
| 5,620,757 A | 4/1997 | Ninomiya et al. |
| 5,629,003 A | 5/1997 | Horstmann et al. |
| 5,629,021 A | 5/1997 | Wright |
| 5,633,006 A | 5/1997 | Catania et al. |
| 5,641,093 A | 6/1997 | Dolin et al. |
| 5,641,536 A | 6/1997 | Lech et al. |
| D380,836 S | 7/1997 | Fitzpatrick et al. |
| 5,647,431 A | 7/1997 | Takeshita et al. |
| 5,653,993 A | 8/1997 | Ghanta et al. |
| 5,656,296 A | 8/1997 | Khan et al. |
| 5,656,297 A | 8/1997 | Bernstein et al. |
| 5,670,168 A | 9/1997 | Baichwal et al. |
| 5,679,145 A | 10/1997 | Andersen et al. |
| 5,681,873 A | 10/1997 | Norton et al. |
| 5,689,550 A | 11/1997 | Garson et al. |
| 5,698,181 A | 12/1997 | Luo |
| 5,698,217 A | 12/1997 | Wilking |
| 5,700,478 A | 12/1997 | Biegajski et al. |
| 5,700,479 A | 12/1997 | Lundgren |
| 5,725,648 A | 3/1998 | Brown et al. |
| 5,733,575 A | 3/1998 | Mehra et al. |
| 5,738,211 A | 4/1998 | Ichino et al. |
| 5,742,905 A | 4/1998 | Pepe et al. |
| 5,750,145 A | 5/1998 | Patell |
| 5,750,157 A | 5/1998 | Grosswald et al. |
| 5,750,585 A | 5/1998 | Park et al. |
| 5,759,599 A | 6/1998 | Wampler et al. |
| 5,761,525 A | 6/1998 | Williams |
| 5,764,639 A | 6/1998 | Staples et al. |
| 5,764,899 A | 6/1998 | Eggleston et al. |
| 5,765,004 A | 6/1998 | Foster et al. |
| 5,766,332 A | 6/1998 | Graves et al. |
| 5,766,525 A | 6/1998 | Andersen et al. |
| 5,766,620 A | 6/1998 | Heiber et al. |
| 5,766,839 A | 6/1998 | Johnson et al. |
| 5,771,353 A | 6/1998 | Eggleston et al. |
| 5,785,180 A | 7/1998 | Dressel et al. |
| 5,792,494 A | 8/1998 | Kanca et al. |
| 5,800,832 A | 9/1998 | Tapolsky et al. |
| 5,806,284 A | 9/1998 | Gifford |
| 5,815,398 A | 9/1998 | Dighe et al. |
| 5,822,526 A | 10/1998 | Waskiewicz |
| 5,830,437 A | 11/1998 | Ascione et al. |
| 5,830,884 A | 11/1998 | Kasica et al. |
| 5,846,557 A | 12/1998 | Eisenstadt et al. |
| 5,847,023 A | 12/1998 | Viegas et al. |
| 5,862,915 A | 1/1999 | Plezia et al. |
| 5,864,684 A | 1/1999 | Nielsen |
| 5,879,690 A | 3/1999 | Perricone |
| 5,881,476 A | 3/1999 | Strobush et al. |
| 5,891,461 A | 4/1999 | Jona et al. |
| 5,891,845 A | 4/1999 | Myers |
| 5,894,930 A | 4/1999 | Faughey et al. |
| 5,900,247 A | 5/1999 | Rault et al. |
| 5,906,742 A | 5/1999 | Wang et al. |
| 5,930,914 A | 8/1999 | Johansson et al. |
| 5,937,161 A | 8/1999 | Mulligan et al. |
| 5,941,393 A | 8/1999 | Wilfong, Jr. |
| 5,945,651 A | 8/1999 | Chorosinski et al. |
| 5,948,430 A | 9/1999 | Zerbe et al. |
| 5,955,097 A | 9/1999 | Tapolsky et al. |
| 5,965,154 A | 10/1999 | Haralambopoulos |
| 5,980,554 A | 11/1999 | Lenker et al. |
| 5,992,742 A | 11/1999 | Sullivan et al. |
| 5,995,597 A | 11/1999 | Woltz et al. |
| 6,004,996 A | 12/1999 | Shah et al. |
| 6,024,975 A | 2/2000 | D'Angelo et al. |
| 6,028,066 A | 2/2000 | Unger |
| 6,030,616 A | 2/2000 | Waters et al. |
| 6,031,895 A | 2/2000 | Cohn et al. |
| 6,036,016 A | 3/2000 | Arnold |
| 6,047,484 A | 4/2000 | Bolland et al. |
| 6,051,253 A | 4/2000 | Zettler et al. |
| 6,054,119 A | 4/2000 | Hurme et al. |
| 6,064,990 A | 5/2000 | Goldsmith |
| 6,072,100 A | 6/2000 | Mooney et al. |

(56) References Cited

U.S. PATENT DOCUMENTS

| | | |
|---|---|---|
| 6,074,097 A | 6/2000 | Hayashi et al. |
| 6,077,558 A | 6/2000 | Euber |
| 6,090,401 A | 7/2000 | Gowan, Jr. et al. |
| 6,099,871 A | 8/2000 | Martinez |
| 6,103,266 A | 8/2000 | Tapolsky et al. |
| 6,106,930 A | 8/2000 | Ludwig |
| 6,143,276 A | 11/2000 | Unger |
| 6,148,708 A | 11/2000 | Pfeiffer |
| 6,152,007 A | 11/2000 | Sato |
| 6,153,210 A | 11/2000 | Roberts et al. |
| 6,153,220 A | 11/2000 | Cumming et al. |
| 6,159,498 A | 12/2000 | Tapolsky et al. |
| 6,161,129 A | 12/2000 | Rochkind |
| 6,177,066 B1 | 1/2001 | Pataut et al. |
| 6,177,092 B1 | 1/2001 | Lentini et al. |
| 6,177,096 B1 | 1/2001 | Zerbe et al. |
| 6,183,808 B1 | 2/2001 | Grillo et al. |
| 6,197,329 B1 | 3/2001 | Hermelin et al. |
| 6,203,566 B1 | 3/2001 | Alanen et al. |
| 6,219,694 B1 | 4/2001 | Lazaridis et al. |
| 6,221,402 B1 | 4/2001 | Itoh et al. |
| 6,227,359 B1 | 5/2001 | Truluck |
| 6,230,894 B1 | 5/2001 | Danville |
| 6,231,957 B1 | 5/2001 | Zerbe et al. |
| 6,238,700 B1 | 5/2001 | Dohner et al. |
| 6,264,981 B1 | 7/2001 | Zhang et al. |
| 6,267,808 B1 | 7/2001 | Grillo et al. |
| 6,268,048 B1 | 7/2001 | Karaev et al. |
| 6,284,264 B1 | 9/2001 | Zerbe et al. |
| 6,287,595 B1 | 9/2001 | Loewy et al. |
| 6,294,206 B1 | 9/2001 | Barrett-Reis et al. |
| 6,311,627 B1 | 11/2001 | Draper et al. |
| 6,338,407 B2 | 1/2002 | Danville |
| 6,344,088 B1 | 2/2002 | Kamikihara et al. |
| 6,374,715 B1 | 4/2002 | Takatsuka |
| 6,375,963 B1 | 4/2002 | Repka et al. |
| 6,391,294 B1 | 5/2002 | Dettmar et al. |
| 6,394,306 B1 | 5/2002 | Pawlo et al. |
| 6,395,299 B1 | 5/2002 | Babich et al. |
| 6,413,792 B1 | 7/2002 | Sauer et al. |
| 6,419,903 B1 | 7/2002 | Xu et al. |
| 6,419,906 B1 | 7/2002 | Xu et al. |
| 6,428,825 B2 | 8/2002 | Sharma et al. |
| 6,432,460 B1 | 8/2002 | Zietlow et al. |
| 6,436,464 B1 | 8/2002 | Euber |
| 6,454,788 B1 | 9/2002 | Ashton |
| 6,467,621 B1 | 10/2002 | Ishida |
| 6,468,516 B1 | 10/2002 | Geria et al. |
| 6,472,003 B2 | 10/2002 | Barrett-Reis et al. |
| 6,482,517 B1 | 11/2002 | Anderson |
| 6,488,963 B1 | 12/2002 | McGinity et al. |
| 6,495,599 B2 | 12/2002 | Auestad et al. |
| 6,503,532 B1 | 1/2003 | Murty et al. |
| 6,509,072 B2 | 1/2003 | Bening et al. |
| 6,534,090 B2 | 3/2003 | Puthli et al. |
| 6,534,092 B2 | 3/2003 | Wright |
| 6,552,024 B1 | 4/2003 | Chen et al. |
| 6,562,375 B1 | 5/2003 | Sako et al. |
| 6,575,999 B1 | 6/2003 | Rohrig |
| 6,589,576 B2 | 7/2003 | Borschel et al. |
| 6,592,887 B2 | 7/2003 | Zerbe et al. |
| 6,596,298 B2 | 7/2003 | Leung et al. |
| 6,596,302 B2 | 7/2003 | O'Connor et al. |
| 6,599,542 B1 | 7/2003 | Abdel-Malik et al. |
| 6,610,338 B2 | 8/2003 | Tang |
| 6,620,440 B1 | 9/2003 | Hsia et al. |
| 6,655,112 B1 | 12/2003 | Cremer et al. |
| 6,656,493 B2 | 12/2003 | Dzija et al. |
| 6,660,292 B2 | 12/2003 | Zerbe et al. |
| 6,667,060 B1 | 12/2003 | Vandecruys et al. |
| 6,668,839 B2 | 12/2003 | Williams |
| 6,708,826 B1 | 3/2004 | Ginsberg et al. |
| 6,709,671 B2 | 3/2004 | Zerbe et al. |
| 6,720,006 B2 | 4/2004 | Hanke et al. |
| 6,726,054 B2 | 4/2004 | Fagen et al. |
| 6,730,319 B2 | 5/2004 | Maeder et al. |
| 6,752,824 B2 | 6/2004 | Yancy |
| 6,776,157 B2 | 8/2004 | Williams et al. |
| 6,797,283 B1 | 9/2004 | Edgren et al. |
| 6,800,329 B2 | 10/2004 | Horstmann et al. |
| 6,824,829 B2 | 11/2004 | Berry et al. |
| 6,865,860 B2 | 3/2005 | Arakawa et al. |
| 6,905,016 B2 | 6/2005 | Kanios et al. |
| 6,913,766 B1 | 7/2005 | Krumme et al. |
| 6,929,399 B2 | 8/2005 | Nokura |
| 6,929,400 B2 | 8/2005 | Razeti et al. |
| 7,005,142 B2 | 2/2006 | Leon et al. |
| 7,040,503 B2 | 5/2006 | Leichter et al. |
| 7,067,116 B1 | 6/2006 | Bess et al. |
| 7,093,736 B2 | 8/2006 | Maietta et al. |
| 7,115,507 B2 | 10/2006 | Kawase |
| 7,179,788 B2 | 2/2007 | DeFelippis et al. |
| 7,241,411 B2 | 7/2007 | Berry et al. |
| 7,357,891 B2 | 4/2008 | Yang et al. |
| 7,390,503 B1 | 6/2008 | Ahmed et al. |
| 7,425,292 B2 | 9/2008 | Yang et al. |
| 7,428,859 B2 | 9/2008 | Fujita et al. |
| 7,484,640 B2 | 2/2009 | von Falkenhausen et al. |
| 7,531,191 B2 | 5/2009 | Zion et al. |
| 7,579,019 B2 | 8/2009 | Tapolsky et al. |
| 7,591,801 B2 | 9/2009 | Brauker et al. |
| 7,665,896 B1 | 2/2010 | Higgs |
| 7,666,337 B2 | 2/2010 | Yang et al. |
| 7,694,617 B2 | 4/2010 | Habra et al. |
| 7,766,013 B2 | 8/2010 | Wensley |
| 7,824,588 B2 | 11/2010 | Yang et al. |
| 7,910,031 B2 | 3/2011 | Yang et al. |
| 8,017,150 B2 | 9/2011 | Yang et al. |
| 8,051,983 B2 | 11/2011 | Simon et al. |
| 8,147,866 B2 | 4/2012 | Finn et al. |
| 8,617,589 B2 * | 12/2013 | Fuisz ............... A61K 9/7007 424/443 |
| 8,840,935 B2 | 9/2014 | Haber |
| 8,936,825 B2 | 1/2015 | Myers et al. |
| 9,125,836 B2 | 9/2015 | Nagaso et al. |
| 10,149,810 B2 | 12/2018 | Perusse et al. |
| 10,806,709 B2 | 10/2020 | Fleming |
| 11,021,437 B2 | 6/2021 | Almoazen |
| 11,191,737 B2 * | 12/2021 | Schobel ............... A61P 25/02 |
| 2001/0006677 A1 | 7/2001 | McGinity et al. |
| 2001/0022964 A1 | 9/2001 | Leung et al. |
| 2001/0046511 A1 | 11/2001 | Zerbe et al. |
| 2002/0006677 A1 | 1/2002 | Egermeier et al. |
| 2002/0012689 A1 | 1/2002 | Stillman |
| 2002/0045582 A1 | 4/2002 | Margolin et al. |
| 2002/0098198 A1 | 7/2002 | Watts et al. |
| 2002/0104774 A1 | 8/2002 | Hammond |
| 2002/0127254 A1 | 9/2002 | Fotinos et al. |
| 2002/0131990 A1 | 9/2002 | Barkalow et al. |
| 2002/0147201 A1 | 10/2002 | Chen et al. |
| 2002/0170567 A1 | 11/2002 | Rizzotto et al. |
| 2002/0177380 A1 | 11/2002 | Forman et al. |
| 2003/0035841 A1 | 2/2003 | Dzija et al. |
| 2003/0044446 A1 | 3/2003 | Moro et al. |
| 2003/0044511 A1 | 3/2003 | Zerbe et al. |
| 2003/0054039 A1 | 3/2003 | Zyck et al. |
| 2003/0068378 A1 | 4/2003 | Chen et al. |
| 2003/0069263 A1 | 4/2003 | Breder et al. |
| 2003/0072865 A1 | 4/2003 | Bindels et al. |
| 2003/0077315 A1 | 4/2003 | Lee et al. |
| 2003/0107149 A1 | 6/2003 | Yang et al. |
| 2003/0118649 A1 | 6/2003 | Gao et al. |
| 2003/0121932 A1 | 7/2003 | Wajda |
| 2003/0124176 A1 | 7/2003 | Hsu et al. |
| 2003/0140760 A1 | 7/2003 | Bory |
| 2003/0143195 A1 | 7/2003 | Pinsker |
| 2003/0147956 A1 | 8/2003 | Shefer et al. |
| 2003/0161926 A1 | 8/2003 | Kemp et al. |
| 2003/0183643 A1 | 10/2003 | Fagen et al. |
| 2003/0224044 A1 | 12/2003 | Weibel |
| 2004/0013731 A1 | 1/2004 | Chen et al. |
| 2004/0024003 A1 | 2/2004 | Asmussen et al. |
| 2004/0044367 A1 | 3/2004 | Yancy |
| 2004/0058457 A1 | 3/2004 | Huang et al. |

(56) References Cited

U.S. PATENT DOCUMENTS

| | | |
|---|---|---|
| 2004/0091677 A1 | 5/2004 | Topolkaraev |
| 2004/0096569 A1 | 5/2004 | Barkalow et al. |
| 2004/0102867 A1 | 5/2004 | Palanisamy et al. |
| 2004/0111275 A1 | 6/2004 | Kroll et al. |
| 2004/0120991 A1 | 6/2004 | Gardner et al. |
| 2004/0136924 A1 | 7/2004 | Boyd et al. |
| 2004/0137458 A1 | 7/2004 | Archambault et al. |
| 2004/0156901 A1 | 8/2004 | Thakur et al. |
| 2004/0191302 A1 | 9/2004 | Davidson |
| 2004/0209057 A1 | 10/2004 | Enlow et al. |
| 2004/0219109 A1 | 11/2004 | Hatch |
| 2004/0241242 A1 | 12/2004 | Fuisz et al. |
| 2004/0265353 A1 | 12/2004 | Zhang et al. |
| 2005/0003048 A1 | 1/2005 | Pearce et al. |
| 2005/0011776 A1 | 1/2005 | Nagel |
| 2005/0019588 A1 | 1/2005 | Berry et al. |
| 2005/0035133 A1 | 2/2005 | Gerulski et al. |
| 2005/0037055 A1 | 2/2005 | Yang et al. |
| 2005/0042271 A1 | 2/2005 | Xiong |
| 2005/0048102 A1 | 3/2005 | Tapolsky et al. |
| 2005/0055123 A1 | 3/2005 | Franz |
| 2005/0089548 A1 | 4/2005 | Virgalitto et al. |
| 2005/0095272 A1 | 5/2005 | Augello |
| 2005/0115862 A1 | 6/2005 | Maietta |
| 2005/0118217 A1 | 6/2005 | Barnhart et al. |
| 2005/0118271 A1 | 6/2005 | Schliecker et al. |
| 2005/0136115 A1 | 6/2005 | Kulkarni et al. |
| 2005/0147653 A1 | 7/2005 | Yasuda et al. |
| 2005/0147658 A1 | 7/2005 | Tapolsky et al. |
| 2005/0163714 A1 | 7/2005 | Sukhishvili et al. |
| 2005/0170138 A1 | 8/2005 | Berry |
| 2005/0191349 A1 | 9/2005 | Boehm et al. |
| 2005/0192309 A1 | 9/2005 | Palermo et al. |
| 2005/0214251 A1 | 9/2005 | Pohl et al. |
| 2005/0222781 A1 | 10/2005 | Yue et al. |
| 2005/0232977 A1 | 10/2005 | Khan et al. |
| 2005/0239845 A1 | 10/2005 | Proehl et al. |
| 2005/0266085 A1 | 12/2005 | Warner |
| 2006/0023976 A1 | 2/2006 | Alvater et al. |
| 2006/0039958 A1 | 2/2006 | Fuisz et al. |
| 2006/0071057 A1 | 4/2006 | Aschenbrenner et al. |
| 2006/0073173 A1 | 4/2006 | Banach et al. |
| 2006/0073190 A1 | 4/2006 | Carroll et al. |
| 2006/0083786 A1 | 4/2006 | Chaudhari et al. |
| 2006/0093679 A1 | 5/2006 | Mayer et al. |
| 2006/0104910 A1 | 5/2006 | Lerner |
| 2006/0134200 A1 | 6/2006 | Vandoni |
| 2006/0147493 A1 | 7/2006 | Yang et al. |
| 2006/0163269 A1 | 7/2006 | Anderson et al. |
| 2006/0180604 A1 | 8/2006 | Ginsberg et al. |
| 2006/0182796 A1 | 8/2006 | Wu et al. |
| 2006/0189772 A1 | 8/2006 | Scheibel et al. |
| 2006/0198790 A1 | 9/2006 | Dugger, III et al. |
| 2006/0198885 A1 | 9/2006 | Dharmadhikari et al. |
| 2006/0210610 A1 | 9/2006 | Davidson et al. |
| 2006/0213348 A1 | 9/2006 | Loibl |
| 2006/0215941 A1 | 9/2006 | Golbert |
| 2006/0246141 A1 | 11/2006 | Liversidge et al. |
| 2006/0264448 A1 | 11/2006 | Pryde |
| 2006/0281775 A1 | 12/2006 | Kelly, II et al. |
| 2006/0286108 A1 | 12/2006 | Bell |
| 2007/0027213 A1 | 2/2007 | Oberegger et al. |
| 2007/0045148 A1 | 3/2007 | Saclier et al. |
| 2007/0069416 A1 | 3/2007 | Yang et al. |
| 2007/0071806 A1 | 3/2007 | McCarty et al. |
| 2007/0087036 A1 | 4/2007 | Durschlag et al. |
| 2007/0098746 A1 | 5/2007 | Nichols et al. |
| 2007/0122455 A1 | 5/2007 | Myers et al. |
| 2007/0138049 A1 | 6/2007 | Bitner |
| 2007/0148097 A1 | 6/2007 | Finn et al. |
| 2007/0170196 A1 | 7/2007 | Libohova et al. |
| 2007/0202163 A1 | 8/2007 | Rawas-Qalaji |
| 2007/0205127 A1 | 9/2007 | Barndt et al. |
| 2007/0231368 A1 | 10/2007 | Wang et al. |
| 2007/0267433 A1 | 11/2007 | Fuisz et al. |
| 2007/0275893 A1 | 11/2007 | Quay |
| 2007/0281003 A1 | 12/2007 | Fuisz et al. |
| 2007/0293581 A1* | 12/2007 | Hill ............................ A61P 37/08 514/649 |
| 2007/0293582 A1 | 12/2007 | Hill |
| 2008/0044454 A1 | 2/2008 | Yang et al. |
| 2008/0073235 A1 | 3/2008 | Harada et al. |
| 2008/0075825 A1 | 3/2008 | Fuisz et al. |
| 2008/0081071 A1 | 4/2008 | Sanghvi et al. |
| 2008/0105582 A1 | 5/2008 | Ludwig et al. |
| 2008/0233174 A1 | 9/2008 | Myers et al. |
| 2008/0242558 A1 | 10/2008 | Belcher et al. |
| 2008/0242736 A1 | 10/2008 | Fuisz |
| 2008/0254105 A1 | 10/2008 | Tapolsky et al. |
| 2008/0260805 A1 | 10/2008 | Yang et al. |
| 2008/0260809 A1 | 10/2008 | Yang et al. |
| 2008/0268116 A1 | 10/2008 | Kring |
| 2008/0290106 A1 | 11/2008 | van der Klaauw et al. |
| 2008/0299197 A1 | 12/2008 | Tongeguzzo et al. |
| 2008/0300173 A1 | 12/2008 | DeFrees |
| 2008/0308449 A1 | 12/2008 | Intini |
| 2009/0004254 A1 | 1/2009 | Maibach |
| 2009/0009332 A1 | 1/2009 | Nunez et al. |
| 2009/0014491 A1 | 1/2009 | Fuisz et al. |
| 2009/0029074 A1 | 1/2009 | Sasine et al. |
| 2009/0074333 A1 | 3/2009 | Griebel et al. |
| 2009/0104270 A1 | 4/2009 | Myers et al. |
| 2009/0146336 A1 | 6/2009 | Masi |
| 2009/0181075 A1 | 7/2009 | Gordon et al. |
| 2009/0186107 A1 | 7/2009 | Haber et al. |
| 2009/0192075 A1 | 7/2009 | Steiner |
| 2009/0196907 A1 | 8/2009 | Bunick et al. |
| 2009/0280160 A1 | 11/2009 | Monteith et al. |
| 2009/0297614 A1 | 12/2009 | Rademacher et al. |
| 2010/0015128 A1 | 1/2010 | Lee et al. |
| 2010/0087470 A1 | 4/2010 | Oksche et al. |
| 2010/0092545 A1 | 4/2010 | Yang et al. |
| 2010/0150986 A1 | 6/2010 | Nagaso et al. |
| 2010/0178254 A1 | 7/2010 | Hariharan et al. |
| 2010/0221309 A1 | 9/2010 | Myers et al. |
| 2010/0297232 A1 | 11/2010 | Myers et al. |
| 2011/0189259 A1 | 8/2011 | Vasisht et al. |
| 2011/0192863 A1 | 8/2011 | Barrass et al. |
| 2011/0257096 A1 | 10/2011 | Maggio |
| 2011/0262520 A1 | 10/2011 | Dormady et al. |
| 2011/0262522 A1 | 10/2011 | Finn et al. |
| 2012/0009260 A1* | 1/2012 | Schobel ................. A61K 9/006 514/12.3 |
| 2012/0058158 A1* | 3/2012 | Booles .................... A61P 25/04 514/783 |
| 2013/0085105 A1 | 4/2013 | Deasy et al. |
| 2013/0267585 A1 | 10/2013 | Ljusberg-Wahren |
| 2013/0337022 A1 | 12/2013 | Pillay et al. |
| 2014/0128379 A1 | 5/2014 | Bergenhem et al. |
| 2014/0316333 A1 | 10/2014 | Kwon |
| 2015/0038540 A1 | 2/2015 | Zerbe |
| 2015/0202148 A1 | 7/2015 | Cifter |
| 2016/0051494 A1 | 2/2016 | Gulfo |
| 2017/0087077 A1 | 3/2017 | Perusse et al. |
| 2017/0119660 A1 | 5/2017 | Temtsin-Krayz et al. |
| 2017/0290776 A1 | 10/2017 | Schobel et al. |
| 2019/0022023 A1 | 1/2019 | Schobel et al. |
| 2022/0401456 A1 | 12/2022 | Rabinowicz et al. |

FOREIGN PATENT DOCUMENTS

| | | |
|---|---|---|
| CA | 2317491 A1 | 7/1999 |
| CH | 639619 A5 | 11/1983 |
| CN | 1118254 A | 3/1996 |
| CN | 1777411 A | 5/2006 |
| CN | 101938991 A | 1/2011 |
| CN | 109310647 A | 2/2019 |
| DE | 2432925 A1 | 1/1976 |
| DE | 2449865 A1 | 4/1976 |
| DE | 2746414 A1 | 4/1979 |
| DE | 3630603 A1 | 3/1988 |
| DE | 19646392 A1 | 5/1998 |
| DE | 202004003781 U1 | 5/2004 |
| EP | 0014253 A2 | 8/1980 |

(56) References Cited

FOREIGN PATENT DOCUMENTS

| | | |
|---|---|---|
| EP | 0021178 A1 | 1/1981 |
| EP | 0065370 A1 | 11/1982 |
| EP | 0090560 A2 | 10/1983 |
| EP | 0095892 A1 | 12/1983 |
| EP | 0200508 A2 | 11/1986 |
| EP | 0219762 A1 | 4/1987 |
| EP | 0232877 A2 | 8/1987 |
| EP | 0241178 A1 | 10/1987 |
| EP | 0248548 A2 | 12/1987 |
| EP | 0250187 A2 | 12/1987 |
| EP | 0259749 A1 | 3/1988 |
| EP | 0273069 A1 | 7/1988 |
| EP | 0274431 A2 | 7/1988 |
| EP | 0285568 A2 | 10/1988 |
| EP | 0381194 A2 | 8/1990 |
| EP | 0440462 A1 | 8/1991 |
| EP | 0450141 A1 | 10/1991 |
| EP | 0452446 A1 | 10/1991 |
| EP | 0460588 A1 | 12/1991 |
| EP | 0514691 A2 | 11/1992 |
| EP | 0598606 A1 | 5/1994 |
| EP | 0636364 A1 | 2/1995 |
| EP | 0791575 A1 | 8/1997 |
| EP | 0949925 A2 | 10/1999 |
| EP | 1110546 A1 | 6/2001 |
| EP | 1143940 A2 | 10/2001 |
| EP | 1177788 A2 | 2/2002 |
| EP | 1219291 A1 | 7/2002 |
| EP | 1243523 A1 | 9/2002 |
| EP | 1267829 A1 | 1/2003 |
| EP | 1504765 A1 | 2/2005 |
| EP | 1591106 A1 | 11/2005 |
| EP | 1674078 A2 | 6/2006 |
| EP | 1852041 A2 | 11/2007 |
| EP | 1897543 A1 | 3/2008 |
| EP | 2105389 A1 | 9/2009 |
| EP | 2253224 A1 | 11/2010 |
| EP | 2305310 A1 | 4/2011 |
| EP | 2457581 A1 | 5/2012 |
| FR | 2716098 A1 | 8/1995 |
| GB | 1061557 A | 3/1967 |
| GB | 1154317 A | 6/1969 |
| GB | 1510999 A | 5/1978 |
| GB | 2166651 A | 5/1986 |
| GB | 2193891 A | 2/1988 |
| GB | 2447016 A | 9/2008 |
| JP | 56100714 | 8/1981 |
| JP | 62126950 | 6/1987 |
| JP | 2265444 | 10/1990 |
| JP | 473268 | 3/1992 |
| JP | 7322812 | 12/1995 |
| JP | 11255247 | 9/1999 |
| JP | 2000159658 A | 6/2000 |
| JP | 2001048196 A | 2/2001 |
| JP | 2001225851 A | 8/2001 |
| JP | 2001279100 A | 10/2001 |
| JP | 2003312688 A | 11/2003 |
| JP | 2004043450 A | 2/2004 |
| JP | 2004-131495 A | 4/2004 |
| JP | 2004222663 A | 8/2004 |
| JP | 2006-507277 A | 3/2006 |
| JP | 2006-509761 A | 3/2006 |
| JP | 2006143335 A | 6/2006 |
| JP | 2006-525370 A | 11/2006 |
| JP | 2008011194 A | 1/2008 |
| JP | 2008501019 A | 1/2008 |
| JP | 2012524771 A | 10/2012 |
| JP | 5147140 B2 | 2/2013 |
| JP | 2009084177 A | 3/2014 |
| JP | 2014532482 A | 12/2014 |
| JP | 2015-521996 A | 8/2015 |
| JP | 2015533155 A | 11/2015 |
| JP | 2013-530193 A | 10/2016 |
| JP | 2019519487 A | 7/2019 |
| JP | 2019519488 A | 7/2019 |
| KR | 2014-0084176 A | 7/2014 |
| WO | 1988007103 A1 | 9/1988 |
| WO | 9105540 A1 | 5/1991 |
| WO | 1992012704 A1 | 8/1992 |
| WO | 9215289 A1 | 9/1992 |
| WO | 9505416 A2 | 2/1995 |
| WO | 9518046 A1 | 7/1995 |
| WO | 1995023596 A1 | 9/1995 |
| WO | 9530601 A1 | 11/1995 |
| WO | 9615903 A1 | 5/1996 |
| WO | 9625150 A1 | 8/1996 |
| WO | 1996025638 A1 | 8/1996 |
| WO | 9731621 A1 | 9/1997 |
| WO | 9732573 A1 | 9/1997 |
| WO | 1997044016 A1 | 11/1997 |
| WO | 9810993 A1 | 3/1998 |
| WO | 9817251 A1 | 4/1998 |
| WO | 1998014179 A1 | 4/1998 |
| WO | 9935051 A1 | 7/1999 |
| WO | 9955312 A2 | 11/1999 |
| WO | 200002536 A1 | 1/2000 |
| WO | 2000002955 A1 | 1/2000 |
| WO | 0018365 A2 | 4/2000 |
| WO | 0024647 A1 | 5/2000 |
| WO | 2000027618 A1 | 5/2000 |
| WO | 0042992 A2 | 7/2000 |
| WO | 2000057858 A1 | 10/2000 |
| WO | 2001003917 A2 | 1/2001 |
| WO | 0130288 A1 | 5/2001 |
| WO | 2001034121 A2 | 5/2001 |
| WO | 0143728 A1 | 6/2001 |
| WO | 0156904 A1 | 8/2001 |
| WO | 0168452 A1 | 9/2001 |
| WO | 0170194 A1 | 9/2001 |
| WO | 0170197 A2 | 9/2001 |
| WO | 0191721 A2 | 12/2001 |
| WO | 0205789 A2 | 1/2002 |
| WO | 0207711 A1 | 1/2002 |
| WO | 2002005820 A1 | 1/2002 |
| WO | 0243657 A2 | 6/2002 |
| WO | 02062315 A1 | 8/2002 |
| WO | 2002064148 A2 | 8/2002 |
| WO | 02074238 A2 | 9/2002 |
| WO | 02091965 A1 | 11/2002 |
| WO | 03011259 A1 | 2/2003 |
| WO | 03015749 A1 | 2/2003 |
| WO | 03030881 A1 | 4/2003 |
| WO | 03030882 A1 | 4/2003 |
| WO | 03030883 A1 | 4/2003 |
| WO | 03043659 A1 | 5/2003 |
| WO | 2003101357 A1 | 12/2003 |
| WO | 2004009445 A2 | 1/2004 |
| WO | 2004026313 A1 | 4/2004 |
| WO | 2004035407 A1 | 4/2004 |
| WO | 2004/037222 A2 | 5/2004 |
| WO | 2004043165 A1 | 5/2004 |
| WO | 2004045305 A2 | 6/2004 |
| WO | 2004045537 A2 | 6/2004 |
| WO | 2004047815 A1 | 6/2004 |
| WO | 2004052335 A1 | 6/2004 |
| WO | 2004060298 A2 | 7/2004 |
| WO | 2004087084 A1 | 10/2004 |
| WO | 2004098567 A2 | 11/2004 |
| WO | 2004113193 A1 | 12/2004 |
| WO | 2005020933 A2 | 3/2005 |
| WO | 2005035776 A2 | 4/2005 |
| WO | 2005039499 A2 | 5/2005 |
| WO | 2005074867 A1 | 8/2005 |
| WO | 2005102287 A2 | 11/2005 |
| WO | 2005102863 A1 | 11/2005 |
| WO | 2005117905 A2 | 12/2005 |
| WO | 2005123074 A1 | 12/2005 |
| WO | 2006004480 A1 | 1/2006 |
| WO | 2006017462 A2 | 2/2006 |
| WO | 2006031209 A1 | 3/2006 |
| WO | 2006037425 A1 | 4/2006 |
| WO | 2006037979 A2 | 4/2006 |
| WO | 2006039264 A1 | 4/2006 |
| WO | 2006085210 A1 | 8/2006 |

(56) References Cited

FOREIGN PATENT DOCUMENTS

| | | | |
|---|---|---|---|
| WO | 2006133948 A2 | 12/2006 |
| WO | 2007015105 A2 | 2/2007 |
| WO | 2007067494 A1 | 6/2007 |
| WO | 2007070632 A2 | 6/2007 |
| WO | 2008011194 A2 | 1/2008 |
| WO | 2008025791 A1 | 3/2008 |
| WO | 2008036299 A2 | 3/2008 |
| WO | 2008040534 A2 | 4/2008 |
| WO | 2009027625 A2 | 3/2009 |
| WO | 2009044118 A2 | 4/2009 |
| WO | 2009052421 A1 | 4/2009 |
| WO | 2009105540 A1 | 8/2009 |
| WO | 2008149440 A1 | 8/2010 |
| WO | 2010122355 A1 | 10/2010 |
| WO | 2012/003968 A1 | 1/2012 |
| WO | 2011/010732 A1 | 1/2013 |
| WO | 2013063614 A1 | 5/2013 |
| WO | 2014006202 A1 | 1/2014 |
| WO | 2014057351 A1 | 4/2014 |
| WO | 2015078893 A1 | 6/2015 |
| WO | 2017023977 A1 | 2/2017 |
| WO | 2017192921 A1 | 11/2017 |
| WO | 2017192923 A1 | 11/2017 |
| WO | 2019067667 A1 | 4/2019 |
| WO | 2019067670 A1 | 4/2019 |

OTHER PUBLICATIONS

Blank, Z. et al., "Structural studies of organic gels by Sem", J. Material Science 9:1815-1822 (1974).
CAS Presents, "Common Chemistry", http://www.commonchemistry.org.ChemicalDetail.aspx?ref=25322-68-3&terms=polyeth . . . Oct. 28, 2009.
Huus et al., "Thermal Dissociation and Unfolding of Insulin", Biochemistry, 44: 11171-11177 (2005).
Steiner et al., "Organic Derivatives of Alginic Acid", Industrial and Engineering Chemistry; 43(9): 2073-2077 (1951).
Verdampfung, Kristallisation, Trocknung (Gnielinski, V et al., (Eds.)), pp. 161-181 (Vieweg & Sohn Verlagsgsellschaft mbH 1993). (partial English translation included.).
Giunchedi, P. and Conte, U., "Spray-drying as a preparation method of microparticulate drug delivery systems : an overview," S.T.P. Pharma. Sciences 6(4):276-290 (1995).
Guo, J.H. and Zerbe, H., "Water Soluble Film for Oral Administration," The 24th International Symposium on Controlled Release of Bioactive Materials, pp. 227-229 (Paper No. 5001-5003) (1997).
The Theory and Practice of Industrial Pharmacy (3rd Ed.) (Lachman, L et al. (eds.)), pp. 47-48, 51, 57, 64, 123-127, 346-369, 453-454, 461, 470, 479, 484, 491-492, 654-655 (1986).
Physical Pharmacy (4th Ed.) (Martin, A et al. (eds.)), pp. 423, 430-434, 453, 461, 484, 557-558, 560, 565-567 (1993).
Introductory Polymer Chemistry (Misra, G.S. (ed.)), Ch. 6, pp. 98-118 (1993).
Nishaoka, Y. et al., "Laser Diffraction Estimation of Particle Size Distribution of Slightly Water-Soluble Drugs Coexisting with Additives: Application to Solid Dosage Forms," Chem. Pharm. Bull. 40(6): 1563-1568 (1992).
Perumal, V.A. and Govender, T., "Investigating a New Approach to Film Casting for Enhanced Drug Content Uniformity in Polymeric Films," Drug Development and Industrial Pharmacy, 34:1034-1047 (2008).
Remington's Pharmaceutical Sciences (17th Ed.) (Gennaro, A.R. (ed.)), Ch. 37, pp. 713-740 (1985).
Shu, X.Z., et al., "Novel pH-sensitive citrate cross-linked chitosan film drug controlled release," Int. J. Pharmaceutics 212:19-28 (2001).
Pharmazeutische Technologie (4th Ed.), (Bauer, K.H. et al. (eds.)), pp. 94-94, 286-287 (Georg Thieme Verlag Stuttgart1993).
Brittian, H.G., "What Is the 'Correct' Method to Use for Particle-Size Determination?," Pharmaceutical Technology 96-98 (Jul. 2001).

"More Solutions to Sticky Problems: A Guide to Getting More From Your Brookfield Viscometer," Brookfield Engineering Laboratories, Inc. (1985).
DeGrande, G., et al., "Specialized Oral Mucosal Drug Delivery Systems: Patches," Drugs and the Pharmaceutical Sciences (Swarbrick, J. (ed.)), Ch. 12, pp. 285-317 (1995).
Polymer Science and Technology (Ebewele, R.O. (ed.)), pp. 1-23 (2000).
Etzler, F.M. and Sanderson, "Partilce Size Analysis: a Comparative Study of Various Methods," Part. Part. Syst. Charact. 12: 127-224 (1995).
Roddy, R.E., "A Controlled Trial of Nonoxynol 9 Film to Reduce Male-to-Female Transmission of Sexually Transmitted Diseases," New England J. Med. 339(8): 504-510 (1998).
Remington's Pharmaceutical Sciences (18th Ed.) (Gennaro, A.R. (ed.)), Ch. 19, pp. 296-298 (1990).
Etzler, F.M., "Particle Size Analysis: a Comparison of Methods," Polymeric Materials: Science & Engineering 87:335-336 (2002).
Patel, V.F. et al., "Advances in oral transmucosal drug delivery," J. Controlled Release 153: 106-116 (2011).
"Adsorption," Kirk-Othmer Encyclopedia of Chemical Technology (4th Ed.) pp. 493-494 (Wiley 1991).
"Matrix," Webster's Third New International Dictionary of the English Language Unabridged (Gove, P.B. (ed.)) (G. & C. Merriam Company 1968).
Plastic Films (Osborn, K.R. and Jankins, W.A. (eds.), p. 89 (1992).
Martinez, M.N. and Amidon, G.L., "A Mechanistic Approach to Understanding the Factors Affecting Drug Absorption: A Review of Fundamentals," J. Clin. Pharmacol. 42:620-643 (2002).
Amidon, G.L. et al., "A Theoretical Basis for a Biopharmaceutical Drug Classification: The Correlation of in Vitro Drug Product Dissolution and in Vivo Bioavailability," Pharm. Res. 12(3):413-420 (1995).
Anders, R. and Merkle, H.P., "Evaluation of laminated mucoadhesive patches for buccal drug delivery," Int. J. Pharmaceutics 49: 231-240 (1989).
Pharmaceutical Dosage Forms and Drug Delivery Systems (7th Ed.) (Ansel, H.C. et al. (eds.)), p. 66 (1999).
Apicella, A. et al., "poly(ethylene oxide) (PEO) and different molecular weight PEO blends monolithic devices for drug release," Biomaterials 14(2):83-90 (1993).
Pharmazeutische Technologie (5th Ed.) (Bauer, K.H. et al. (eds.)), pp. 208-209 (Stuttgart Jena Lubeck Ulm 1997).
Bowser, T.J. and Wilhelm, L.R., "Modeling Simultaneous Shrinkage and Heat and Mass Transfer of a Thin. Nonporous Film During Drying," J. Food Sci. 60(4): 753-757 (1995).
Theory of pharmaceutical systems: vol. II (Carstensen, J.T. (ed.)), pp. 4-9 (1973).
Cassidy, J. P. et al., "Controlled buccal delivery of buprenorphine," J. Controlled Release 25:21-29 (1993).
Eudragit E 100, Eudragit E PO, and Eudragit E 12,5, Technical Information, Evonik Inductries AG, (2012).
Eudragit L 100 and Eudragit S 100, Technical Information, Evonik Inductries AG, (2012).
Europaisches Arzneibuch (3rd Ed.), pp. 142-143 (Deutscher Apotheker Verlag 1997).
European Pharmacopeia (3rd Ed.), p. 134 (1997).
Frankman, O. et al., "clinical Evaluation of C-Film, a Vaginal Contraceptive," J. Int. Med. Res. 3:292-296 (1975).
Friend, D.R., "Polyacrylate resin microcapsules for taste masking of antibiotics," J. Microencapsulation 9(4):469-480 (1992).
Fuller, C.S. et al., "Interactions in poly(ethylene oxide)-hydroxylpropyl methylcellulose blends," Polymer 42:9583-9592 (2001).
Save, T. et al., "Comparative Study of Buccoadhesive Formulations and Sublingual Capsules of Nifedipine," J. Pharm. Pharmacol. 46:192-195 (1994).
Save, T. and Vankitachalam, P., "Studies on Solid Dispersions of Nifedipine," Drug Development and Industrial Pharmacy 18(15): 1663-1679 (1992).
Roy, G.M., "Taste Macking in Oral Pharmaceuticals," Pharmaceutical Technology, pp. 84-99 (Apr. 1994).

(56) References Cited

OTHER PUBLICATIONS

Guo, J.H. and Cookock, K.M., "Bioadhesive Polymer Buccal Patches for Buprenorphine Controlled Delivery: Solubility Consideration," Drug Development and Industrial Pharmacy 21(7): 2013-2019 (1995).
Mixing in the Process Industries (2nd Ed.) Harnby, N. et al. (eds.)), pp. 3, 115 (Butterworth Heinemann 1997).
Himics, R, and Pineiro, R., "The Importance of Particle Size in Liquid Coatings," Products Finishing 63(2):00329940 (1998).
Handbook of Pharmaceutical Excipients (Rowe, R. et al. (eds.)), pp. 326, 513, 522 (2009).
Ilango, R. et al., "In-Vitro Studies on Buccal strips of Glibenclamide using Chitosan," Indian J. Pharm. Sci. 59 (5):232-235 (1997).
Ishikawa, T. et al., "Preparation and Evaluation of Tablets Rapidly Disintegrating in Saliva Containing Bitter-Taste-Masked Granules by the Compression Method," Chem. Pharm. Bull. 47(10): 1451-1454 (1999).
Kaya, S. and Kaya, A., "Microwave drying effects on properties of whey protein isolate edible films," J. Food Engineering, 43: 91-96 (2000).
Al-Ghananeem et al., "Effect of pH on Sublingual Absorption of Oxycodone Hydrochloride", AAPS PharmSciTech; Article 23, 7(1) (2006) (http://www.aapspharmscitec.org).
Bhumkar et al., "Chitosan Reduced Gold Nanoparticles as Novel Carriers for Transmucosal Delivery of Insulin", Pharmaceutical Research; 24(8): 1415-1426 (2007).
Bowen P., "Particle Size Distribution Measurement from Millimeters to Nanometers and from Rods to Platelets", Journal of Dispersion Science and Technology; 23(5): 631-662 (2002).
Trademark Reg. No. 2,944, 841-registered Apr. 26, 2005 to Reynolds Metal Co for "EZ Slide".
Hariharan et al., "Thin Film Technology, Orally Dissolving Film Strips (ODFS): The Final Evolution of Orally Dissolving Dosage Forms," Drug Delivery Technology; 9(2): 24-29 (2009).
Joshi et al., "Gold Nanoparticles as Carrier for Efficient Transmucosal Insulin Delivery", Langmuir; 22: 300-305 (2006).
Ojeda et al., "Preparation of multifunctional glyconanoparticles as a platform for potential carbohydrate-based anticancer vaccines", Carbohydrate Research; 342: 448-459 (2007).
U.S. Department of Health and Human Services Food and Drug Administration Center for Drug Evaluation and Research (CDER) "Guidance for Industry—Incorporation of Physical-Chemical Identifiers into Solid Oral Dosage Form Drug Products for Anticounterfeiting" Silver Spring, MD; 1-8 (Jul. 9, 2009).
Boo, Woong Jae, "Characterization of Thin Film Properties of Melamine Based Dendrimer Nanoparticles", Thesis for Texas A&M University, Dec. 2003.
"Suboxone Subligualtabletten" in: Verlag Rote Liste Service GmbH: "Rote Liste 2008" 2008, Verlag Rote Liste Service GmbH, Frankfurt/Main, XP00264986, p. 39018, the whole document.
Transaction History for Ex Parte Reexamination Control No. 90/012,098, current as of.
Index of Documents for Inter Partes Review Case No. IPR2013-00316, current as of Aug. 29, 2017.
Transaction History for Ex Parte Reexamination Control No. 90/012,097, current as of Aug. 29, 2017.
Index of Documents for Inter Partes Review Case No. IPR2013-00315, current as of Aug. 29, 2017.
Transaction History for Inter Partes Reexamination Control No. 95/002,171, current as of Aug. 29, 2017.
Transaction History for Inter Partes Reexamination Control No. 95/001,753, current as of Aug. 29, 2017.
Transaction History for Inter Partes Reexamination Control No. 95/002,170, current as of Aug. 29, 2017.
Index of Documents for Inter Partes Review Case No. IPR2014-00794, current as of Aug. 29, 2017.
Index of Documents for Inter Partes Review Case No. IPR2015-00165, current as of Aug. 29, 2017.
Index of Documents for Inter Partes Review Case No. IPR2015-00167, current as of Aug. 29, 2017.
Index of Documents for Inter Partes Review Case No. IPR2015-00168, current as of Aug. 29, 2017.
Index of Documents for Inter Partes Review Case No. IPR2015-00169, current as of Aug. 29, 2017.
Index of Documents for Inter Partes Review Case No. IPR2016-00281, current as of Aug. 29, 2017.
Index of Documents for Inter Partes Review Case No. IPR2016-00282, current as of Aug. 29, 2017.
Index of Documents for Inter Partes Review Case No. IPR2016-01111, current as of Aug. 29, 2017.
Index of Documents for Inter Partes Review Case No. IPR2016-01112, current as of Aug. 29, 2017.
Index of Documents for Inter Partes Review Case No. IPR2017-00200, current as of Aug. 29, 2017.
Index of Documents for Inter Partes Review Case No. IPR2017-01557, current as of Aug. 29, 2017.
Index of Documents for Inter Partes Review Case No. IPR2017-01582, current as of Aug. 29, 2017.
"Cellulose" Kirk-Othmer Concise Encyclopeida of Chemical Technology; Abridged version of the 24 Volume, NY, Wiley; 227-228 (1978-1984).
"Excipients, Croscarmellose Sodium", Pformulate Excipients, http://www.pformulate.com/croscarmellose.htm (Sep. 29, 2002).
Atridox(R) (Doxycycline Hyclate) Product Label.
Barton, S et al. "Citric Buffer Calculation", Version 1.1, Nov. 19, 2000.
Birkhauser, "Cell Encapsulation Technology and Therapeutics" (Jan. 5, 2009).
Bodmeier, Roland, "Evaluation of Drug-Containing Polymer Films Prepared from Aqueous Latexes", Pharmaceutical Research, vol. 6, No. 8 (1989).
Cholewinski et al., Pharmaceutica Acta Helvetiae, 71:405-419, 1996.
Croscarmellose sodium http://ww.nbent.com/crosscarmellose.htm (Mar. 29, 2005).
Delsym Product Label (Feb. 13, 2007).
Di Donato et al., J. Biol. Chem, 268(7): 4745-4751, 1993.
Eiamtrakarn et al., "Gastrointestinal Mucoadhesive Path System (GI-MAPS) for oral administration of G-CSF, a model protein", Bipmaterials 23: 145-152 (2002).
Endo and Ueda, Fabad J. Pharm. Sci., 29:27-38, 2004.
Gaylor Razafimamonjison, Michel Jahiel, Thierry Duclos, Panja Ramanoelina, Fanja Fawbush, and Pascal Danthu, "Bud, leaf and stem essential oil composition of Syzygium aromaticum from Madagascar, Indonesia and Zanzibar" International Journal of Basic and Applied Sciences, 3 (3) (2014) 224-233. (Year: 2014).
Narayanan Gopalakrishnan, Padmanabha Pillai V Shanti and Cadavallur Subrahmanian Narayanan, "Composition of Clove (<i>Syzygium aromaticum</i>) Bud Oil Extracted Using Carbon Dioxide", Journal of the Science of Food and Agriculture, 1990, 50, 111-117. (Year: 1990).
S. Juglal, R. Govinden, and B. Odhav, "Spice Oils for the Control of Co-Occurring Mycotoxin-Producing Fungi", Journal of Food Protection, 65(4), 2002, 683-687. (Year: 2002).
Myun Cheng, Zhenhua Xu, Minglu Ma, and Tongwen Xu, "Dendrimers as Drug Carriers: Applications in Different Routes of Drug Administration", Journal of Pharmaceutical Sciences, 97(1), 2008, 123-143. (Year: 2008).
Metin Tülü and Ali Serol Ertürk, "Dendrimers as Antibacterial Agents", A Search for Antibacterial Agents, Chapter 6, 2012, Publisher: InTech, p. 89-106. (Year: 2012).
Nisreen Hassan, Abdul Ahad, Mushir Ali and Javed Ali, "Chemical permeation enhancers for transbuccal drug delivery", Expert Opinion Drug Delivery, 2010, 7(1), 97-112. (Year: 2010).
Metallic Pigments in Polymers, p. 132 (Rapra Technology Limited 1999).
White, J.G., "In Situ Determination of Delavirdine Mesylate Particle Size in Solid Oral Dosage Forms," Pharmaecutical Research 16(4):545-548 (1999).
Yamamura, K. et al., "Oral Mucosal Adhesive Film Containing Local Anesthetics: In Vitro and Clinical Evaluation," J. Biomed. Mater. Res. (Appl. Biomater.) 43:313-317 (1998).

(56) References Cited

OTHER PUBLICATIONS

Pharmazeutische Technologie: Insustrielle Herstellung und Entwicklung von Arzneimitteln (Zimmermann, I. (ed.)), p. 246 (Springer-Verlag 1998).
Modern coating technology systems for paper, film and foil (Shepherd, F. (ed.)), p. 5 (Emap Maclaren Ltd. 1995).
"Adsorption at Solid Surfaces," Encyclopedia of Pharmaceutical Technology (Swarbrick (ed.)), p. 73 (1988).
Photograph of Tetracycline HCL (https://de.wikipedia.org/wiki/Tetracycline#/media/File: Tetracycline-HCL_substance_photo.jpg).
Textbook of Polymer Science (2nd Ed.) pp. 1-22 (Wiley 1971).
Thimmashetty, J. et al., "Preparation and Evaluation of Buccal Dosage Forms of Insulin.".
Thimmashetty, J. et al., "Design and In Vivo Evaluation of Carvedilol Buccal Mucoadhesive Patches," Pak. J. Pharm. Sci. 21(3):241-248 (2008).
Elemente des Apparatebause, (Titz, H. (ed.)), pp. 546-669 (Springer-Verlag 1992). (includes partial English translation.).
The United States Pharmacopeia (20th Rev.), pp. 3-4, 12, 16, 955-957, 1023, 1030-1031, 1412, 1451 (USP 1980).
Varanda, F. et al., "Solubility of Antibiotics in Different Solvents. 1. Hydrochloride Forms of Tetracycline, Moxifloxacin, and Ciprofloxacin," Ind. Eng. Chem. Res. 45:6368-6374 (2006).
Phramazeutische Technologie fur Studium und Beruf (Voigt, R. (ed.)), p. 65 (Ullstein Mosby 1995).
Polymer Molecular Weights (Slade, p. E. (ed.), p. 1-8 (Marcel Dekker, Inc. 1975).
McNeill, J. Robert, et al., "A systematic review of mechanisms by which natural products of plant origin evoke vasodilatation," Can. J. Physiol. Pharmacol (2006) vol. 84, pp. 803-821.
Senel, S., et al., "Drug permeation enhancement via buccal route: possibilities and limitations," Journal of Controlled Release (2001) vol. 72, pp. 133-144.
Nicolazzo, Joseph A., et al., "Buccal penetration enhancers-How do they really work?," Journal of Controlled Release (2005) vol. 105, pp. 1-15.
Amores, Sonia, et al., "An improved cryopreservation method for porcine buccal mucosa in ex vivo drug permeation studies using Franz diffusion cells," European Journal of Pharmaceutical Science (2014) vol. 60, pp. 49-54.
Sattar, Mohammed, et al., "Oral transmucosal drug delivery—Current status and future prospects," International Journal of Pharmaceutics (2014) vol. 471, pp. 498-506.
Gimeno, Alvaro, et al., "Transbuccal delivery of doxepin: Studies on permeation and histological investigation," International Journal of Pharmaceutics (2014) vol. 471, pp. 650-654.
Ong, Charlene M.Y., et al., "Permeation of quinine across sublingual mucosa, in vitro," International Journal of Pharmaceutics (2009) vol. 366, pp. 58-64.
U.S. Pat. No. 7,357,891, U.S. Appl. No. 90/012,098, Ex Parte Reexamination.
U.S. Pat. No. 7,357,891, IPR2013-00316, Inter Partes Review.
U.S. Pat. No. 7,425,292, U.S. Appl. No. 90/012,097, Ex Parte Reexamination.
U.S. Pat. No. 7,425,292, IPR2013-00315, Inter Partes Review.
U.S. Pat. No. 7,666,337, 95/002, 171, Inter Partes Reexamination.
U.S. Pat. No. 7,824,588, U.S. Appl. No. 95/001,753, Inter Partes Reexamination.
U.S. Pat. No. 7,897,080, U.S. Appl. No. 95/002,170, Inter Partes Reexamination.
U.S. Pat. No. 8,017,150, IPR2016-00282, Inter Partes Review.
U.S. Pat. No. 8,603,514, IPR2016-00281, Inter Partes Review.
U.S. Pat. No. 8,652,378, IPR2014-00794, Inter Partes Review.
U.S. Pat. No. 8,765,167, IPR2015-00165, Inter Partes Review.
U.S. Pat. No. 8,765,167, IPR2015-00167, Inter Partes Review.
U.S. Pat. No. 8,765,167, IPR2015-00168, Inter Partes Review.
U.S. Pat. No. 8,765,167, IPR2015-00169, Inter Partes Review.
U.S. Pat. No. 8,603,514, IPR2016-01111, Inter Partes Review.
U.S. Pat. No. 8,017,150, IPR2016-01112, Inter Partes Review.
U.S. Pat. No. 8,603,514, IPR2017-00200, Inter Partes Review.
U.S. Pat. No. 8,603,514, IPR2017-01557, Inter Partes Review.
U.S. Pat. No. 8,603,514, IPR2017-01582, Inter Partes Review.
U.S. Appl. No. 10/074,272, filed Feb. 14, 2002.
U.S. Appl. No. 10/768,809, filed Jan. 30, 2004.
U.S. Appl. No. 10/856,176, filed May 28, 2004.
English Translation of Office Action issued on Nov. 29, 2021 in KR Application No. 1020187035240.
English Translation of FER issued on Oct. 7, 2021 in IN Application No. 202017016904.
English Translation of OA issued on Jan. 26, 2022 in JP Application No. 2018-558224.
English Translation of FER issued on Oct. 26, 2021 in IN Application No. 202017016905.
English Translation of OA issued on Apr. 6, 2022 in IL Application No. 262751.
English Translation of OA issued on May 31, 2022 in JP Application No. 2018-558225.
Kesharwani, Payal et al. "Biomedical applications of hydrogels in drug delivery system: An update." Journal of Drug Delivery Science and Technology (2021): n. pag.
Tangri, Pranshu et al. "Oral Mucoadhesive Drug Delivery Systems: a Review." (2011).
Debotton, Nir and Arik Dahan. "Applications of Polymers as Pharmaceutical Excipients in Solid Oral Dosage Forms." Medicinal Research Reviews 37 (2017): n. pag.
English Translation of Final Rejection issued on Jul. 20, 2022 in CN Application No. 201780037588.X.
English Translation of Final Rejection issued on Jul. 8, 2022 in CN Application No. 201780037587.5.
English Translation of OA issued on Apr. 22, 2022 in KR Application No. 10-2018-7035236.
English Translation of OA issued on Jul. 26, 2022 in BR Application No. BR112020005875-0.
English Translation of OA issued on Aug. 16, 2022 in BR Application No. BR112020005948-0.
English Translation of OA issued on Aug. 16, 2022 in BR Application No. BR112020005967-6.
English Translation of Official Hearing issued on Jul. 15, 2022 in IN Application No. 202017016904.
Restriction Requirement issued on Sep. 29, 2022 in U.S. Appl. No. 17/086,409.
English Translation of OA issued on Oct. 28, 2022 in JP Application No. 2020-517419.
English Translation of OA issued on Oct. 28, 2022 in JP Application No. 2020-517586.
Non-Final Rejection issued on Oct. 28, 2022 in U.S. Appl. No. 15/791,249.
English Translation of Official Notification issued on Sep. 28, 2022 in IL Application No. 273485.
English Translation of Official Notification issued on Sep. 28, 2022 in IL Application No. 292487.
English Translation of OA issued on Nov. 1, 2022 in JP Application No. 2020-538776.
Final Rejection issued on Nov. 17, 2022 in U.S. Appl. No. 16/143,821.
Final Rejection issued on Nov. 18, 2022 in U.S. Appl. No. 16/143,678.
English Translation of Official Notification issued on Oct. 27, 2022 in IL Application No. 273479.
English Translation of Examination Report issued on Dec. 12, 2022 in IL Application No. 273477.
Restriction Requirement issued on Jan. 20, 2023 in U.S. Appl. No. 17/973,345.
English Translation of Office Action issued on Dec. 20, 2022 in CN Application 201880063175.3.
English Translation of Office Action issued on Dec. 22, 2022 in CN Application 201880062678.9.
Notice of Allowance issued on Feb. 27, 2023 in KR Application 10-2018-7035236.
Non-Final Rejection issued on Mar. 2, 2023 in U.S. Appl. No. 17/973,345.
Final Rejeciton issued on Jun. 22, 2023 in U.S. Appl. No. 17/973,345.
Advisory Action issued on Aug. 18, 2023 in U.S. Appl. No. 17/973,345.

(56) References Cited

OTHER PUBLICATIONS

Office Action issued on Dec. 23, 2022 in EP Application 18786579.5.
Official Notification issued on Dec. 27, 2022 in IL Application 273479.
English Translation of Office Action issued on Mar. 28, 2023 in JP Application 2018-558225.
English Translation of Office Action issued on Jan. 28, 2023 in CN Application 201880062717.5.
English Translation of Office Action issued on Jan. 13, 2023 in KR Application 10-2018-7035240.
English Translation of Rejection issued on Jun. 30, 2023 in KR Application 10-2018-7035240.
Restriction Requirement issued on Feb. 17, 2023 in U.S. Appl. No. 17/098,324.
Examination Report issued on Mar. 24, 2023 in EP Application 18786591.0.
Non-Final Rejection issued on Mar. 2, 2023 in U.S. Appl. No. 16/143,036.
Non-Final Rejection ussed on Mar. 3, 2023 in U.S. Appl. No. 17/835,442.
Examination Report issued on May 24, 2023 in EP Application 20820711.8.
Non-Final Rejection issued on Mar. 21, 2023 in U.S. Appl. No. 17/576,923.
Examiner's Report issued on Jun. 7, 2023 in CA Application 3022797.
English Translation of Office Action issued on Jul. 7, 2023 in KR Application 10-2020-7012106.
English Translation of Office Action issued on Jul. 7, 2023 in KR Application 10-2020-7012033.
English Translation of Office Action issued on Jun. 30, 2023 in KR Application 10-2020-7011909.
Non-Final Rejection issued on Jun. 29, 2023 in U.S. Appl. No. 17/086,409.
Notice of Allowance issued on Jun. 16, 2023 in CA Application 2771089.
English Translation of Office Action issued on Aug. 23, 2023 in CN Application 201880062678.9.
Final Rejection issued on Aug. 1, 2023 in U.S. Appl. No. 15/791,249.
English Translation of Office Action issued on Sep. 11, 2023 in JP Application 2020-538776.
English Translation of Office Action issued on Jul. 26, 2023 in JP Application 2020-517586.
Examiner's Report issued on Jul. 20, 2023 in CA Application 3022840.
English Translation of Office Action issued on Aug. 28, 2023 in IL Application No. 262751.
Non-Final Rejection issued on Sep. 7, 2023 in U.S. Appl. No. 16/143,678.
English Translation of Office Action issued on Aug. 31, 2023 in CN Application 202080092463.9.
Rule 161(1) and 162 issued on Sep. 5, 2023 in EP Application 22703176.2.
Jung et al The Usability of Diazepam Buccal Soluble Film as an Oral Treatment in Adult Patients with Epilepsy.
Non-Final Rejection issued on Oct. 2, 2023 in U.S. Appl. No. 17/098,324.
English Translation of Office Action issued on Oct. 10, 2023 in CN Application 201880063175.3.
Final Rejection issued on Oct. 13, 2023 in U.S. Appl. No. 17/576,923.
Office Action issued on Oct. 25, 2023 in CN Application 202080089502.X.
Engel, June V PhD, "The Benefits of Eating Fibre" http://www.diabetes.ca/common/PrintVersion.asp?ID=45493 May 11, 2005.
Flick, E., Water-Soluble Resins—An Industrial Guide, 1991 (2nd Ed.) William Andrew Publishing/Noyes, pp. 389-392.
Goldberg et al., "Biotechnology and Food Ingredients", Springer: 352 (1991).
Hadvary et al., "Inhibition of pancreatic lipase in vitro by the covalent inhibitor tetrahydrolistatin", Biochem J.; 256: 357-361 (1988).
Ko et al., "Behavior of etrahydrolipstatin in biological model membranes and emulsions", J. of Lipid Research; 38:1544-1552 (1997).
Kuhtreiber. In Cell Encapsulation and Therapeutics . Copyright 1999.
Lazaridou et al.; Thermophysical properties of chitosan, chitosanstarch and chitosan-pullulan films near the glass transition; Elsevier Science Ltd.; 2002; pp. 179-190.
Leathers, Appl. Microbiol. Biotechnol., 62: 468-473, 2003.
Le Person, S. Le et al., "Near infrared drying of pharmaceutical thin films: experimental analysis of internal mass transport," Chemical Engineering and Processing; (1998) pp. 257-263, 37.
Mahmood et al., "A limited sampling method for the estimation of AUC and Cmax of cabamazepine and carbamazepine epoxide folowing a single and multiple dose of a sustained-release product", Br J Clin Pharmacol; 45:241-246 (1998).
Mix. http://www.askoxford.com/concise_oed/mixx?view=uk. Accessed Dec. 23, 2004.
Nicorete Packaging (Aug. 29, 2006).
Oriski, S.C., "Johnson debuts cutter for new Saran film" Packaging World Oct. 1, 2004, http://www.packworld.com/view-18051.
Peh Kok Khiang et al., "Polymeric Films as Vehicle for Buccal Delivery: Swelling, Mechanical, and Bioadhesive Properties," J Pharm Pharmaceut Sci (1999) pp. 53-61, 2:2.
Polyethylenglykoke, Fachgebit Chemie, Unterthema Makromolekulare Chemie, XP-002298105 (Sep. 20, 2004).
Repka et al., "Bioadhesive properties of hydroxypropylcellulose topical films produced by hot-melt extrusion," Journal of Controlled Release, 70: 341-351 (2001).
Repka et al., "Influence of Vitamin E TPGS on the properties of hydrophilic films produced by hot-melt extrusion," Int. J. Pharmaceutics, 202: 63-70 (2000).
Senel, S., et al., "Chitosan films and hydrogels of chlorhexidine gluconate for oral mucosal delivery", Int. J. Pharmaceutics, 193: pp. 197-203 (2000).
Stella, V., et al., "Gliadin Films. I: Preparation and in vitro evaluation as a carrier for controlled drug release", Int., J. Pharmaceutics, 121: pp. 117-121 (1995).
Sudafed & Sudafed PE, http://www.sudafed.com/products/pe_quickstrips.html (Aug. 17, 2007).
Well—Definition of from The American Heritage College Dictionary, 3rd Ed., p. 1531 (1993).
Bauer, K.H. et al., "Pharmazeutische Technologie", pp. 208-209 (1997).
Pinnamanemi, S. et al., "Formulation approaches for orally administered poorly soluble drugs", Pharmazie 57(5): 291-300 (2002).
Chaumeil, J.C., "Micronization: A Method of Improving the Bioavailability of Poorly Soluble Drugs", Methods and Findings in Experimental and Clinical Pharmacology 20(3): 211-215 (1998).
Voigt, R. et al., "Pharmaseutische Technology fur Studium und Berf", pp. 179-180 (1995).
Nanda, A. et al., "An update on taste masking technologies for oral pharmaceuticals", Indian J Pharma Sci 64(1): 10-17 (2002).
Bornschein, M. et al., "Micro- und Nanopartikeln als Arzneliestofftragersysteme unter besonderer Berucksichtigung der Herstellungsmethoden", Die Pharmazie 44(9): 585-593 (1989).
Cohen E. et al., "Modern Coating and Drying Technology", pp. 268-277 (1992).
International Search Report and Written Opinion for PCT/US2018/052927, dated Dec. 19, 2018.
Ho, N.F.H., et al., "(D) Routes of delivery: Case studies," Advanced Drug Delivery Reviews, vol. 8, No. 2-3 (Mar. 1, 1992) pp. 197-236.
Merkle, H.P., et al., "Buccal delivery for peptide drugs," Journal of Controlled Release, vol. 21 No. 1-3 (1992).
Wolany, Gregor, "Zur bukkalen Applikation und Absorption des Oktapeptids Octreotid," (Jan. 1, 1990).
International Search Report and Written Opinion for PCT/US2018/053042, dated Dec. 11, 2018.
International Search Report and Written Opinion for PCT/US2018/053026, dated Dec. 14, 2018.

(56) References Cited

OTHER PUBLICATIONS

Office Action mailed in European Patent Application No. 17723616.3 dated Mar. 3, 2020.
Office action mailed in European Patent Application No. 17723617.3 dated Mar. 3, 2020.
Nicolazzo et al. "Modification of buccal drug delivery following pretreatment with skin penetration enhancers," Journal of Pharmaceutical Sciences, vol. 93, Issue 8, 2004, pp. 2054-2063.
Stanczak et al., "Prodrugs and Soft Drugs", Pharmacological Reports, 2006, 58, 599-613.
Nicolazzo et al. "Assessment of the Effect of Sodium Dodecly Sulfate on the Buccal Permeability of Caffeine and Estradiol", Journal of Phamaceutical Sciences, col. 93, No. Feb. 2, 2004, 431-440.
Sudhakar et al. "Buccal bioadhesive drug delivery-A promising option for orally less effecient drugs", Journal of Controlled Release 114 (2006) 15-40.
Van Ginkel, C.G. (1995). "Biodegradability of cationic surfactants." In: Karsa D.R., Porter M.R. (eds) Biodegrability of Surfactants, Springer, Dordrecht; pp. 1-21 (Year: 1995).
Lu et al. (Jan. 12, 2017). "Impact of Endogenous Bile Salts on the Thermodynamics of Supersaturated Active Pharmaceutical Ingredient Solutions." Cryst. Growth Des., 17, pp. 1264-1275 (Year: 2017).
Rogawski et al., "Diazempam buccal film for the treatment of acute seizures". Epilepsy and Behavior, Academic Press, San Diego, CA, US Vo. 101. Nov. 5, 2019.
Health Syneos: "A Randomized, Open-Label, 2-Sequence, 3 Treatment, Crossover Study to Evaluate the Pharmacokinetics of Single Doses of Diazepam Buccal Film (DBF) (Aquestive Therapeutics) Compated With Diastat Rectal Gel (Valeant Pharmaceuticals North America) in Aduly Male and Femal Subjects on Concomitant Reg", May 25, 2019 (May 24, 2019).
Streubel et al., "Bimodal drug release achieved with multi-layer matrix tablets: transport mechanisms and device design", Journal of Controlled Release, Elsevier, Amsterdam, NL. vol. 69, No. 3, Dec. 3, 2000 (Dec. 3, 2000).
Menezes, et al. "Hypotensive activity of terpenes found in essential oils." Zeitschrift fur Naturforschung. C, Journal of biosciences vol. 65,9-10 (2010): 562-6.
Tsai, Tung-Hu et al. "Vasorelaxing alkaloids and flavonoids from Cassytha filiformis." Journal of natural products vol. 71,2 (2008): 289-91.
Luna-Vázquez, Francisco J et al. "Vasodilator compounds derived from plants and their mechanisms of action." Molecules (Basel, Switzerland) vol. 18,5 5814-57. May 17, 2013.
Park, Soo-Hyun et al. "The analgesic effects and mechanisms of orally administered eugenol." Archives of pharmacal research vol. 34,3 (2011): 501-7.
Chang, Huang-Kuang et al. "Stimulatory effect of cinnamic acid analogues on alpha1A-adrenoceptors in-vitro." The Journal of pharmacy and pharmacology vol. 55,6 (2003): 833-7.
Lahlou, Saad et al. "Cardiovascular effects of eugenol, a phenolic compound present in many plant essential oils, in normotensive rats." Journal of cardiovascular pharmacology vol. 43,2 (2004): 250-7.
Feddersen, C O et al. "Arachidonic acid causes cyclooxygenase-dependent and -independent pulmonary vasodilation." Journal of applied physiology (Bethesda, Md.: 1985) vol. 68,5 (1990): 1799-808.
International Search Report and Written Opinion dated Mar. 1, 2021 in International Application No. PCT/US2020/060464.
International Search Report and Written Opinion dated Feb. 9, 2021 in International Application No. PCT/US2020/058357.
International Search Report and Written Opinion dated Jul. 17, 2017 in International Application No. PCT/US2017/031167.
International Search Report and Written Opinion dated Jul. 10, 2017 in International Application No. PCT/US2017/031170.
Restriction Requirement dated Oct. 7, 2019 in U.S. Appl. No. 15/724,234.
Non-Final Rejection dated Mar. 13, 2020 in U.S. Appl. No. 15/724,234.
Final Rejection dated Aug. 17, 2020 in U.S. Appl. No. 15/724,234.
Restriction Requirement dated Jun. 18, 2021 in U.S. Appl. No. 15/724,234.
Office Action dated Jun. 1, 2021 in Brazilian Patent Application No. 112018072467-0.
Office Action dated Mar. 4, 2021 in European Application No. 17723616.3.
First Examination Report dated Jul. 24, 2020 in Indian Application No. 201817045308.
Non-Final Rejection dated Aug. 27, 2018 in U.S. Appl. No. 15/791,249.
Final Rejection dated Jun. 19, 2019 in U.S. Appl. No. 15/791,249.
Advisory Action dated Oct. 21, 2019 in U.S. Appl. No. 15/791,249.
Non-Final Rejection dated Dec. 12, 2019 in U.S. Appl. No. 15/791,249.
Final Rejection dated Jun. 9, 2020 in U.S. Appl. No. 15/791,249.
Advisory Action dated Oct. 9, 2020 in U.S. Appl. No. 15/791,249.
Non-Final Rejection dated Mar. 29, 2021 in U.S. Appl. No. 15/791,249.
Restriction Requirement dated May 1, 2019 in U.S. Appl. No. 16/143,036.
Non-Final Rejection dated Nov. 18, 2019 in U.S. Appl. No. 16/143,036.
Final Rejection dated May 13, 2020 in U.S. Appl. No. 16/143,036.
Advisory Action dated Aug. 27, 2020 in U.S. Appl. No. 16/143,036.
Non-Final Rejection dated Jan. 6, 2021 in U.S. Appl. No. 16/143,036.
Final Rejection dated Jun. 7, 2021 in U.S. Appl. No. 16/143,036.
Non-Final Rejection dated Nov. 4, 2020 in U.S. Appl. No. 16/143,821.
Office Action dated Jun. 1, 2021 in Japanese Application No. 2018-558224.
Final Rejection dated May 4, 2021 in U.S. Appl. No. 16/143,821.
Restriction Requirement dated Feb. 19, 2020 in U.S. Appl. No. 16/143,821.
Aqil, Mohammed et al. "Status of terpenes as skin penetration enhancers." Drug discovery today vol. 12,23-24 (2007): 1061-7.
Office Action dated Jun. 29, 2021 in Japanese Application No. 2018-558225.
English Translation of Office Action dated Aug. 3, 2021 in Chinese Application No. 201780037587.5.
English Translation of Office Action dated Aug. 3, 2021 in Chinese Application No. 201780037588.X.
Alayoubi et al., "Development of a fast dissolving film of epinephrine hydrocholoride as a potential anaphylactic treatment for pediatrics", Journal of Pharmaceutical Development and Technology, vol. 22:8, Jan. 6, 2016, pp. 1012-1016. <https://doi.org/10.3109/10837450.2015.1131715>.
First Examination Report dated Oct. 13, 2021 in Indian Application No. 202017016896.
Office Action issued on Jul. 21, 2021 in European Application No. 17723617.1.
Restriction Requirement issued on Aug. 5, 2021 in U.S. Appl. No. 16/143,678.
Notice of Allowance issued on Aug. 20, 2021 in U.S. Appl. No. 15/587,364.
Issue Notification issued on Feb. 24, 2022 in U.S. Appl. No. 15/724,234.
Hussain, Anwar et al., "Prodrug Approaches to Enhancement of Physicochemical Properties of Drugs IV: Novel Epinephrine Prodrug," Journal of Pharmaceutical Sciences (1976) vol. 65, No. 10 pp. 1510-1512.
Non-Final Rejection issued on Nov. 5, 2021 in U.S. Appl. No. 15/724,234.
Non-Final Rejection issued on Dec. 21, 2021 in U.S. Appl. No. 16/143,036.
Final Rejection issued on Jun. 9, 2022 in U.S. Appl. No. 16/143,036.
Final Rejection issued on Jan. 13, 2022 in U.S. Appl. No. 15/791,249.
Non-Final Rejection issued on Mar. 1, 2022 in U.S. Appl. No. 16/143,678.
Non-Final Rejection issued on Feb. 4, 2022 in U.S. Appl. No. 16/143,821.
English Translation of Office Action issued on Jan. 6, 2022 in CN Application No. 201780037588.X.
English Translation of Office Action issued on Jan. 6, 2022 in CN Application No. 201780037587.5.
English Translation of Final Rejection issued on Jun. 30, 2022 in CN Application No. 201780037587.5.

(56) References Cited

OTHER PUBLICATIONS

U.S. Appl. No. 11/092,217, filed Mar. 29, 2005.
U.S. Appl. No. 11/237,525, filed Sep. 28, 2005.
U.S. Appl. No. 11/473,356, filed Jun. 22, 2006.
U.S. Appl. No. 11/517,982, filed Sep. 8, 2006.
U.S. Appl. No. 11/526,996, filed Sep. 26, 2006.
U.S. Appl. No. 11/634,280, filed Dec. 5, 2006.
U.S. Appl. No. 11/639,013, filed Dec. 14, 2006.
U.S. Appl. No. 11/674,223, filed Feb. 13, 2007.
U.S. Appl. No. 11/775,484, filed Jul. 10, 2007.
U.S. Appl. No. 12/102,071, filed Apr. 14, 2008.
U.S. Appl. No. 12/128,950, filed May 29, 2008.
U.S. Appl. No. 12/107,389, filed Apr. 22, 2008.
U.S. Appl. No. 12/171,692, filed Jul. 11, 2008.
U.S. Appl. No. 12/411,505, filed Mar. 26, 2009.
U.S. Appl. No. 12/411,835, filed Mar. 26, 2009.
U.S. Appl. No. 12/575,261, filed Oct. 7, 2009.
U.S. Appl. No. 12/614,928, filed Nov. 9, 2009.
U.S. Appl. No. 12/779,316, filed May 13, 2010.
U.S. Appl. No. 13/035,328, filed Feb. 25, 2011.
U.S. Appl. No. 13/052,655, filed Mar. 21, 2011.
U.S. Appl. No. 13/342,614, filed Feb. 12, 2012.
U.S. Appl. No. 13/096,996, filed Apr. 28, 2011.
U.S. Appl. No. 13/853,237, filed Mar. 29, 2013.
U.S. Appl. No. 13/853,223, filed Mar. 29, 2013.
U.S. Appl. No. 13/853,253, filed Mar. 29, 2013.
U.S. Appl. No. 13/853,276, filed Mar. 29, 2013.
U.S. Appl. No. 13/853,290, filed Mar. 29, 2013.
U.S. Appl. No. 13/890,542, filed May 9, 2013.
U.S. Appl. No. 13/974,376, filed Aug. 23, 2013.
U.S. Appl. No. 13/974,389, filed Aug. 23, 2013.
U.S. Appl. No. 13/974,401, filed Aug. 23, 2013.
U.S. Appl. No. 13/974,413, filed Aug. 23, 2013.
U.S. Appl. No. 14/032,588, filed Sep. 20, 2013.
U.S. Appl. No. 14/195,362, filed Mar. 3, 2014.
U.S. Appl. No. 14/284,019, filed May 21, 2014.
U.S. Appl. No. 14/492,874, filed Sep. 22, 2014.
U.S. Appl. No. 14/572, 173, filed Dec. 16, 2014.
U.S. Appl. No. 14/599,803, filed Jan. 19, 2015.
U.S. Appl. No. 14/844,810, filed Sep. 3, 2015.
U.S. Appl. No. 14/945, 181, filed Nov. 18, 2015.
U.S. Appl. No. 14/980,836, filed Dec. 28, 2015.
U.S. Appl. No. 15/058,056, filed Mar. 1, 2016.
U.S. Appl. No. 15/144, 191, filed May 2, 2016.
U.S. Appl. No. 15/398,398, filed Jan. 4, 2017.
U.S. Appl. No. 15/342,448, filed Nov. 3, 2016.
U.S. Appl. No. 15/438,406, filed Feb. 21, 2017.
U.S. Appl. No. 15/438,458, filed Feb. 21, 2017.
U.S. Appl. No. 15/634,776, filed Jun. 27, 2017.
U.S. Appl. No. 15/672,228, filed Aug. 8, 2017.
PCT/US02/32542, Oct. 11, 2002.

* cited by examiner ns ENHANCED DELIVERY EPINEPHRINE
COMPOSITIONS

CLAIM OF PRIORITY

This application is a continuation of U.S. patent application Ser. No. 17/514,805, filed Oct. 29, 2021, which is a continuation of U.S. patent application Ser. No. 15/587,364, filed May 4, 2017, now U.S. Pat. No. 11,191,737, which claims priority under 35 U.S.C. § 119(e) to U.S. Patent Application Ser. No. 62/331,996 filed on May 5, 2016, each of which is hereby incorporated by reference in its entirety.

TECHNICAL FIELD

This invention relates to pharmaceutical compositions.

BACKGROUND

Active ingredients, such as drugs or pharmaceuticals, are delivered to patients in deliberate fashion. Delivery of drugs or pharmaceuticals using film transdermally or transmucosally can require that the drug or pharmaceutical permeate or otherwise cross a biological membrane in an effective and efficient manner.

SUMMARY

In general a pharmaceutical composition can include a polymeric matrix, epinephrine in the polymeric matrix, and an adrenergic receptor interacter. In certain embodiments, the pharmaceutical composition can further include a permeation enhancer. In certain embodiments, an adrenergic receptor interacter can be an adrenergic receptor blocker. In some embodiments, the adrenergic receptor interacter can also be a flavonoid, or used in combination with a flavonoid.

In certain embodiments, the adrenergic receptor interacter can be a terpenoid, terpene or a C3-C22 alcohol or acid. The adrenergic receptor interacter can be a sesquiterpene. In certain embodiments, the adrenergic receptor interacter can include farnesol, linoleic acid, arachidonic acid, docosahexanoic acid, eicosapentanoic acid, or docosapentanoic acid, or combinations thereof.

In certain embodiments, the pharmaceutical composition can be a film further comprising a polymeric matrix, the pharmaceutically active component being contained in the polymeric matrix.

In certain embodiments, the adrenergic receptor interacter can be a phytoextract.

In certain embodiments, the permeation enhancer can be a phytoextract.

In certain embodiments, the permeation enhancer can include a phenylpropanoid.

In certain embodiments, the pharmaceutical composition can include a fungal extract.

In certain embodiments, the pharmaceutical composition can include saturated or unsaturated alcohol.

In certain embodiments, the alcohol can be benzyl alcohol.

In some cases, the flavonoid, phytoextract, phenylpropanoid, eugenol, or fungal extract can be used as a solubilizer.

In certain embodiments, the phenylpropanoid can be eugenol. In other embodiments, the phenylpropanoid can be eugenol acetate. In certain embodiments, the phenylpropanoid can be a cinnamic acid. In other embodiments, the phenylpropanoid can be a cinnamic acid ester. In other embodiments, phenylpropanoid can be a cinnamic aldehyde.

In other embodiments, the phenylpropanoid can be a hydrocinnamic acid. In certain embodiments, the phenylpropanoid can be chavicol. In other embodiments, the phenylpropanoid can be safrole.

In certain embodiments, the phytoextract can be an essential oil extract of a clove plant. In other examples, the phytoextract can be an essential oil extract of a leaf of a clove plant. The phytoextract can be an essential oil extract of a flower bud of a clove plant. In other embodiments, the phytoextract can be an essential oil extract of a stem of a clove plant.

In certain embodiments, the phytoextract can be synthetic.

In certain embodiments, the phytoextract can include 20-95% eugenol, including 40-95% eugenol, and including 60-95% eugenol. In certain embodiments, the phytoextract can include 80-95% eugenol.

In certain embodiments, the polymer matrix can include a polymer. The polymer can include a water soluble polymer.

In certain embodiments, the polymer can be a polyethylene oxide.

In certain embodiments, the polymer can be a cellulosic polymer. In certain embodiments, the cellulosic polymer can be hydroxypropylmethyl cellulose, hydroxyethyl cellulose, hydroxyethylmethyl cellulose, hydroxypropyl cellulose, methylcellulose, carboxymethyl cellulose and/or sodium carboxymethylcellulose.

In certain embodiments, the polymer can include hydroxypropyl methylcellulose.

In certain embodiments, the polymer can include polyethylene oxide and hydroxypropyl methylcellulose.

In certain embodiments, the polymer can include polyethylene oxide and/or polyvinyl pyrrolidone.

In certain embodiments, the polymeric matrix can include polyethylene oxide and/or a polysaccharide.

In certain embodiments, the polymeric matrix can include polyethylene oxide, hydroxypropyl methylcellulose and/or a polysaccharide.

In certain embodiments, the polymeric matrix can include polyethylene oxide, a cellulosic polymer, polysaccharide and/or polyvinylpyrrolidone.

In certain embodiments, the polymeric matrix can include at least one polymer selected from the group of: pullulan, polyvinyl pyrrolidone, polyvinyl alcohol, sodium alginate, polyethylene glycol, xanthan gum, tragacanth gum, guar gum, acacia gum, arabic gum, polyacrylic acid, methylmethacrylate copolymer, carboxyvinyl copolymers, starch, gelatin, ethylene oxide, propylene oxide co-polymers, collagen, albumin, poly-amino acids, polyphosphazenes, polysaccharides, chitin, chitosan, and derivatives thereof.

In certain embodiments, the pharmaceutical composition can further include a stabilizer. Stabilizers can include antioxidants, which can prevent unwanted oxidation of materials, sequestrants, which can form chelate complexes and inactivating traces of metal ions that would otherwise act as catalysts, emulsifiers and surfactants, which can stabilize emulsions, ultraviolet stabilizers, which can protect materials from harmful effects of ultraviolet radiation, UV absorbers, chemicals absorbing ultraviolet radiation and preventing it from penetrating the composition, quenchers, which can dissipate the radiation energy as heat instead of letting it break chemical bonds, or scavengers which can eliminate free radicals formed by ultraviolet radiation.

In yet another aspect, the pharmaceutical composition has a suitable nontoxic, nonionic alkyl glycoside having a hydrophobic alkyl group joined by a linkage to a hydrophilic saccharide in combination with a mucosal delivery-enhancing agent selected from: (a) an aggregation inhibitory agent; (b) a charge-modifying agent; (c) a pH control agent; (d) a degradative enzyme inhibitory agent; (e) a mucolytic or mucus cleaning agent; (f) a ciliostatic agent; (g) a membrane penetration-enhancing agent selected from: (i) a surfactant; (ii) a bile salt; (ii) a phospholipid additive, mixed micelle, liposome, or carrier; (iii) an alcohol; (iv) an enamine; (v) a nitric oxide donor compound; (vi) a long chain amphipathic molecule; (vii) a small hydrophobic penetration enhancer; (viii) sodium or a salicylic acid derivative; (ix) a glycerol ester of acetoacetic acid; (x) a cyclodextrin or beta-cyclodextrin derivative; (xi) a medium-chain fatty acid; (xii) a chelating agent; (xiii) an amino acid or salt thereof; (xiv) an N-acetylamino acid or salt thereof; (xv) an enzyme degradative to a selected membrane component; (ix) an inhibitor of fatty acid synthesis; (x) an inhibitor of cholesterol synthesis; and (xi) any combination of the membrane penetration enhancing agents recited in (i)-(x); (h) a modulatory agent of epithelial junction physiology; (i) a vasodilator agent; (j) a selective transport-enhancing agent; and (k) a stabilizing delivery vehicle, carrier, mucoadhesive, support or complex-forming species with which the compound is effectively combined, associated, contained, encapsulated or bound resulting in stabilization of the compound for enhanced mucosal delivery, wherein the formulation of the compound with the transmucosal delivery-enhancing agents provides for increased bioavailability of the compound in a blood plasma of a subject.

In general a method of making a pharmaceutical composition can include combining an adrenergic receptor interacter with a pharmaceutically active component including epinephrine and forming a pharmaceutical composition including the adrenergic receptor interacter and the pharmaceutically active component.

In general, a pharmaceutical composition can be dispensed from a device. A device can include a housing that holds an amount of a pharmaceutical composition, including a polymeric matrix; a pharmaceutically active component including epinephrine in the polymeric matrix; and an adrenergic receptor interacter; and an opening that dispenses a predetermined amount, such as a predetermined dose, of the pharmaceutical composition. The device can also dispense a pharmaceutical composition including a permeation enhancer including a phenylpropanoid and/or a phytoextract.

Other aspects, embodiments, and features will be apparent from the following description, the drawings, and the claims.

BRIEF DESCRIPTION OF THE FIGURES

Referring to FIG. 2A, this graph shows average amount of active material permeated vs. time, with 8.00 mg/mL epinephrine bitartrate and 4.4 mg/mL epinephrine base solubilized.

Referring to FIG. 28, this graph shows average flux vs. time, with 8.00 mg/mL epinephrine bitartrate and 4.4 mg/mL epinephrine base solubilized.

DETAILED DESCRIPTION

Figure 1A:
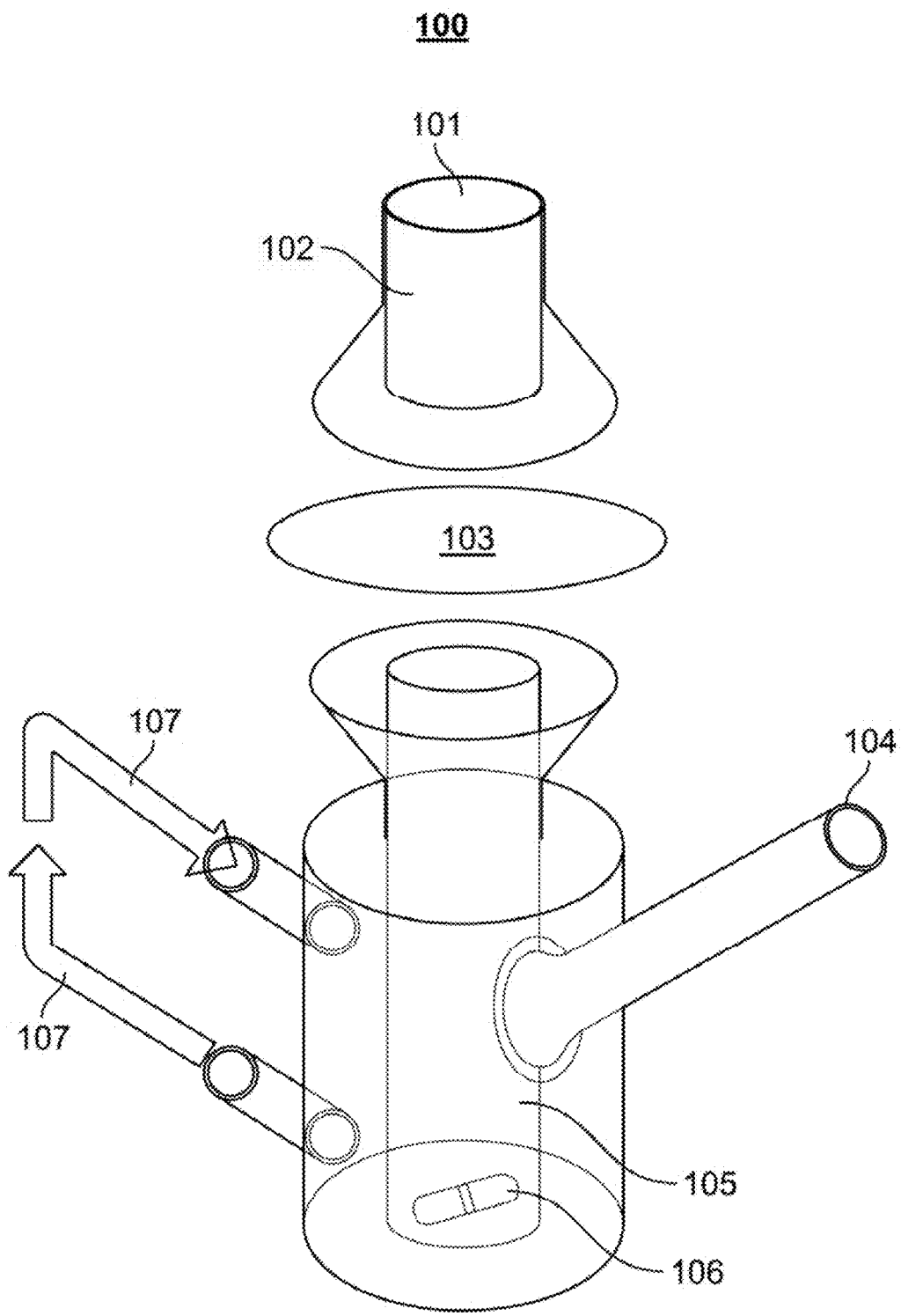
Referring to FIG. 1A, a Franz diffusion cell 100 includes a donor compound 101, a donor chamber 102, a membrane 103, sampling port 104, receptor chamber 105, stir bar 106, and a heater/circulator 107.

Mucosal surfaces, such as the oral mucosa, are a convenient route for delivering drugs to the body due to the fact that they are highly vascularized and permeable, providing increased bioavailability and rapid onset of action because it does not pass through the digestive system and thereby avoids first pass metabolism. In particular, the buccal and sublingual tissues offer advantageous sites for drug delivery because they are highly permeable regions of the oral mucosa, allowing drugs diffusing from the oral mucosa to have direct access to systemic circulation. This also offers increased convenience and therefore increased compliance in patients. For certain drugs, or pharmaceutically active components, a permeation enhancer can help to overcome the mucosal barrier and improve permeability. Permeation enhancers reversibly modulate the penetrability of the barrier layer in favor of drug absorption. Permeation enhancers facilitate transport of molecules through the epithelium. Absorption profiles and their rates can be controlled and modulated by a variety of parameters, such as but not limited to film size, drug loading, enhancer type/loading, polymer matrix release rate and mucosal residence time.

A pharmaceutical composition can be designed to deliver a pharmaceutically active component in a deliberate and tailored way. However, solubility and permeability of the pharmaceutically active component in vivo, in particular, in the mouth of a subject, can vary tremendously. A particular class of permeation enhancer can improve the uptake and bioavailability of the pharmaceutically active component in vivo. In particular, when delivered to the mouth via a film, the permeation enhancer can improve the permeability of the pharmaceutically active component through the mucosa and into the blood stream of the subject. The permeation enhancer can improve absorption rate and amount of the pharmaceutically active component by more than 5%, more than 10%, more than 20%, more than 30%, more than 40%, more than 50%, more than 60%, more than 70%, more than 80%, more than 90%, more than 100%, more than 150%, about 200% or more. or less than 200%, less than 150%, less than 100%, less than 90%, less than 80%, less than 70%, less than 60%, less than 50%, less than 40%, less than 30%, less than 20%, less than 10%, or less than 5%, or a combination of these ranges, depending on the other components in the composition.

In certain embodiments, a pharmaceutical composition has a suitable nontoxic, nonionic alkyl glycoside having a hydrophobic alkyl group joined by a linkage to a hydrophilic saccharide in combination with a mucosal delivery-enhancing agent selected from: (a) an aggregation inhibitory agent; (b) a charge-modifying agent; (c) a pH control agent; (d) a degradative enzyme inhibitory agent; (e) a mucolytic or mucus cleaning agent; (f) a ciliostatic agent; (g) a membrane penetration-enhancing agent selected from: (i) a surfactant; (ii) a bile salt; (ii) a phospholipid additive, mixed micelle, liposome, or carrier; (iii) an alcohol; (iv) an enamine; (v) an NO donor compound; (vi) a long chain amphipathic molecule; (vii) a small hydrophobic penetration enhancer; (viii) sodium or a salicylic acid derivative; (ix) a glycerol ester of acetoacetic acid; (x) a cyclodextrin or beta-cyclodextrin derivative; (xi) a medium-chain fatty acid; (xii) a chelating agent; (xiii) an amino acid or salt thereof, (xiv) an N-acetylamino acid or salt thereof; (xv) an enzyme degradative to a selected membrane component; (ix) an inhibitor of fatty acid synthesis; (x) an inhibitor of cholesterol synthesis; and (xi) any combination of the membrane penetration enhancing agents recited in (i)-(x); (h) a modulatory agent of epithelial junction physiology; (i) a vasodilator agent; (j) a selective transport-enhancing agent; and (k) a stabilizing delivery vehicle, carrier, mucoadhesive, support or complex-forming species with which the compound is effectively combined, associated, contained, encapsulated or bound resulting in stabilization of the compound for enhanced transmucosal delivery, wherein the formulation of the compound with the transmucosal delivery-enhancing agents provides for increased bioavailability of the compound in blood plasma of a subject. Penetration enhancers have been described in J. Nicolazzo, et al., *J. of Controlled Disease*, 105 (2005) 1-15, which is incorporated by reference herein.

There are many reasons why the oral mucosa might be an attractive site for the delivery of therapeutic agents into the systemic circulation. Due to the direct drainage of blood from the buccal epithelium into the internal jugular vein first-pass metabolism in the liver and intestine may be avoided. First-pass effect can be a major reason for the poor bioavailability of some compounds when administered orally. Additionally, the mucosa lining the oral cavity is easily accessible, which ensures that a dosage form can be applied to the required site and can be removed easily in the case of an emergency. However, like the skin, the buccal mucosa acts as a barrier to the absorption of xenobiotics, which can hinder the permeation of compounds across this tissue. Consequently, the identification of safe and effective penetration enhancers has become a major goal in the quest to improve oral mucosal drug delivery.

Chemical penetration enhancers are substances that control the permeation rate of a coadministered drug through a biological membrane. While extensive research has focused on obtaining an improved understanding of how penetration enhancers might alter intestinal and transdermal permeability, far less is known about the mechanisms involved in buccal and sublingual penetration enhancement.

The buccal mucosa delineates the inside lining of the cheek as well as the area between the gums and upper and lower lips and it has an average surface area of 100 $cm^2$. The surface of the buccal mucosa consists of a stratified squamous epithelium which is separated from the underlying connective tissue (lamina propria and submucosa) by an undulating basement membrane (a continuous layer of extracellular material approximately 1-2 µm in thickness). This stratified squamous epithelium consists of differentiating layers of cells which change in size, shape, and content as they travel from the basal region to the superficial region, where the cells are shed. There are approximately 40-50 cell layers, resulting in a buccal mucosa which is 500-600 µm thick.

Structurally the sublingual mucosa is comparable to the buccal mucosa but the thickness of this epithelium is 100-200 µm. This membrane is also non-keratinised and being relatively thinner has been demonstrated to be more permeable than buccal mucosa. Blood flow to the sublingual mucosal is slower compared with the buccal mucosa and is of the order of 1.0 ml/min-1/cm-2.

The permeability of the buccal mucosa is greater than that of the skin, but less than that of the intestine. The differences in permeability are the result of structural differences between each of the tissues. The absence of organized lipid lamellae in the intercellular spaces of the buccal mucosa results in greater permeability of exogenous compounds, compared to keratinized epithelia of the skin; while the increased thickness and lack of tight junctions results in the buccal mucosa being less permeable than intestinal tissue.

The primary barrier properties of the buccal mucosa have been attributed to the upper one-third to one-quarter of the buccal epithelium. Researchers have learned that beyond the surface epithelium, the permeability barrier of nonkeratinized oral mucosa could also be attributed to contents extruded from the membrane-coating granules into the epithelial intercellular spaces.

The intercellular lipids of the nonkeratinized regions of the oral cavity are of a more polar nature than the lipids of the epidermis, palate, and gingiva, and this difference in the chemical nature of the lipids may contribute to the differences in permeability observed between these tissues. Consequently, it appears that it is not only the greater degree of intercellular lipid packing in the stratum corneum of keratinized epithelia that creates a more effective barrier, but also the chemical nature of the lipids present within that barrier.

The existence of hydrophilic and lipophilic regions in the oral mucosa has led researchers to postulate the existence of two routes of drug transport through the buccal mucosa paracellular (between the cells) and transcellular (across the cells).

Since drug delivery through the buccal mucosa is limited by the barrier nature of the epithelium and the area available for absorption, various enhancement strategies are required in order to deliver therapeutically relevant amounts of drug to the systemic circulation. Various methods, including the use of chemical penetration enhancers, prodrugs, and physical methods may be employed to overcome the barrier properties of the buccal mucosa.

A chemical penetration enhancer, or absorption promoter, is a substance added to a pharmaceutical formulation in order to increase the membrane permeation or absorption rate of the coadministered drug, without damaging the membrane and/or causing toxicity. There have been many studies investigating the effect of chemical penetration enhancers on the delivery of compounds across the skin, nasal mucosa, and intestine. In recent years, more attention has been given to the effect of these agents on the permeability of the buccal mucosa. Since permeability across the buccal mucosa is considered to be a passive diffusion process the steady state flux (Jss) should increase with increasing donor chamber concentration (CD) according to Fick's first law of diffusion.

Surfactants and bile salts have been shown to enhance the permeability of various compounds across the buccal mucosa, both in vitro and in vivo. The data obtained from these studies strongly suggest that the enhancement in permeability is due to an effect of the surfactants on the mucosal intercellular lipids.

Fatty acids have been shown to enhance the permeation of a number of drugs through the skin, and this has been shown by differential scanning calorimetry and Fourier transform infrared spectroscopy to be related to an increase in the fluidity of intercellular lipids.

Additionally, pretreatment with ethanol has been shown to enhance the permeability of tritiated water and albumin across ventral tongue mucosa, and to enhance caffeine permeability across porcine buccal mucosa. There are also several reports of the enhancing effect of Azone® on the permeability of compounds through oral mucosa. Further, chitosan, a biocompatible and biodegradable polymer, has been shown to enhance drug delivery through various tissues, including the intestine and nasal mucosa.

Oral transmucosal drug delivery (OTDD) is the administration of pharmaceutically active agents through the oral mucosa to achieve systemic effects. Permeation pathways and predictive models for OTDD are described, e.g. in M. Sattar, Oral transmucosal drug delivery—Current status and future prospects, *Int'l. Journal of Pharmaceutics,* 47(2014) 498-506, which is incorporated by reference herein. OTDD continues to attract the attention of academic and industrial scientists. Despite limited characterization of the permeation pathways in the oral cavity compared with skin and nasal routes of delivery, recent advances in our understanding of the extent to which ionized molecules permeate the buccal epithelium, as well as the emergence of new analytical techniques to study the oral cavity, and the progressing development of in silico models predictive of buccal and sublingual permeation, prospects are encouraging.

In order to deliver broader classes of drugs across the buccal mucosa, reversible methods of reducing the barrier potential of this tissue should be employed. This requisite has fostered the study of penetration enhancers that will safely alter the permeability restrictions of the buccal mucosa. It has been shown that buccal penetration can be improved by using various classes of transmucosal and transdermal penetration enhancers such as bile salts, surfactants, fatty acids and their derivatives, chelators, cyclodextrins and chitosan. Among these chemicals used for the drug permeation enhancement, bile salts are the most common.

In vitro studies on enhancing effect of bile salts on the buccal permeation of compounds is discussed in Sevda Senel, Drug permeation enhancement via buccal route: possibilities and limitations, *Journal of Controlled Release* 72 (2001) 133-144, which is incorporated by reference herein. That article also discusses recent studies on the effects of buccal epithelial permeability of dihydroxy bile salts, sodium glycodeoxycholate (SGDC) and sodium taurodeoxycholate (TDC) and tri-hydroxy bile salts, sodium glycocholate (GC) and sodium taurocholate (TC) at 100 mM concentration including permeability changes correlated with the histological effects. Fluorescein isothiocyanate (FITC), morphine sulfate were each used as the model compound.

Chitosan has also been shown to promote absorption of small polar molecules and peptide/protein drugs through nasal mucosa in animal models and human volunteers. Other studies have shown an enhancing effect on penetration of compounds across the intestinal mucosa and cultured Caco-2 cells.

The permeation enhancer can be a phytoextract. A phytoextract can be an essential oil or composition including essential oils extracted by distillation of the plant material. In certain circumstances, the phytoextract can include synthetic analogues of the compounds extracted from the plant material (i.e., compounds made by organic synthesis). The phytoextract can include a phenylpropanoid, for example, phenyl alanine, eugenol, eugenol acetate, a cinnamic acid, a cinnamic acid ester, a cinnamic aldehyde, a hydrocinnamic acid, chavicol, or safrole, or a combination thereof. The phytoextract can be an essential oil extract of a clove plant, for example, from the leaf, stem or flower bud of a clove plant. The clove plant can be *Syzygium aromaticum*. The phytoextract can include 20-95% eugenol, including 40-95% eugenol, including 60-95% eugenol, and for example, 80-95% eugenol. The extract can also include 5% to 15% eugenol acetate. The extract can also include caryophyllene. The extract can also include up to 2.1% α-humulen. Other volatile compounds included in lower concentrations in clove essential oil can be β-pinene, limonene, farnesol, benzaldehyde, 2-heptanone and ethyl hexanoate. Other permeation enhancers may be added to the composition to improve absorption of the drug. Suitable permeation enhancers include natural or synthetic bile salts such as sodium fusidate; glycocholate or deoxycholate and their salts; fatty acids and derivatives such as sodium laurate, oleic acid, oleyl alcohol, monoolein, and palmitoylcarnitine; chelators such as disodium EDTA, sodium citrate and sodium laurylsulfate, azone, sodium cholate, sodium 5-methoxysalicylate, sorbitan laurate, glyceryl monolaurate, octoxynonyl-9, laureth-9, polysorbates, sterols, or glycerides, such as caprylocaproyl polyoxylglycerides, e.g., Labrasol. The permeation enhancer can include phytoextract derivatives and/or monolignols. The permeation enhancer can also be a fungal extract.

Some natural products of plant origin have been known to have a vasodilatory effect. For review, see McNeill J. R. and Jurgens, T. M., Can. J. Physiol. Pharmacol. 84:803-821 (2006), which is incorporated by reference herein. Specifically, vasorelaxant effects of eugenol have been reported in a number of animal studies. See, e.g., Lahlou, S., et al., J. Cardiovasc. Pharmacol. 43:250-57 (2004), Damiani, C. E. N., et al., Vascular Pharmacol. 40:59-66 (2003), Nishijima, H., et al., Japanese J. Pharmacol. 79:327-334 (1998), and Hume W. R., J. Dent Res. 62(9):1013-15 (1983), each of which is incorporated by reference herein. Calcium channel blockade was suggested to be responsible for vascular relaxation induced by a plant essential oil, or its main constituent, eugenol. See, Interaminense L.R.L. et al., Fundamental & Clin. Pharmacol. 21: 497-506 (2007), incorporated by reference herein.

Fatty acids can be used as inactive ingredients in drug preparations or drug vehicles. Fatty acids can also be used as formulation ingredients due to their certain functional effects and their biocompatible nature. Fatty acid, both ti-ee and as part of complex lipids, are major metabolic fuel (storage and transport energy), essential components of all membranes and gene regulators. For review, see Rustan A. C. and Drevon, C. A., Fatty Acids: Structures and Properties, Encyclopedia of Life Sciences (2005), which is incorporated by reference herein. There are two families of essential fatty acids that are metabolized in the human body: ω-3 and ω-6 polyunsaturated fatty acids (PUFAs). If the first double bond is found between the third and the fourth carbon atom from the ω carbon, they are called ω-3 fatty acids. If the first double bond is between the sixth and seventh carbon atom, they are called ω-6 fatty acids. PUFAs are further metabolized in the body by the addition of carbon atoms and by desaturation (extraction of hydrogen). Linoleic acid, which is a ω-6 fatty acid, is metabolized to γ-linolenic acid, dihomo-γ-linolinic acid, arachidonic acid, adrenic acid, tetracosatetraenoic acid, tetracosapentaenoic acid and docosapentaenoic acid. α-linolenic acid, which is a ω-3 fatty acid is metabolized to octadecatetraenoic acid, eicosatetraenoic acid, eicosapentaenoic acid (EPA), docosapentaenoic acid, tetracosapentaenoic acid, tetracosahexaenoic acid and docosahexaenoic acid (DHA).

It has been reported that fatty acids, such as palmitic acid, oleic acid, linoleic acid and eicosapentaenoic acid, induced relaxation and hyperpolarization of porcine coronary artery smooth muscle cells via a mechanism involving activation of the $Na^+K^+$-APTase pump and the fatty acids with increasing degrees of cis-unsaturation had higher potencies. See, Pomposiello, S. I. et al., Hypertension 31:615-20 (1998), which is incorporated by reference herein. Interestingly, the pulmonary vascular response to arachidonic acid, a metabolite of linoleic acid, can be either vasoconstrictive or vasodilative, depending on the dose, animal species, the mode of arachidonic acid administration, and the tones of the pulmonary circulation. For example, arachidonic acid has been reported to cause cyclooxygenase-dependent and -independent pulmonary vasodilation. See, Feddersen, C. O. et al., J. Appl. Physiol. 68(5):1799-808 (1990); and see, Spannhake, E. W., et al., J. Appl. Physiol. 44:397-495 (1978) and Wicks, T. C. et al., Circ. Res. 38:167-71 (1976), each of which is incorporated by reference herein.

Many studies have reported effects of EPA and DHA on vascular reactivity after being administered as ingestible forms. Some studies found that EPA-DHA or EPA alone suppressed the vasoconstrictive effect of norepinephrine or increased vasodilatory responses to acetylcholine in the forearm microcirculation. See, Chin, J. P. F, et al., Hypertension 21:22-8 (1993), and Tagawa, H. et al., J Cardiovasc Pharmacol 33:633-40 (1999), each of which is incorporated by reference herein. Another study found that both EPA and DHA increased systemic arterial compliance and tended to reduce pulse pressure and total vascular resistance. See, Nestel, P. et al., Am J. Clin. Nutr. 76:326-30 (2002), which is incorporated by reference herein. Meanwhile, a study found that DHA, but not EPA, enhanced vasodilator mechanisms and attenuates constrictor responses in forearm microcirculation in hyperlipidemic overweight men. See, Mori, T. A., et al., Circulation 102:1264-69 (2000), which is incorporated by reference herein. Another study found vasodilator effects of DHA on the rhythmic contractions of isolated human coronary arteries in vitro. See Wu, K.-T. et al., Chinese J. Physiol. 50(4):164-70 (2007), which is incorporated by reference herein.

The adrenergic receptors (or adrenoceptors) are a class of G protein-coupled receptors that are a target of catecholamines, especially norepinephrine (noradrenaline) and epinephrine (adrenaline). Epinephrine (adrenaline) interacts with both α- and β-adrenoceptors, causing vasoconstriction and vasodilation, respectively. Although α receptors are less sensitive to epinephrine, when activated, they override the vasodilation mediated by α-adrenoceptors because there are more peripheral α1 receptors than β-adrenoceptors. The result is that high levels of circulating epinephrine cause vasoconstriction. At lower levels of circulating epinephrine, β-adrenoceptor stimulation dominates, producing vasodilation followed by decrease of peripheral vascular resistance. The α1-adrenoreceptor is known for smooth muscle contraction, mydriasis, vasoconstriction in the skin, mucosa and abdominal vicera and sphincter contraction of the gastrointestinal (GI) tract and urinary bladder. The α1-adrenergic receptors are member of the $G_q$ protein-coupled receptor superfamily. Upon activation, a heterotrimeric G protein, $G_q$, activates phospholipase C (PLC). The mechanism of action involves interaction with calcium channels and changing the calcium content in a cell. For review, see Smith R. S. et al., Journal of Neurophysiology 102(2): 1103-14 (2009), which is incorporated by reference herein. Many cells possess these receptors.

α1-adrenergic receptors can be a main receptor for fatty acids. For example, saw palmetto extract (SPE), widely used for the treatment of benign prostatic hyperplasia (BPH), has been reported to bind α1-adrenergic, muscarinic and 1,4-dihydropyridine (1,4-DHP) calcium channel antagonist receptors. See, Abe M., et al., Biol. Pharm. Bull. 32(4) 646-650 (2009), and Suzuki M. et al., Acta Pharmacologica Sinica 30:271-81 (2009), each of which is incorporated by reference herein. SPE includes a variety of fatty acids including lauric acid, oleic acid, myristic acid, palmitic acid and linoleic acid. Lauric acid and oleic acid can bind noncompetitively to α1-adrenergic, muscarinic and 1,4-DHP calcium channel antagonist receptors.

In certain embodiments, a permeation enhancer can be an adrenergic receptor interacter. An adrenergic receptor interacter refers to a compound or substance that modifies and/or otherwise alters the action of an adrenergic receptor. For example, an adrenergic receptor interacter can prevent stimulation of the receptor by increasing, or decreasing their ability to bind. Such interacters can be provided in either short-acting or long-acting forms. Certain short-acting interacters can work quickly, but their effects last only a few hours. Certain long-acting interacters can take longer to work, but their effects can last longer. The interacter can be selected and/or designed based on, e.g., on one or more of the desired delivery and dose, active pharmaceutical ingredient, permeation modifier, permeation enhancer, matrix, and the condition being treated. An adrenergic receptor interacter can be an adrenergic receptor blocker. The adrenergic receptor interacter can be a terpene (e.g. volatile unsaturated hydrocarbons found in the essential oils of plants, derived from units of isoprenes) or a C3-C22 alcohol or acid, preferably a C7-C18 alcohol or acid. In certain embodiments, the adrenergic receptor interacter can include farnesol, linoleic acid, arachidonic acid, docosahexanoic acid, eicosapentanoic acid, and/or docosapentanoic acid. The acid can be a carboxylic acid, phosphoric acid, sulfuric acid, hydroxamic acid, or derivatives thereof. The derivative can be an ester or amide. For example, the adrenergic receptor interacter can be a fatty acid or fatty alcohol.

The C3-C22 alcohol or acid can be an alcohol or acid having a straight C3-C22 hydrocarbon chain, for example a C3-C22 hydrocarbon chain optionally containing at least one double bond, at least one triple bond, or at least one double bond and one triple bond; said hydrocarbon chain being optionally substituted with $C_{1-4}$ alkyl, $C_{2-4}$ alkenyl, $C_{2-4}$ alkynyl, $C_{1-4}$ alkoxy, hydroxyl, halo, amino, nitro, cyano, $C_{3-5}$ cycloalkyl, 3-5 membered heterocycloalkyl, monocyclic aryl, 5-6 membered heteroaryl, $C_{1-4}$ alkylcarbonyloxy, $C_{1-4}$ alkyloxycarbonyl, $C_{1-4}$ alkylcarbonyl, or formyl; and further being optionally interrupted by —O—, —N($R^a$)—, —N($R^a$)—C(O)—O—, —O—C(O)—N($R^b$)—, —N($R^a$)—C(O)—N($R^b$)—, or —O—C(O)—O—. Each of $R^a$ and $R^b$, independently, is hydrogen, alkyl, alkenyl, alkynyl, alkoxy, hydroxylalkyl, hydroxyl, or haloalkyl.

Fatty acids with a higher degree of unsaturation are effective candidates to enhance the permeation of drugs. Unsaturated fatty acids showed higher enhancement than saturated fatty acids, and the enhancement increased with the number of double bonds. See, A. Mittal, et al. Status of Fatty Acids as Skin Penetration Enhancers—A Review, *Current Drug Delivery*, 2009, 6. pp. 274-279, which is incorporated by reference herein. Position of double bond also affects the enhancing activity of fatty acids. Differences in the physicochemical properties of fatty acid which originate from differences in the double bond position most likely determine the efficacy of these compounds as skin penetration enhancers. Skin distribution increases as the position of the double bond is shifted towards the hydrophilic end. It has also been reported that fatty acid which has a double bond at an even number position more rapidly effects the perturbation of the structure of both the stratum corneum and the dermis than a fatty acid which has double bond at an odd number position. Cis-unsaturation in the chain can tend to increase activity.

An adrenergic receptor interacter can be a terpene. Hypotensive activity of terpenes in essential oils has been reported. See, Menezes I. A. et al., Z. Naturforsch. 65c:652-66 (2010), which is incorporated by reference herein. In certain embodiments, the permeation enhancer can be a sesquiterpene. Sesquiterpenes are a class of terpenes that consist of three isoprene units and have the empirical formula $C_{15}H_{24}$. Like monoterpenes, sesquiterpenes may be acyclic or contain rings, including many unique combinations. Biochemical modifications such as oxidation or rearrangement produce the related sesquiterpenoids.

An adrenergic receptor interacter can be an unsaturated fatty acid such as linoleic acid. In certain embodiments, the permeation enhancer can be farnesol. Farnesol is a 15-carbon organic compound which is an acyclic sesquiterpene alcohol, which is a natural dephosphorylated form of farnesyl pyrophosphate. Under standard conditions, it is a colorless liquid. It is hydrophobic, and thus insoluble in water, but miscible with oils. Farnesol can be extracted from oils of plants such as citronella, neroli, cyclamen, and tuberose. It is an intermediate step in the biological synthesis of cholesterol from mevalonic acid in vertebrates. It has a delicate floral or weak citrus-lime odor and is used in perfumes and flavors. It has been reported that farnesol selectively kills acute myeloid leukemia blasts and leukemic cell lines in preference to primary hemopoietic cells. See, Rioja A. et al., FEBS Lett 467 (2-3): 291-5 (2000), which is incorporated by reference herein. Vasoactive properties of farnesyl analogues have been reported. See, Roullet, J.-B., et al., J. Clin. Invest., 1996, 97:2384-2390, which is incorporated by reference herein. Both Farnesol and N-acetyl-S-trans, trans-farnesyl-L-cysteine (AFC), a synthetic mimic of the carboxyl terminus of farnesylated proteins inhibited vasoconstriction in rat aortic rings.

The pharmaceutical composition can be a chewable or gelatin based dosage form, spray, gum, gel, cream, tablet, liquid or film. The composition can include textures, for example, at the surface, such as microneedles or microprotrusions. Recently, the use of micron-scale needles in increasing skin permeability has been shown to significantly increase transdermal delivery, including and especially for macromolecules. Most drug delivery studies have emphasized solid microneedles, which have been shown to increase skin permeability to a broad range of molecules and nanoparticles in vitro. In vivo studies have demonstrated delivery of oligonucleotides, reduction of blood glucose level by insulin, and induction of immune responses from protein and DNA vaccines. For such studies, needle arrays have been used to pierce holes into skin to increase transport by diffusion or iontophoresis or as drug carriers that release drug into the skin from a microneedle surface coating. Hollow microneedles have also been developed and shown to microinject insulin to diabetic rats. To address practical applications of microneedles, the ratio of microneedle fracture force to skin insertion force (i.e. margin of safety) was found to be optimal for needles with small tip radius and large wall thickness. Microneedles inserted into the skin of human subjects were reported as painless. Together, these results suggest that microneedles represent a promising technology to deliver therapeutic compounds into the skin for a range of possible applications. Using the tools of the microelectronics industry, microneedles have been fabricated with a range of sizes, shapes and materials. Microneedles can be, for example, polymeric, microscopic needles that deliver encapsulated drugs in a minimally invasive manner, but other suitable materials can be used.

Applicants have found that microneedles could be used to enhance the delivery of drugs through the oral mucosa, particularly with the claimed compositions. The microneedles create micron sized pores in the oral mucosa which can enhance the delivery of drugs across the mucosa. Solid, hollow or dissolving microneedles can be fabricated out of suitable materials including, but not limited to, metal, polymer, glass and ceramics. The microfabrication process can include photolithography, silicon etching, laser cutting, metal electroplating, metal electro polishing and molding. Microneedles could be solid which is used to pretreat the tissue and are removed before applying the film. The drug loaded polymer film described in this application can be used as the matrix material of the microneedles itself. These films can have microneedles or micro protrusions fabricated on their surface which will dissolve after forming microchannels in the mucosa through which drugs can permeate.

The term "film" can include films and sheets, in any shape, including rectangular, square, or other desired shape. A film can be any desired thickness and size. In preferred embodiments, a film can have a thickness and size such that it can be administered to a user, for example, placed into the oral cavity of the user. A film can have a relatively thin thickness of from about 0.0025 mm to about 0.250 mm, or a film can have a somewhat thicker thickness of from about 0.250 mm to about 1.0 mm. For some films, the thickness may be even larger, i.e., greater than about 1.0 mm or thinner, i.e., less than about 0.0025 mm. A film can be a single layer or a film can be multi-layered, including laminated or multiple cast films. A permeation enhancer and pharmaceutically active component can be combined in a single layer, each contained in separate layers, or can each be otherwise contained in discrete regions of the same dosage form. In certain embodiments, the pharmaceutically active component contained in the polymeric matrix can be dispersed in the matrix. In certain embodiments, the permeation enhancer being contained in the polymeric matrix can be dispersed in the matrix.

Oral dissolving films can fall into three main classes: fast dissolving, moderate dissolving and slow dissolving. Oral dissolving films can also include a combination of any of the above categories. Fast dissolving films can dissolve in about 1 second to about 30 seconds in the mouth, including more than 1 second, more than 5 seconds, more than 10 seconds, more than 20 seconds, and less than 30 seconds. Moderate dissolving films can dissolve in about 1 to about 30 minutes in the mouth including more than 1 minute, more than 5 minutes, more than 10 minutes, more than 20 minutes or less than 30 minutes, and slow dissolving films can dissolve in more than 30 minutes in the mouth. As a general trend, fast dissolving films can include (or consist of) low molecular weight hydrophilic polymers (e.g., polymers having a molecular weight between about 1,000 to 9,000 daltons, or polymers having a molecular weight up to 200,000 daltons). In contrast, slow dissolving films generally include high molecular weight polymers (e.g., having a molecular weight in millions). Moderate dissolving films can tend to fall in between the fast and slow dissolving films.

It can be preferable to use films that are moderate dissolving films. Moderate dissolving films can dissolve rather quickly, but also have a good level of mucoadhesion. Moderate dissolving films can also be flexible, quickly wettable, and are typically non-irritating to the user. Such moderate dissolving films can provide a quick enough dissolution rate, most desirably between about 1 minute and about 20 minutes, while providing an acceptable mucoadhesion level such that the film is not easily removable once it is placed in the oral cavity of the user. This can ensure delivery of a pharmaceutically active component to a user.

A pharmaceutical composition can include one or more pharmaceutically active components. The pharmaceutically active component can be a single pharmaceutical component or a combination of pharmaceutical components. The pharmaceutically active component can be an anti-inflammatory analgesic agent, a steroidal anti-inflammatory agent, an antihistamine, a local anesthetic, a bactericide, a disinfectant, a vasoconstrictor, a hemostatic, a chemotherapeutic drug, an antibiotic, a keratolytic, a cauterizing agent, an antiviral drug, an antirheumatic, an antihypertensive, a bronchodilator, an anticholinergic, an anti-anxiety drug, an anti-emetic compound, a hormone, a peptide, a protein or a vaccine. The pharmaceutically active component can be the compound, pharmaceutically acceptable salt of a drug, a prodrug, a derivative, a drug complex or analog of a drug. The term "prodrug" refers to a biologically inactive compound that can be metabolized in the body to produce a biologically active drug.

In some embodiments, more than one pharmaceutically active component may be included in the film. The pharmaceutically active components can be ace-inhibitors, anti-anginal drugs, anti-arrhythmias, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, amphetamines, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplastics, anti-parkinsonian agents, anti-rheumatic agents, appetite stimulants, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, uterine relaxants, anti-obesity drugs, erythropoietic drugs, anti-asthmatics, cough suppressants, mucolytics, DNA and genetic modifying drugs, diagnostic agents, imaging agents, dyes, or tracers, and combinations thereof.

For example, the pharmaceutically active component can be buprenorphine, naloxone, acetaminophen, riluzole, clobazam, Rizatriptan, propofol, methyl salicylate, monoglycol salicylate, aspirin, mefenamic acid, flufenamic acid, indomethacin, diclofenac, alclofenac, diclofenac sodium, ibuprofen, ketoprofen, naproxen, pranoprofen, fenoprofen, sulindac, fenclofenac, clidanac, flurbiprofen, fentiazac, bufexamac, piroxicam, phenylbutazone, oxyphenbutazone, clofezone, pentazocine, mepirizole, tiaramide hydrochloride, hydrocortisone, predonisolone, dexamethasone, triamcinolone acetonide, fluocinolone acetonide, hydrocortisone acetate, predonisolone acetate, methylpredonisolone, dexamethasone acetate, betamethasone, betamethasone valerate, flumetasone, fluorometholone, beclomethasone diproprionate, fluocinonide, diphenhydramine hydrochloride, diphenhydramine salicylate, diphenhydramine, chlorpheniramine hydrochloride, chlorpheniramine maleate isothipendyl hydrochloride, tripelennamine hydrochloride, promethazine hydrochloride, methdilazine hydrochloride dibucaine hydrochloride, dibucaine, lidocaine hydrochloride, lidocaine, benzocaine, p-buthylaminobenzoic acid 2-(die-ethylamino) ethyl ester hydrochloride, procaine hydrochloride, tetracaine, tetracaine hydrochloride, chloroprocaine hydrochloride, oxyprocaine hydrochloride, mepivacaine, cocaine hydrochloride, piperocaine hydrochloride, dyclonine, dyclonine hydrochloride, thimerosal, phenol, thymol, benzalkonium chloride, benzethonium chloride, chlorhexidine, povidone iodide, cetylpyridinium chloride, eugenol, trimethylammonium bromide, naphazoline nitrate, tetrahydrozoline hydrochloride, oxymetazoline hydrochloride, phenylephrine hydrochloride, tramazoline hydrochloride, thrombin, phytonadione, protamine sulfate, aminocaproic acid, tranexamic acid, carbazochrome, carbaxochrome sodium sulfanate, rutin, hesperidin, sulfamine, sulfathiazole, sulfadiazine, homosulfamine, sulfisoxazole, sulfisomidine, sulfamethizole, nitrofurazone, penicillin, meticillin, oxacillin, cefalotin, cefalordin, erythromycin, lincomycin, tetracycline, chlortetracycline, oxytetracycline, metacycline, chloramphenicol, kanamycin, streptomycin, gentamicin, bacitracin, cycloserine, salicylic acid, podophyllum resin, podolifox, cantharidin, chloroacetic acids, silver nitrate, protease inhibitors, thymadine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir, heparin, insulin, LHRH, TRH, interferons, oligonuclides, calcitonin, octreotide, omeprazone, fluoxetine, ethinylestradiol, amiodipine, paroxetine, enalapril, lisinopril, leuprolide, prevastatin, lovastatin, norethindrone, risperidone, olanzapine, albuterol, hydrochlorothiazide, pseudoephridrine, warfarin, terazosin, cisapride, ipratropium, busprione, methylphenidate, levothyroxine, zolpidem, levonorgestrel, glyburide, benazepril, medroxyprogesterone, clonazepam, ondansetron, losartan, quinapril, nitroglycerin, midazolam versed, cetirizine, doxazosin, glipizide, vaccine hepatitis B, salmeterol, sumatriptan, triamcinolone acetonide, goserelin, beclomethasone, granisteron, desogestrel, alprazolam, estradiol, nicotine, interferon beta IA, cromolyn, fosinopril, digoxin, fluticasone, bisoprolol, calcitril, captorpril, butorphanol, clonidine, premarin, testosterone, sumatriptan, clotrimazole, bisacodyl, dextromethorphan, nitroglycerine, nafarelin, dinoprostone, nicotine, bisacodyl, goserelin, and granisetron. In certain embodiments, the pharmaceutically active component can be epinephrine, a benzodiazepine such as diazepam or lorazepam or alprazolam.

Epinephrine Examples

In one example, a composition including epinephrine or its salts or esters can have a biodelivery profile similar to that of epinephrine administered by injection, for example, using an EpiPen. Epinephrine can be present in an amount of from about 0.01 mg to about 100 mg per dosage, for example, at a 0.1 mg, 5 mg, 10 mg, 20 mg, 30 mg, 40 mg, 50 mg, 60 mg, 70 mg, 80 mg, 90 mg or 100 mg dosage, including greater than 0.1 mg, more than 5 mg, more than 20 mg, more than 30 mg, more than 40 mg, more than 50 mg, more than 60 mg, more than 70 mg, more than 80 mg, more than 90 mg, or less than 100 mg, less than 90 mg, less than 80 mg, less than 70 mg, less than 60 mg, less than 50 mg, less than 40 mg, less than 30 mg, less than 20 mg, less than 10 mg, or less than 5 mg, or any combination thereof. In another example, a composition including diazepam can have a biodelivery profile similar to that of a diazepam tablet or gel, or better. Diazepam or its salts can be present in an amount of from about 0.5 mg to about 100 mg per dosage, for example, at a 0.5 mg, 1 mg, 5 mg, 10 mg, 20 mg, 30 mg, 40 mg, 50 mg, 60 mg, 70 mg, 80 mg, 90 mg or 100 mg dosage including greater than 1 mg, more than 5 mg, more than 20 mg, more than 30 mg, more than 40 mg, more than 50 mg, more than 60 mg, more than 70 mg, more than 80 mg, more than 90 mg, or less than 100 mg, less than 90 mg, less than 80 mg, less than 70 mg, less than 60 mg, less than 50 mg, less than 40 mg, less than 30 mg, less than 20 mg, less than 10 mg, or less than 5 mg, or any combination thereof.

In another example, a composition (e.g., including epinephrine) can have a suitable nontoxic, nonionic alkyl glycoside having a hydrophobic alkyl group joined by a linkage to a hydrophilic saccharide in combination with a mucosal delivery-enhancing agent selected from: (a) an aggregation inhibitory agent; (b) a charge-modifying agent; (c) a pH control agent; (d) a degradative enzyme inhibitory agent; (e) a mucolytic or mucus clearing agent; (f) a ciliostatic agent; (g) a membrane penetration-enhancing agent selected from: (i) a surfactant; (ii) a bile salt; (ii) a phospholipid additive, mixed micelle, liposome, or carrier, (iii) an alcohol; (iv) an enamine; (v) an NO donor compound; (vi) a long chain amphipathic molecule; (vii) a hydrophobic penetration enhancer; (viii) sodium or a salicylic acid derivative; (ix) a glycerol ester of acetoacetic acid; (x) a cyclodextrin or beta-cyclodextrin derivative; (xi) a medium-chain fatty acid; (xii) a chelating agent; (xiii) an amino acid or salt thereof; (xiv) an N-acetylamino acid or salt thereof, (xv) an enzyme degradative to a selected membrane component; (ix) an inhibitor of fatty acid synthesis; (x) an inhibitor of cholesterol synthesis; and (xi) any combination of the membrane penetration enhancing agents recited in (i)-(x); (h) a modulatory agent of epithelial junction physiology; (i) a vasodilator agent; (j) a selective transport-enhancing agent; or (k) a stabilizing delivery vehicle, carrier, mucoadhesive, support or complex-forming species with which the compound is effectively combined, associated, contained, encapsulated or bound resulting in stabilization of the compound for enhanced mucosal delivery, wherein the formulation of the compound with the transmucosal delivery-enhancing agents provides for increased bioavailability of the compound in a blood plasma of a subject. The formulation can include approximately the same active pharmaceutical ingredient (API): enhancer ratio as in the other examples for diazepam and alprazolam.

A film and/or its components can be water-soluble, water swellable or water-insoluble. The term "water-soluble" can refer to substances that are at least partially dissolvable in an aqueous solvent, including but not limited to water. The term "water-soluble" may not necessarily mean that the substance is 100% dissolvable in the aqueous solvent. The term "water-insoluble" refers to substances that are not dissolvable in an aqueous solvent, including but not limited to water. A solvent can include water, or alternatively can include other solvents (preferably, polar solvents) by themselves or in combination with water.

The composition can include a polymeric matrix. Any desired polymeric matrix may be used, provided that it is orally dissolvable or erodible. The dosage should have enough bioadhesion to not be easily removed and it should form a gel like structure when administered. They can be moderate-dissolving in the oral cavity and particularly suitable for delivery of pharmaceutically active components, although both fast release, delayed release, controlled release and sustained release compositions are also among the various embodiments contemplated.

Branched Polymers

The pharmaceutical composition film can include dendritic polymers which can include highly branched macromolecules with various structural architectures. The dendritic polymers can include dendrimers, dendronised polymers (dendrigrafted polymers), linear dendritic hybrids, multi-arm star polymers, or hyperbranched polymers.

Hyperbranched polymers are highly branched polymers with imperfections in their structure. However they can be synthesized in a single step reaction which can be an advantage over other dendritic structures and are therefore suitable for bulk volume applications. The properties of these polymers apart from their globular structure are the abundant functional groups, intramolecular cavities, low viscosity and high solubility. Dendritic polymers have been used in several drug delivery applications. See, e.g., Dendrimers as Drug Carriers: Applications in Different Routes of Drug Administration. J Pharm Sci, VOL. 97, 2008, 123-143, which is incorporated by reference herein.

The dendritic polymers can have internal cavities which can encapsulate drugs. The steric hindrance caused by the highly dense polymer chains might prevent the crystallization of the drugs. Thus, branched polymers can provide additional advantages in formulating crystallizable drugs in a polymer matrix.

Examples of suitable dendritic polymers include poly (ether) based dendrons, dendrimers and hyperbranched polymers. poly(ester) based dendrons, dendrimers and hyperbranched polymers, poly(thioether) based dendrons, dendrimers and hyperbranched polymers, poly(amino acid) based dendrons dendrimers and hyperbranched polymers, poly(arylalkylene ether) based dendrons, dendrimers and hyperbranched polymers, poly(alkyleneimine) based dendrons, dendrimers and hyperbranched polymers, poly(amidoamine) based dendrons, dendrimers or hyperbranched polymers.

Other examples of hyperbranched polymers include poly (amines)s, polycarbonates, poly(ether ketone)s, polyurethanes, polycarbosilanes, polysiloxanes, poly(ester amine)s, poly(sulfone amine)s, poly(urea urethane)s and polyether polyols such as polyglycerols.

A film can be produced by a combination of at least one polymer and a solvent, optionally including other components. The solvent may be water, a polar organic solvent including, but not limited to, ethanol, isopropanol, acetone, or any combination thereof. In some embodiments, the solvent may be a non-polar organic solvent, such as methylene chloride. The film may be prepared by utilizing a selected casting or deposition method and a controlled drying process. For example, the film may be prepared through a controlled drying processes, which include application of heat and/or radiation energy to the wet film matrix to form a visco-elastic structure, thereby controlling the uniformity of content of the film. The controlled drying processes can include air alone, heat alone or heat and air together contacting the top of the film or bottom of the film or the substrate supporting the cast or deposited or extruded film or contacting more than one surface at the same time or at different times during the drying process.

Some of such processes are described in more detail in U.S. Pat. Nos. 8,765,167 and 8,652,378, which are incorporated by reference herein. Alternatively, the films may be extruded as described in U.S. Patent Publication No. 2005/0037055 A1, which is incorporated by reference herein.

A polymer included in the films may be water-soluble, water-swellable, water-insoluble, or a combination of one or more either water-soluble, water-swellable or water-insoluble polymers. The polymer may include cellulose, cellulose derivatives or gums. Specific examples of useful water-soluble polymers include, but are not limited to, polyethylene oxide, pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, xanthan gum, tragacanth gum, guar gum, acacia gum, arabic gum, polyacrylic acid, methylmethacrylate copolymer, carboxyvinyl copolymers, starch, gelatin, and combinations thereof. Specific examples of useful water-insoluble polymers include, but are not limited to, ethyl cellulose, hydroxypropyl ethyl cellulose, cellulose acetate phthalate, hydroxypropyl methyl cellulose phthalate and combinations thereof. For higher dosages, it may be desirable to incorporate a polymer that provides a high level of viscosity as compared to lower dosages.

As used herein the phrase "water-soluble polymer" and variants thereof refer to a polymer that is at least partially soluble in water, and desirably fully or predominantly soluble in water, or absorbs water. Polymers that absorb water are often referred to as being water-swellable polymers. The materials useful with the present invention may be water-soluble or water-swellable at room temperature and other temperatures, such as temperatures exceeding room temperature. Moreover, the materials may be water-soluble or water-swellable at pressures less than atmospheric pressure. In some embodiments, films formed from such water-soluble polymers may be sufficiently water-soluble to be dissolvable upon contact with bodily fluids.

Other polymers useful for incorporation into the films include biodegradable polymers, copolymers, block polymers or combinations thereof. It is understood that the term "biodegradable" is intended to include materials that chemically degrade, as opposed to materials that physically break apart (i.e., bioerodable materials). The polymers incorporated in the films can also include a combination of biodegradable or bioerodable materials. Among the known useful polymers or polymer classes which meet the above criteria are: poly(glycolic acid) (PGA), poly(lactic acid) (PLA), polydioxanes, polyoxalates, poly(alpha-esters), polyanhydrides, polyacetates, polycaprolactones, poly(orthoesters), polyamino acids, polyaminocarbonates, polyurethanes, polycarbonates, polyamides, poly(alkyl cyanoacrylates), and mixtures and copolymers thereof. Additional useful polymers include, stereopolymers of L- and D-lactic acid, copolymers of bis(p-carboxyphenoxy)propane acid and sebacic acid, sebacic acid copolymers, copolymers of caprolactone, poly(lactic acid)/poly(glycolic acid)/polyethyleneglycol copolymers, copolymers of polyurethane and (poly(lactic acid), copolymers of alpha-amino acids, copolymers of alpha-amino acids and caproic acid, copolymers of alpha-benzyl glutamate and polyethylene glycol, copolymers of succinate and poly(glycols), polyphosphazene, polyhydroxy-alkanoates or mixtures thereof. The polymer matrix can include one, two, three, four or more components.

Although a variety of different polymers may be used, it is desired to select polymers that provide mucoadhesive properties to the film, as well as a desired dissolution and/or disintegration rate. In particular, the time period for which it is desired to maintain the film in contact with the mucosal tissue depends on the type of pharmaceutically active component contained in the composition. Some pharmaceutically active components may only require a few minutes for delivery through the mucosal tissue, whereas other pharmaceutically active components may require up to several hours or even longer. Accordingly, in some embodiments, one or more water-soluble polymers, as described above, may be used to form the film. In other embodiments, however, it may be desirable to use combinations of water-soluble polymers and polymers that are water-swellable, water-insoluble and/or biodegradable, as provided above. The inclusion of one or more polymers that are water-swellable, water-insoluble and/or biodegradable may provide films with slower dissolution or disintegration rates than films formed from water-soluble polymers alone. As such, the film may adhere to the mucosal tissue for longer periods of time, such as up to several hours, which may be desirable for delivery of certain pharmaceutically active components.

Desirably, an individual film dosage of the pharmaceutical film can have a suitable thickness, and small size, which is between about 0.0625-3 inch by about 0.0625-3 inch. The film size can also be greater than 0.0625 inch, greater than 0.5 inch, greater than 1 inch, greater than 2 inches, about 3 inches, and greater than 3 inches, less than 3 inches, less than 2 inches, less than 1 inch, less than 0.5 inch, less than 0.0625 inch in at least one aspect, or greater than 0.0625 inch, greater than 0.5 inch, greater than 1 inch, greater than 2 inches, or greater than 3 inches, about 3 inches, less than 3 inches, less than 2 inches, less than 1 inch, less than 0.5 inch, less than 0.0625 inch in another aspect. The aspect ratio, including thickness, length, and width can be optimized by a person of ordinary skill in the art based on the chemical and physical properties of the polymeric matrix, the active pharmaceutical ingredient, dosage, enhancer, and other additives involved as well as the dimensions of the desired dispensing unit. The film dosage should have good adhesion when placed in the buccal cavity or in the sublingual region of the user. Further, the film dosage should disperse and dissolve at a moderate rate, most desirably dispersing within about 1 minute and dissolving within about 3 minutes. In some embodiments, the film dosage may be capable of dispersing and dissolving at a rate of between about 1 to about 30 minutes, for example, about 1 to about 20 minutes, or more than 1 minute, more than 5 minutes, more than 7 minutes, more than 10 minutes, more than 12 minutes, more than 15 minutes, more than 20 minutes, more than 30 minutes, about 30 minutes, or less than 30 minutes, less than 20 minutes, less than 15 minutes, less than 12 minutes, less than 10 minutes, less than 7 minutes, less than 5 minutes, or less than 1 minute. Sublingual dispersion rates may be shorter than buccal dispersion rates.

For instance, in some embodiments, the films may include polyethylene oxide alone or in combination with a second polymer component. The second polymer may be another water-soluble polymer, a water-swellable polymer, a water-insoluble polymer, a biodegradable polymer or any combination thereof. Suitable water-soluble polymers include, without limitation, any of those provided above. In some embodiments, the water-soluble polymer may include hydrophilic cellulosic polymers, such as hydroxypropyl cellulose and/or hydroxypropylmethyl cellulose. In some embodiments, one or more water-swellable, water-insoluble and/or biodegradable polymers also may be included in the polyethylene oxide-based film. Any of the water-swellable, water-insoluble or biodegradable polymers provided above may be employed. The second polymer component may be employed in amounts of about 0% to about 80% by weight in the polymer component, more specifically about 30% to about 70% by weight, and even more specifically about 40% to about 60% by weight, including greater than 5%, greater than 10%, greater than 15%, greater than 20%, greater than 30%, greater than 40%, greater than 50%, greater than 60%, and greater than 70%, about 70%, less than 70%, less than 60%, less than 50%, less than 40%, less than 30%, less than 20%, less than 10% or less than 5% by weight.

Additives may be included in the films. Examples of classes of additives include preservatives, antimicrobials, excipients, lubricants, buffering agents, stabilizers, blowing agents, pigments, coloring agents, fillers, bulking agents, sweetening agents, flavoring agents, fragrances, release modifiers, adjuvants, plasticizers, flow accelerators, mold release agents, polyols, granulating agents, diluents, binders, buffers, absorbents, glidants, adhesives, anti-adherents, acidulants, softeners, resins, demulcents, solvents, surfactants, emulsifiers, elastomers, anti-tacking agents, anti-static agents and mixtures thereof. These additives may be added with the pharmaceutically active component(s). As used herein, the term "stabilizer" means an excipient capable of preventing aggregation or other physical degradation, as well as chemical degradation, of the active pharmaceutical ingredient, another excipient, or the combination thereof.

Stabilizers may also be classified as antioxidants, sequestrants, pH modifiers, emulsifiers and/or surfactants, and UV stabilizers.

Antioxidants (i.e., pharmaceutically compatible compound(s) or composition(s) that decelerates, inhibits, interrupts and/or stops oxidation processes) include, in particular, the following substances: tocopherols and the esters thereof, sesamol of sesame oil, coniferyl benzoate of benzoin resin, nordihydroguairetic resin and nordihydroguaiaretic acid (NDGA), gallates (among others, methyl, ethyl, propyl, amyl, butyl, lauryl gallates), butylated hydroxyanisole (BHA/BHT, also butyl-p-cresol); ascorbic acid and salts and esters thereof (for example, acorbyl palmitate), erythorbinic acid (isoascorbinic acid) and salts and esters thereof, monothioglycerol, sodium formaldehyde sulfoxylate, sodium metabisulfite, sodium bisulfite, sodium sulfite, potassium metabisulfite, butylated hydroxyanisole, butylated hydroxytoluene (BHT), propionic acid. Typical antioxidants are tocopherol such as, for example, α-tocopherol and the esters thereof, butylated hydroxytoluene and butylated hydroxyanisole. The terms "tocopherol" also includes esters of tocopherol. A known tocopherol is α-tocopherol. The term "α-tocopherol" includes esters of α-tocopherol (for example, α-tocopherol acetate).

Sequestrants (i.e., any compounds which can engage in host-guest complex formation with another compound, such as the active ingredient or another excipient; also referred to as a sequestering agent) include calcium chloride, calcium disodium ethylene diamine tetra-acetate, glucono delta-lactone, sodium gluconate, potassium gluconate, sodium tripolyphosphate, sodium hexametaphosphate, and combinations thereof. Sequestrants also include cyclic oligosaccharides, such as cyclodextrins, cyclomannins (5 or more α-D-mannopyranose units linked at the 1,4 positions by a linkages), cyclogalactins (5 or more β-D-galactopyranose units linked at the 1,4 positions by 1 linkages), cycloaltrins (5 or more α-D-altropyranose units linked at the 1,4 positions by a linkages), and combinations thereof. pH modifiers include acids (e.g., tartaric acid, citric acid, lactic acid, fumaric acid, phosphoric acid, ascorbic acid, acetic acid, succinic acid, adipic acid and maleic acid), acidic amino acids (e.g., glutamic acid, aspartic acid, etc.), inorganic salts (alkali metal salt, alkaline earth metal salt, ammonium salt, etc.) of such acidic substances, a salt of such acidic substance with an organic base (e.g., basic amino acid such as lysine, arginine and the like, meglumine and the like), and a solvate (e.g., hydrate) thereof. Other examples of pH modifiers include silicified microcrystalline cellulose, magnesium aluminometasilicate, calcium salts of phosphoric acid (e.g., calcium hydrogen phosphate anhydrous or hydrate, calcium, sodium or potassium carbonate or hydrogencarbonate and calcium lactate or mixtures thereof), sodium and/or calcium salts of carboxymethyl cellulose, cross-linked carboxymethylcellulose (e.g., croscarmellose sodium and/or calcium), polacrilin potassium, sodium and or/calcium alginate, docusate sodium, magnesium calcium, aluminium or zinc stearate, magnesium palmitate and magnesium oleate, sodium stearyl fumarate, and combinations thereof.

Examples of emulsifiers and/or surfactants include poloxamers or pluronics, polyethylene glycols, polyethylene glycol monostearate, polysorbates, sodium lauryl sulfate, polyethoxylated and hydrogenated castor oil, alkyl polyoside, a grafted water soluble protein on a hydrophobic backbone, lecithin, glyceryl monostearate, glyceryl monostearate/polyoxyethylene stearate, ketostearyl alcohol/sodium lauryl sulfate, carbomer, phospholipids, $(C_{10}-C_{20})$-alkyl and alkylene carboxylates, alkyl ether carboxylates, fatty alcohol sulfates, fatty alcohol ether sulfates, alkylamide sulfates and sulfonates, fatty acid alkylamide polyglycol ether sulfates, alkanesulfonates and hydroxyalkanesulfonates, olefinsulfonates, acyl esters of isethionates, α-sulfo fatty acid esters, alkylbenzenesulfonates, alkylphenol glycol ether sulfonates, sulfosuccinates, sulfosuccinic monoesters and diesters, fatty alcohol ether phosphates, protein/fatty acid condensation products, alkyl monoglyceride sulfates and sulfonates, alkylglyceride ether sulfonates, fatty acid methyltaurides, fatty acid sarcosinates, sulforicinoleates, and acylglutamates, quaternary ammonium salts (e.g., di-$(C_{10}-C_{24})$-alkyl-dimethylammonium chloride or bromide), $(C_{10}-C_{24})$-alkyl-dimethylethylammonium chloride or bromide, $(C_{10}-C_{24})$-alkyl-trimethylammonium chloride or bromide (e.g., cetyltrimethylammonium chloride or bromide), $(C_{10}-C_{24})$-alkyl-dimethylbenzylammonium chloride or bromide (e.g., $(C_{12}-C_{18})$-alkyl-dimethylbenzylammonium chloride), N—$(C_{10}-C_{18})$-alkyl-pyridinium chloride or bromide (e.g., N—$(C_{12}-C_{16})$-alkyl-pyridinium chloride or bromide), N—$(C_{10}-C_{18})$-alkyl-isoquinolinium chloride, bromide or monoalkyl sulfate, N—$(C_{12}-C_{18})$-alkyl-polyoylaminoformylmethylpyridinium chloride, N—$(C_{12}-C_{18})$-alkyl-N-methylmorpholinium chloride, bromide or monoalkyl sulfate, N—$(C_{12}-C_{18})$-alkyl-N-ethylmorpholinium chloride, bromide or monoalkyl sulfate, $(C_{16}-C_{18})$-alkyl-pentaoxethylammonium chloride, diisobutylphenoxyethoxyethyldimethylbenzylammonium chloride, salts of N,N-diethylaminoethylstearylamide and -oleylamide with hydrochloric acid, acetic acid, lactic acid, citric acid, phosphoric acid, N-acylaminoethyl-N,N-diethyl-N-methylammonium chloride, bromide or monoalkyl sulfate, and N-acylaminoethyl-N,N-diethyl-N-benzylammonium chloride, bromide or monoalkyl sulfate (in the foregoing, "acyl" standing for, e.g., stearyl or oleyl), and combinations thereof.

Examples of UV stabilizers include UV absorbers (e.g., benzophenones), UV quenchers (i.e., any compound that dissipates UV energy as heat, rather than allowing the energy to have a degradation effect), scavengers (i.e., any compound that eliminates free radicals resulting from exposure to UV radiation), and combinations thereof.

In other embodiments, stabilizers include ascorbyl palmitate, ascorbic acid, alpha tocopherol, butylated hydroxytoluene, butylated hydroxyanisole, cysteine HCl, citric acid, ethylenediamine tetra acetic acid (EDTA), methionine, sodium citrate, sodium ascorbate, sodium thiosulfate, sodium metabi sulfite, sodium bisulfite, propyl gallate, glutathione, thioglycerol, singlet oxygen quenchers, hydroxyl radical scavengers, hydroperoxide removing agents, reducing agents, metal chelators, detergents, chaotropes, and combinations thereof. "Singlet oxygen quenchers" include, but are not limited to, alkyl imidazoles (e.g., histidine, L-camosine, histamine, imidazole 4-acetic acid), indoles (e.g., tryptophan and derivatives thereof, such as N-acetyl-5-methoxytryptamine, N-acetylserotonin, 6-methoxy-1,2,3,4-tetrahydro-beta-carboline), sulfur-containing amino acids (e.g., methionine, ethionine, djenkolic acid, lanthionine, N-formyl methionine, felinine, S-allyl cysteine, S-aminoethyl-L-cysteine), phenolic compounds (e.g., tyrosine and derivatives thereof), aromatic acids (e.g., ascorbate, salicylic acid, and derivatives thereof), azide (e.g., sodium azide), tocopherol and related vitamin E derivatives, and carotene and related vitamin A derivatives. "Hydroxyl radical scavengers" include, but are not limited to azide, dimethyl sulfoxide, histidine, mannitol, sucrose, glucose, salicylate, and L-cysteine. "Hydroperoxide removing agents" include, but are not limited to catalase, pyruvate, glutathione, and glutathione peroxidases. "Reducing agents" include, but are not limited to, cysteine and mercaptoethylene. "Metal chelators" include, but are not limited to, EDTA, EGTA, n-phenanthroline, and citrate. "Detergents" include, but are not limited to, SDS and sodium lauroyl sarcosyl. "Chaotropes" include, but are not limited to guandinium hydrochloride, isothiocyanate, urea, and formamide. As discussed herein, stabilizers can be present in 0.0001%-50% by weight, including greater than 0.0001%, greater than 0.001%, greater than 0.01%, greater than 0.1%, greater than 1%, greater than 5%, greater than 10%, greater than 20%, greater than 30%, greater than 40%, greater than 50%, less than 50%, less than 40%, less than 30%, less than 20%, less than 10%, less than 1%, less than 0.1%, less than 0.01%, less than 0.001%, or less than 0.0001% by weight.

Useful additives can include, for example, gelatin, vegetable proteins such as sunflower protein, soybean proteins, cotton seed proteins, peanut proteins, grape seed proteins, whey proteins, whey protein isolates, blood proteins, egg proteins, acrylated proteins, water-soluble polysaccharides such as alginates, carrageenans, guar gum, agar-agar, xanthan gum, gellan gum, gum arabic and related gums (gum ghatti, gum karaya, gum tragacanth), pectin, water-soluble derivatives of cellulose: alkylcelluloses hydroxyalkylcelluloses and hydroxyalkylalkylcelluloses, such as methylcellulose, hydroxymethylcellulose, hydroxyethylcellulose, hydroxypropylcellulose, hydroxyethylmethylcellulose, hydroxypropylmethylcellulose, hydroxybutylmethylcellulose, cellulose esters and hydroxyalkylcellulose esters such as cellulose acetate phthalate (CAP), hydroxypropylmethylcellulose (HPMC); carboxyalkylcelluloses, carboxyalkylalkylcelluloses, carboxyalkylcellulose esters such as carboxymethylcellulose and their alkali metal salts; water-soluble synthetic polymers such as polyacrylic acids and polyacrylic acid esters, polymethacrylic acids and polymethacrylic acid esters, polyvinylacetates, polyvinylalcohols, polyvinylacetatephthalates (PVAP), polyvinylpyrrolidone (PVP), PVA/vinyl acetate copolymer, and polycrotonic acids; also suitable are phthalated gelatin, gelatin succinate, crosslinked gelatin, shellac, water-soluble chemical derivatives of starch, cationically modified acrylates and methacrylates possessing, for example, a tertiary or quaternary amino group, such as the diethylaminoethyl group, which may be quaternized if desired; or other similar polymers.

The additional components can range up to about 80%, desirably about 0.005% to 50% and more desirably within the range of 1% to 20% based on the weight of all composition components, including greater than 1%, greater than 5%, greater than 10%, greater than 20%, greater than 30%, greater than 40%, greater than 50%, greater than 60%, greater than 70%, about 80%, greater than 80%, less than 80%, less than 70%, less than 60%, less than 50%, less than 40%, less than 30%, less than 20%, less than 10%, less than 5%, about 3%, or less than 1%. Other additives can include anti-tacking, flow agents and opacifiers, such as the oxides of magnesium aluminum, silicon, titanium, etc. desirably in a concentration range of about 0.005% to about 5% by weight and desirably about 0.02% to about 2% based on the weight of all film components, including greater than 0.02%, greater than 0.2%, greater than 0.5%, greater than 1%, greater than 1.5%, greater than 2%, greater than 4%, about 5%, greater than 5%, less than 4%, less than 2%, less than 1%, less than 0.5%, less than 0.2%, or less than 0.02%.

In certain embodiments, the composition can include plasticizers, which can include polyalkylene oxides, such as polyethylene glycols, polypropylene glycols, polyethylenepropylene glycols, organic plasticizers with low molecular weights, such as glycerol, glycerol monoacetate, diacetate or triacetate, triacetin, polysorbate, cetyl alcohol, propylene glycol, sugar alcohols sorbitol, sodium diethylsulfosuccinate, triethyl citrate, tributyl citrate, phytoextracts, fatty acid esters, fatty acids, oils and the like, added in concentrations ranging from about 0.1% to about 40%, and desirably ranging from about 0.5% to about 20% based on the weight of the composition including greater than 0.5%, greater than 1%, greater than 1.5%, greater than 2%, greater than 4%, greater than 5%, greater than 10%, greater than 15%, about 20%, greater than 20%, less than 20%, less than 15%, less than 10%, less than 5%, less than 4%, less than 2%, less than 1%, and less than 0.5%. There may further be added compounds to improve the texture properties of the film material such as animal or vegetable fats, desirably in their hydrogenated form. The composition can also include compounds to improve the textural properties of the product. Other ingredients can include binders which contribute to the ease of formation and general quality of the films. Non-limiting examples of binders include starches, natural gums, pregelatinized starches, gelatin, polyvinylpyrrolidone, methylcellulose, sodium carboxymethylcellulose, ethylcellulose, polyacrylamides, polyvinyloxoazolidone, or polyvinylalcohols.

Further potential additives include solubility enhancing agents, such as substances that form inclusion compounds with active components. Such agents may be useful in improving the properties of very insoluble and/or unstable actives. In general, these substances are doughnut-shaped molecules with hydrophobic internal cavities and hydrophilic exteriors. Insoluble and/or instable pharmaceutically active components may fit within the hydrophobic cavity, thereby producing an inclusion complex, which is soluble in water. Accordingly, the formation of the inclusion complex permits very insoluble and/or unstable pharmaceutically active components to be dissolved in water. A particularly desirable example of such agents are cyclodextrins, which are cyclic carbohydrates derived from starch. Other similar substances, however, are considered well within the scope of the present invention.

Suitable coloring agents include food, drug and cosmetic colors (FD&C), drug and cosmetic colors (D&C), or external drug and cosmetic colors (Ext. D&C). These colors are dyes, their corresponding lakes, and certain natural and derived colorants. Lakes are dyes absorbed on aluminum hydroxide. Other examples of coloring agents include known azo dyes, organic or inorganic pigments, or coloring agents of natural origin. Inorganic pigments are preferred, such as the oxides or iron or titanium, these oxides, being added in concentrations ranging from about 0.001 to about 10%, and preferably about 0.5 to about 3%, including greater than 0.001%, greater than 0.01%, greater than 0.1%, greater than 0.5%, greater than 1%, greater than 2%, greater than 5%, about 10%, greater than 10%, less than 10%, less than 5%, less than 2%, less than 1%, less than 0.5%, less than 0.1%, less than 0.01%, or less than 0.001%, based on the weight of all the components.

Flavors may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combinations thereof. A non-limiting representative list of examples includes mint oils, cocoa, and citrus oils such as lemon, orange, lime and grapefruit and fruit essences including apple, pear, peach, grape, strawberry, raspberry, cherry, plum, pineapple, apricot or other fruit flavors. Other useful flavorings include aldehydes and esters such as benzaldehyde (cherry, almond), citral i.e., alphacitral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanol (green fruit), and 2-dodecenal (citrus, mandarin), combinations thereof and the like.

The sweeteners may be chosen from the following non-limiting list: glucose (corn syrup), dextrose, invert sugar, fructose, and combinations thereof, saccharin and its various salts such as the sodium salt; dipeptide based sweeteners such as aspartame, neotame, advantame; dihydrochalcone compounds, glycyrrhizin; *Stevia Rebaudiana* (Stevioside); chloro derivatives of sucrose such as sucralose; sugar alcohols such as sorbitol, mannitol, xylitol, and the like. Also contemplated are hydrogenated starch hydrolysates and the synthetic sweetener 3,6-dihydro-6-methyl-1-1-1,2,3-oxathiazin-4-one-2,2-dioxide, particularly the potassium salt (acesulfame-K), and sodium and calcium salts thereof, and natural intensive sweeteners, such as Lo Han Kuo. Other sweeteners may also be used.

Anti-foaming and/or de-foaming components may also be used with the films. These components aid in the removal of air, such as entrapped air, from the film-forming compositions. Such entrapped air may lead to non-uniform films. Simethicone is one particularly useful anti-foaming and/or de-foaming agent. The present invention, however, is not so limited and other suitable anti-foam and/or de-foaming agents may be used. Simethicone and related agents may be employed for densification purposes. More specifically, such agents may facilitate the removal of voids, air, moisture, and similar undesired components, thereby providing denser and thus more uniform films. Agents or components which perform this function can be referred to as densification or densifying agents. As described above, entrapped air or undesired components may lead to non-uniform films.

Any other optional components described in commonly assigned U.S. Pat. Nos. 7,425,292 and 8,765,167, referred to above, also may be included in the films described herein.

The film compositions further desirably contains a buffer so as to control the pH of the film composition. Any desired level of buffer may be incorporated into the film composition so as to provide the desired pH level encountered as the pharmaceutically active component is released from the composition. The buffer is preferably provided in an amount sufficient to control the release from the film and/or the absorption into the body of the pharmaceutically active component. In some embodiments, the buffer may include sodium citrate, citric acid, bitartrate salt and combinations thereof.

The pharmaceutical films described herein may be formed via any desired process. Suitable processes are set forth in U.S. Pat. Nos. 8,652,378, 7,425,292 and 7,357,891, which are incorporated by reference herein. In one embodiment, the film dosage composition is formed by first preparing a wet composition, the wet composition including a polymeric carrier matrix and a therapeutically effective amount of a pharmaceutically active component. The wet composition is cast into a film and then sufficiently dried to form a self-supporting film composition. The wet composition may be cast into individual dosages, or it may be cast into a sheet, where the sheet is then cut into individual dosages.

The pharmaceutical composition can adhere to a mucosal surface. The present invention finds particular use in the localized treatment of body tissues, diseases, or wounds which may have moist surfaces and which are susceptible to bodily fluids, such as the mouth, the vagina, organs, or other types of mucosal surfaces. The composition carries a pharmaceutical, and upon application and adherence to the mucosal surface, offers a layer of protection and delivers the pharmaceutical to the treatment site, the surrounding tissues, and other bodily fluids. The composition provides an appropriate residence time for effective drug delivery at the treatment site, given the control of erosion in aqueous solution or bodily fluids such as saliva, and the slow, natural erosion of the film concomitant or subsequent to the delivery.

The residence time of the composition depends on the erosion rate of the water erodible polymers used in the formulation and their respective concentrations. The erosion rate may be adjusted, for example, by mixing together components with different solubility characteristics or chemically different polymers, such as hydroxyethyl cellulose and hydroxypropyl cellulose; by using different molecular weight grades of the same polymer, such as mixing low and medium molecular weight hydroxyethyl cellulose; by using excipients or plasticizers of various lipophilic values or water solubility characteristics (including essentially insoluble components); by using water soluble organic and inorganic salts; by using crosslinking agents such as glyoxal with polymers such as hydroxyethyl cellulose for partial crosslinking; or by post-treatment irradiation or curing, which may alter the physical state of the film, including its crystallinity or phase transition, once obtained. These strategies might be employed alone or in combination in order to modify the erosion kinetics of the film. Upon application, the pharmaceutical composition film adheres to the mucosal surface and is held in place. Water absorption softens the composition, thereby diminishing the foreign body sensation. As the composition rests on the mucosal surface, delivery of the drug occurs. Residence times may be adjusted over a wide range depending upon the desired timing of the delivery of the chosen pharmaceutical and the desired lifespan of the carrier. Generally, however, the residence time is modulated between about a few seconds to about a few days. Preferably, the residence time for most pharmaceuticals is adjusted from about 5 seconds to about 24 hours. More preferably, the residence time is adjusted from about 5 seconds to about 30 minutes. In addition to providing drug delivery, once the composition adheres to the mucosal surface, it also provides protection to the treatment site, acting as an erodible bandage. Lipophilic agents can be designed to slow down erodability to decrease disintegration and dissolution.

It is also possible to adjust the kinetics of erodability of the composition by adding excipients which are sensitive to enzymes such as amylase, very soluble in water such as water soluble organic and inorganic salts. Suitable excipients may include the sodium and potassium salts of chloride, carbonate, bicarbonate, citrate, trifluoroacetate, benzoate, phosphate, fluoride, sulfate, or tartrate. The amount added can vary depending upon how much the erosion kinetics is to be altered as well as the amount and nature of the other components in the composition.

Emulsifiers typically used in the water-based emulsions described above are, preferably, either obtained in situ if selected from the linoleic, palmitic, myristoleic, lauric, stearic, cetoleic or oleic acids and sodium or potassium hydroxide, or selected from the laurate, palmitate, stearate, or oleate esters of sorbitol and sorbitol anhydrides, polyoxyethylene derivatives including monooleate, monostearate, monopalmitate, monolaurate, fatty alcohols, alkyl phenols, allyl ethers, alkyl aryl ethers, sorbitan monostearate, sorbitan monooleate and/or sorbitan monopalmitate.

The amount of pharmaceutically active component to be used depends on the desired treatment strength and the composition of the layers, although preferably, the pharmaceutical component comprises from about 0.001% to about 99%, more preferably from about 0.003 to about 75%, and most preferably from about 0.005% to about 50% by weight of the composition, including, more than 0.005%, more than 0.05%. more than 0.5%, more than 1%, more than 5%, more than 10%, more than 15%, more than 20%, more than 30%, about 50%, more than 50%, less than 50%, less than 30%, less than 20%, less than 15%, less than 10%, less than 5%, less than 1%, less than 0.5%, less than 0.05%, or less than 0.005%. The amounts of other components may vary depending on the drug or other components but typically these components comprise no more than 50%, preferably no more than 30%, and most preferably no more than 15% by total weight of the composition.

The thickness of the film may vary, depending on the thickness of each of the layers and the number of layers. As stated above, both the thickness and amount of layers may be adjusted in order to vary the erosion kinetics. Preferably, if the composition has only two layers, the thickness ranges from 0.005 mm to 2 mm, preferably from 0.01 to 1 mm, and more preferably from 0.1 to 0.5 mm, including greater than 0.1 mm, greater than 0.2 mm, about 0.5 mm, greater than 0.5 mm, less than 0.5 mm, less than 0.2 mm, or less than 0.1 mm. The thickness of each layer may vary from 10 to 90% of the overall thickness of the layered composition, and preferably varies from 30 to 60%, including greater than 10%, greater than 20%, greater than 30%, greater than 40%, greater than 50%, greater than 70%, greater than 90%, about 90%, less than 90%, less than 70%, less than 50%, less than 40%, less than 30%, less than 20%, or less than 10%. Thus, the preferred thickness of each layer may vary from 0.01 mm to 0.9 mm, or from 0.03 to 0.5 mm.

As one skilled in the art will appreciate, when systemic delivery, e.g., transmucosal or transdermal delivery is desired, the treatment site may include any area in which the film is capable of delivery and/or maintaining a desired level of pharmaceutical in the blood, lymph, or other bodily fluid. Typically, such treatment sites include the oral, aural, ocular, anal, nasal, and vaginal mucosal tissue, as well as, the skin. If the skin is to be employed as the treatment site, then usually larger areas of the skin wherein movement will not disrupt the adhesion of the film, such as the upper arm or thigh, are preferred.

The pharmaceutical composition can also be used as a wound dressing. By offering a physical, compatible, oxygen and moisture permeable, flexible barrier which can be washed away, the film can not only protect a wound but also deliver a pharmaceutical in order to promote healing, aseptic, scarification, to ease the pain or to improve globally the condition of the sufferer. Some of the: examples given below are well suited for an application to the skin or a wound. As one skilled in the art will appreciate, the formulation might require incorporating a specific hydrophilic/hygroscopic excipient which would help in maintaining good adhesion on dry skin over an extended period of time. Another advantage of the present invention when utilized in this manner is that if one does not wish that the film be noticeable on the skin, then no dyes or colored substances need be used. If, on the other hand, one desires that the film be noticeable, a dye or colored substance may be employed.

While the pharmaceutical composition can adhere to mucosal tissues, which are wet tissues by nature, it can also be used on other surfaces such as skin or wounds. The pharmaceutical film can adhere to the skin if prior to application the skin is wet with an aqueous-based fluid such as water, saliva, wound drainage or perspiration. The film can adhere to the skin until it erodes due to contact with water by, for example, rinsing, showering, bathing or washing. The film may also be readily removed by peeling without significant damage to tissue.

A Franz diffusion cell is an in vitro skin permeation assay used in formulation development. The Franz diffusion cell apparatus (FIG. 1A) consists of two chambers separated by a membrane of, for example, animal or human tissue. The test product is applied to the membrane via the top chamber. The bottom chamber contains fluid from which samples are taken at regular intervals for analysis to determine the amount of active that has permeated the membrane. Referring to FIG. 1A, a Franz diffusion cell 100 includes a donor compound 101, a donor chamber 102, a membrane 103, sampling port 104, receptor chamber 105, stir bar 106, and a heater/circulator 107.

Figure 1B:
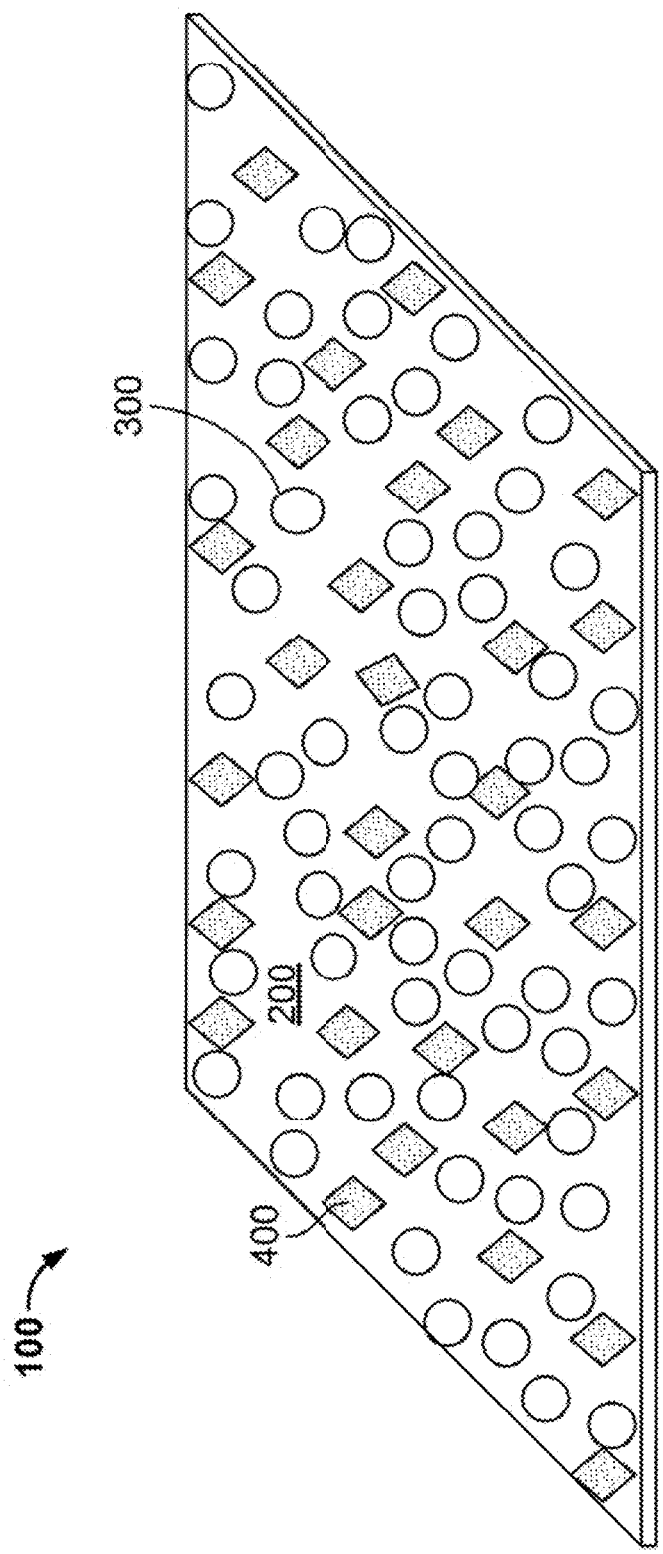
Referring to FIG. 1B, a pharmaceutical composition is a film 100 comprising a polymeric matrix 200, the pharmaceutically active component 300 being contained in the polymeric matrix. The film can include a permeation enhancer 400.

Referring to FIG. 1B, a pharmaceutical composition is a film 100 comprising a polymeric matrix 200, the pharmaceutically active component 300 being contained in the polymeric matrix. The film can include a permeation enhancer 400.

Figure 2A:
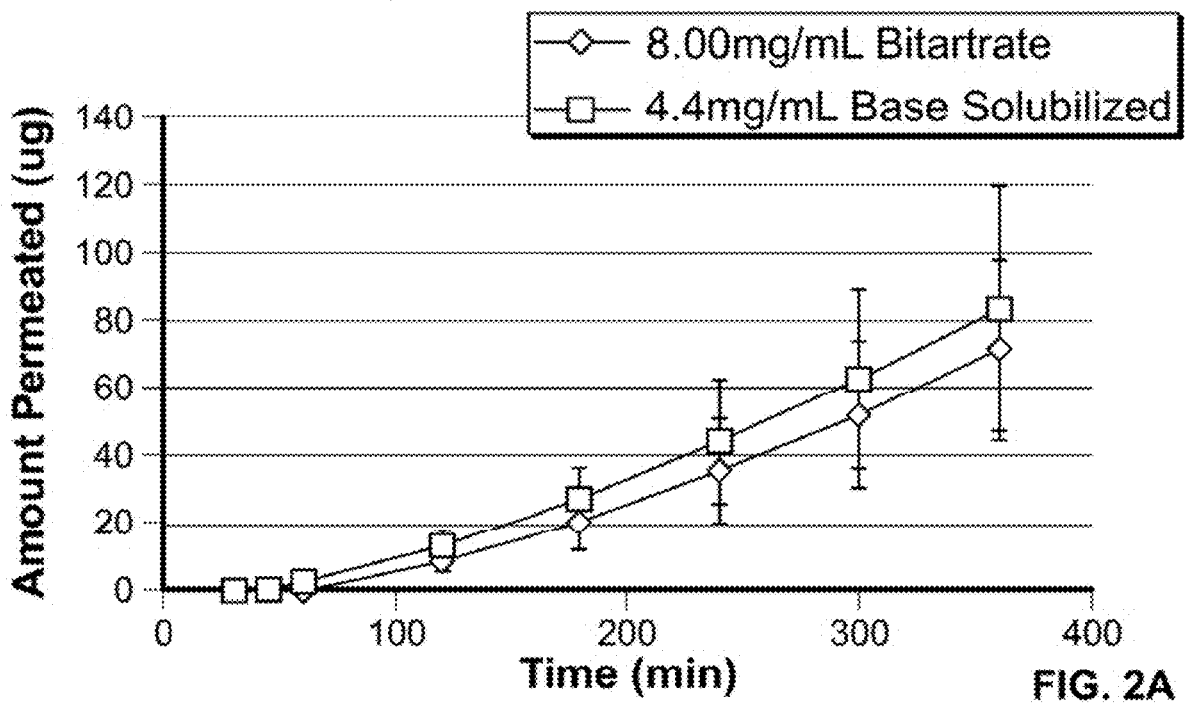
Referring to FIGS. 2A and 2B, the graphs show the permeation of an active material from a composition.
Figure 2B:
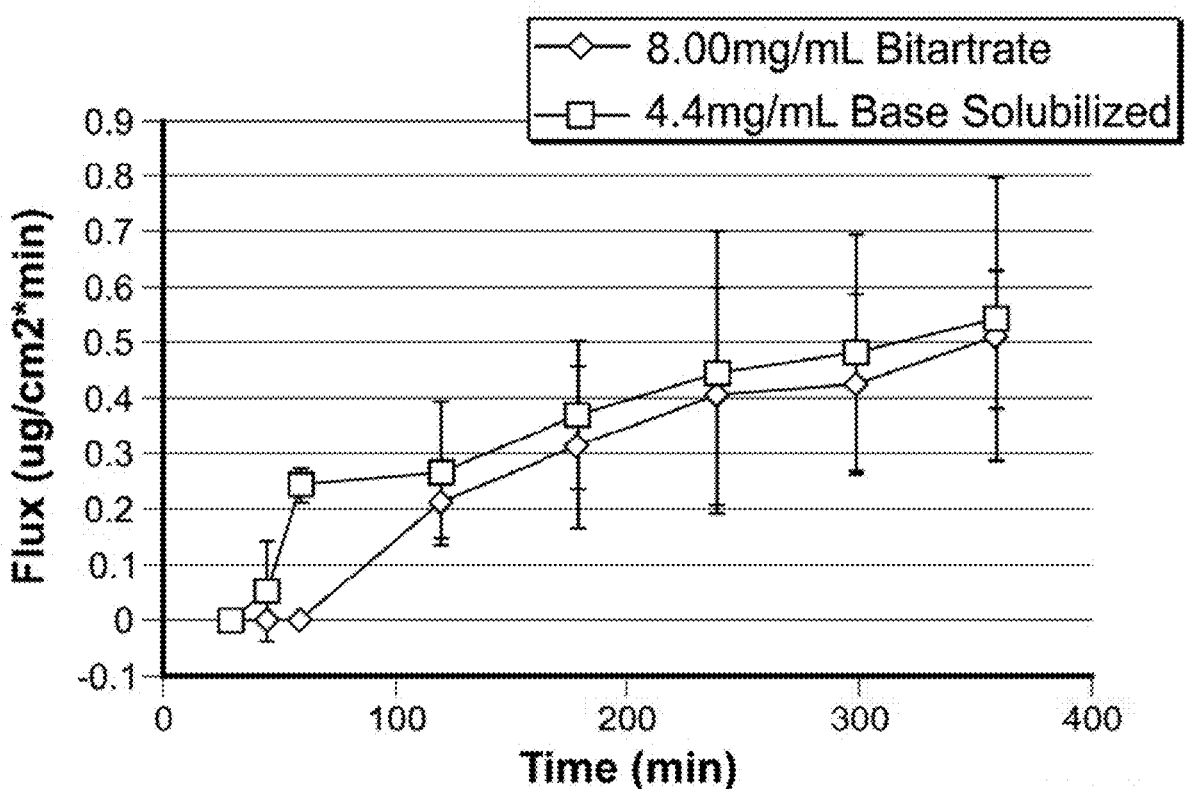

Referring to FIGS. 2A and 2B, the graphs show the permeation of an active material from a composition. The graph shows that for the epinephrine base—solubilized in-situ vs. the inherently soluble epinephrine bitartrate, no meaningful differences were observed. Epinephrine bitartrate was selected for further development based on ease of processing. Flux is derived as slope of the amount permeated as a function of time. Steady state flux is taken from the plateau of flux vs time curve multiplied by the volume of receiver media and normalized for permeation area.

Referring to FIG. 2A, this graph shows average amount of active material permeated vs. time, with 8.00 mg/mL epinephrine bitartrate and 4.4 mg/mL epinephrine base solubilized.

Referring to FIG. 2B, this graph shows average flux vs. time, with 8.00 mg/mL epinephrine bitartrate and 4.4 mg/mL epinephrine base solubilized.

Figure 3:
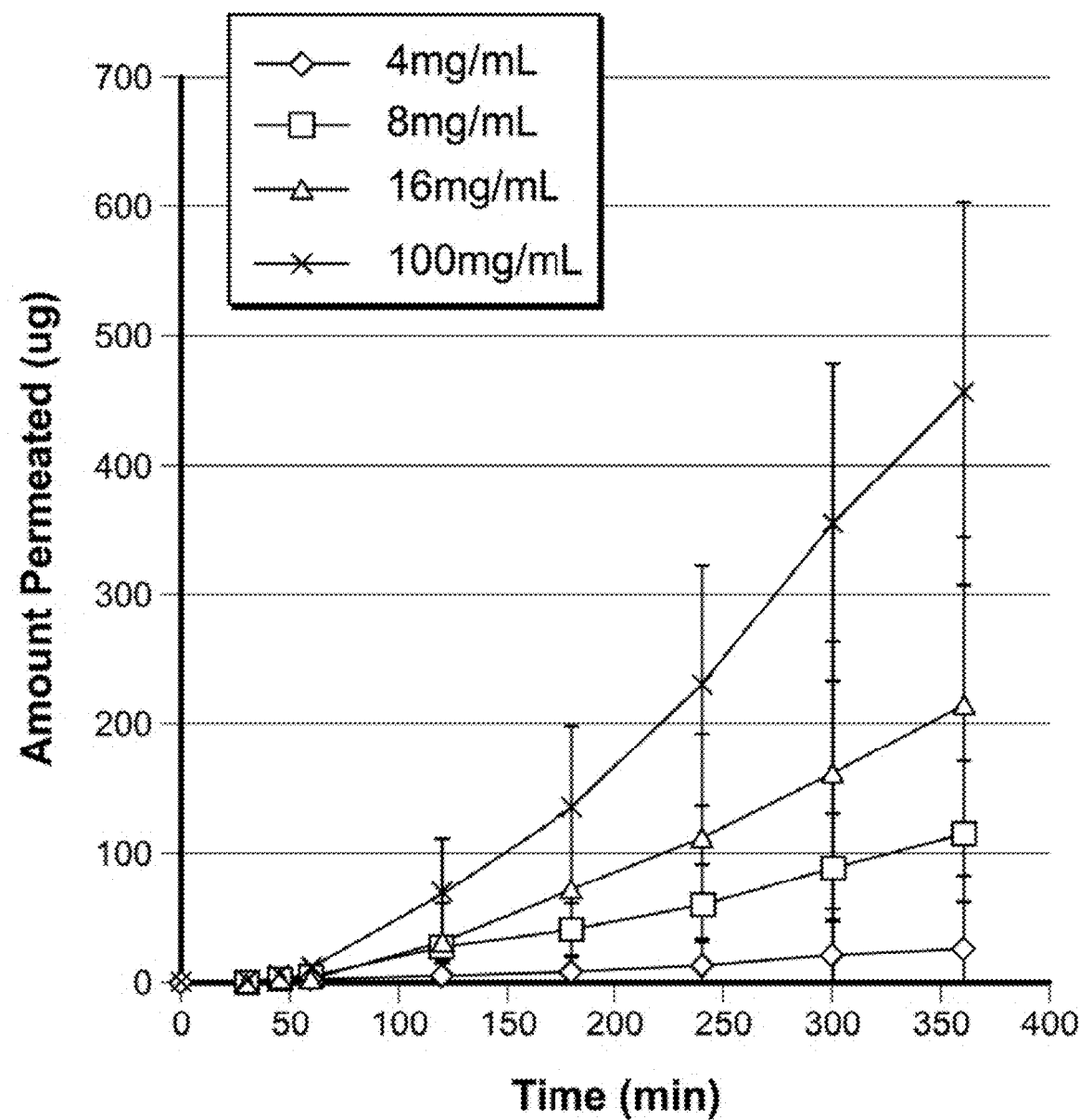
Referring to FIG. 3, this graph shows ex-vivo permeation of epinephrine bitartrate as a function of concentration.

Referring to FIG. 3, this graph shows ex-vivo permeation of epinephrine bitartrate as a function of concentration. The study compared concentrations of 4 mg/mL, 8 mg/mL, 16 mg/mL and 100 mg/mL. Results showed that increasing concentration resulted in increased permeation, and level of enhancement diminishes at higher loading.

Figure 4:
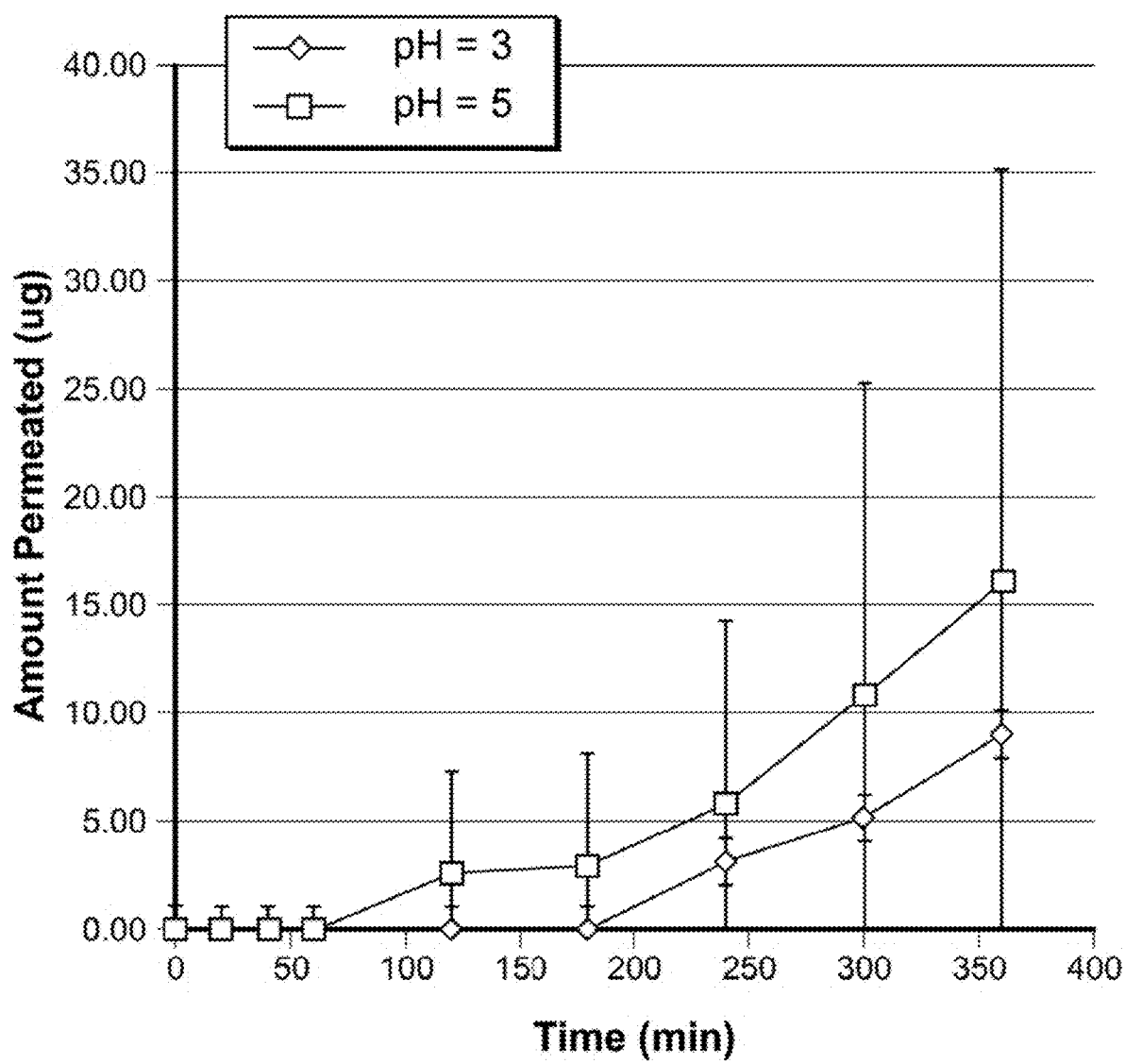
Referring to FIG. 4, this graph shows permeation of epinephrine bitartrate as a function of solution pH.

Referring to FIG. 4, this graph shows permeation of epinephrine bitartrate as a function of solution pH. Acidic conditions explored to promote stability. The results compared epinephrine bitartrate pH 3 buffer and epinephrine bitartrate pH 5 buffer, and found that the epinephrine bitartrate pH 5 buffer was slightly favorable.

Figure 5:
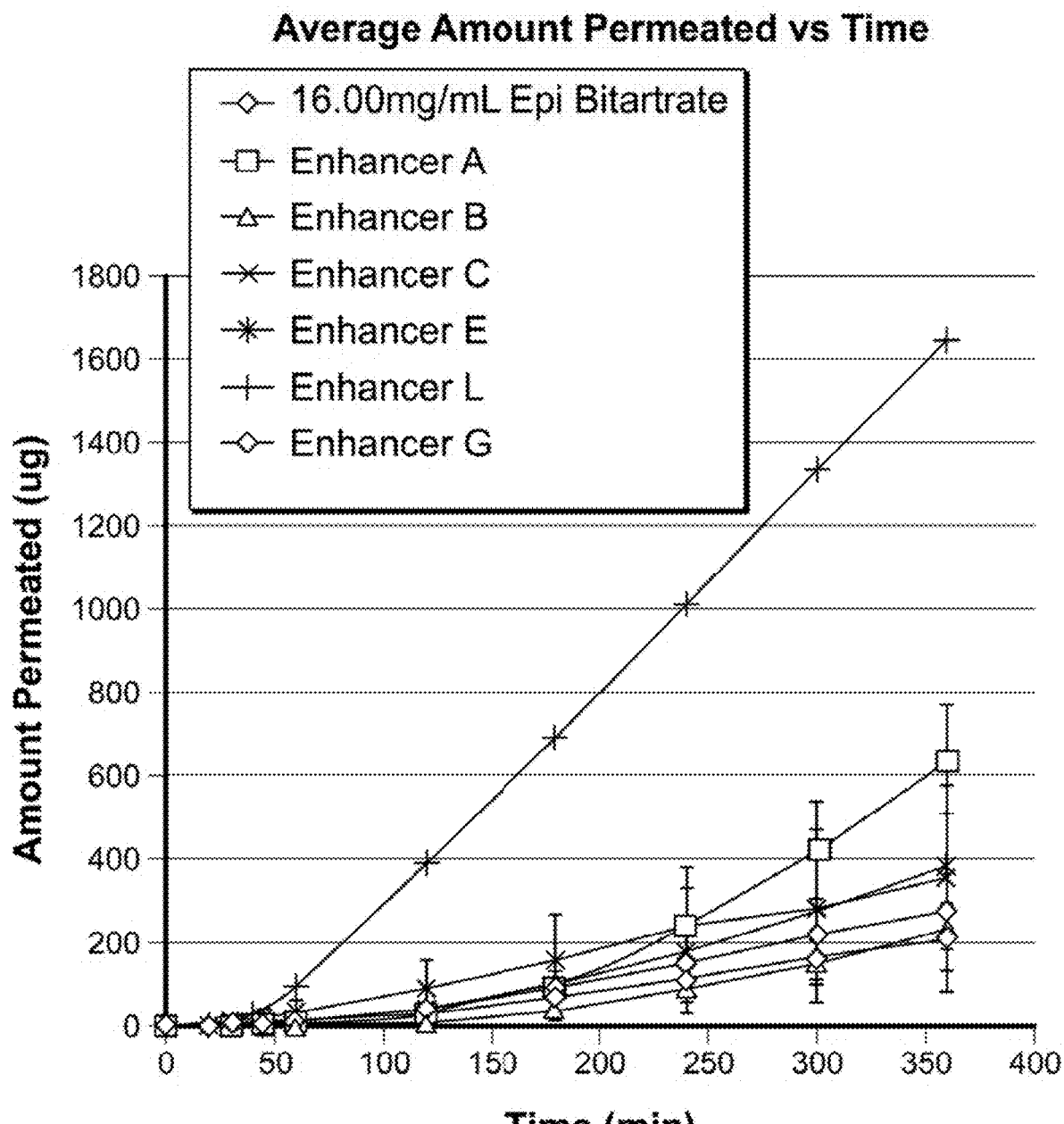
Referring to FIG. 5, this graph shows the influence of enhancers on permeation of epinephrine, indicated as amount permeated as a function of time.

Referring to FIG. 5, this graph shows the influence of enhancers on permeation of epinephrine, indicated as amount permeated as a function of time. Multiple enhancers were screened, including Labrasol, caproyl 90, Plurol Oleique, Labrafil, TDM, SGDC, Gelucire 44/14 and clove oil. Significant impact on time to onset and steady state flux was achieved, and surprisingly enhanced permeation was achieved for clove oil and Labrasol.

Figure 6A:
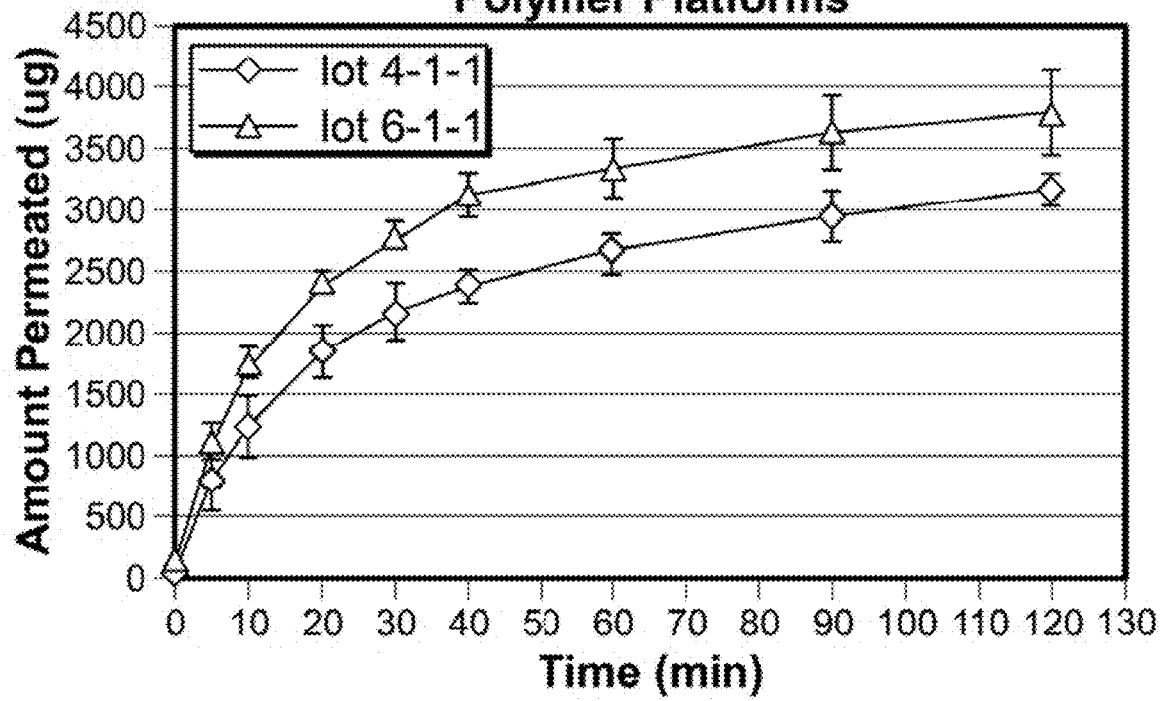
Referring to FIGS. 6A and 6B, these graphs show the release of epinephrine on polymer platforms (6A) and the effect of enhancers on its release (6B), indicated as amount permeated (in μg) vs. time.
Figure 6B:
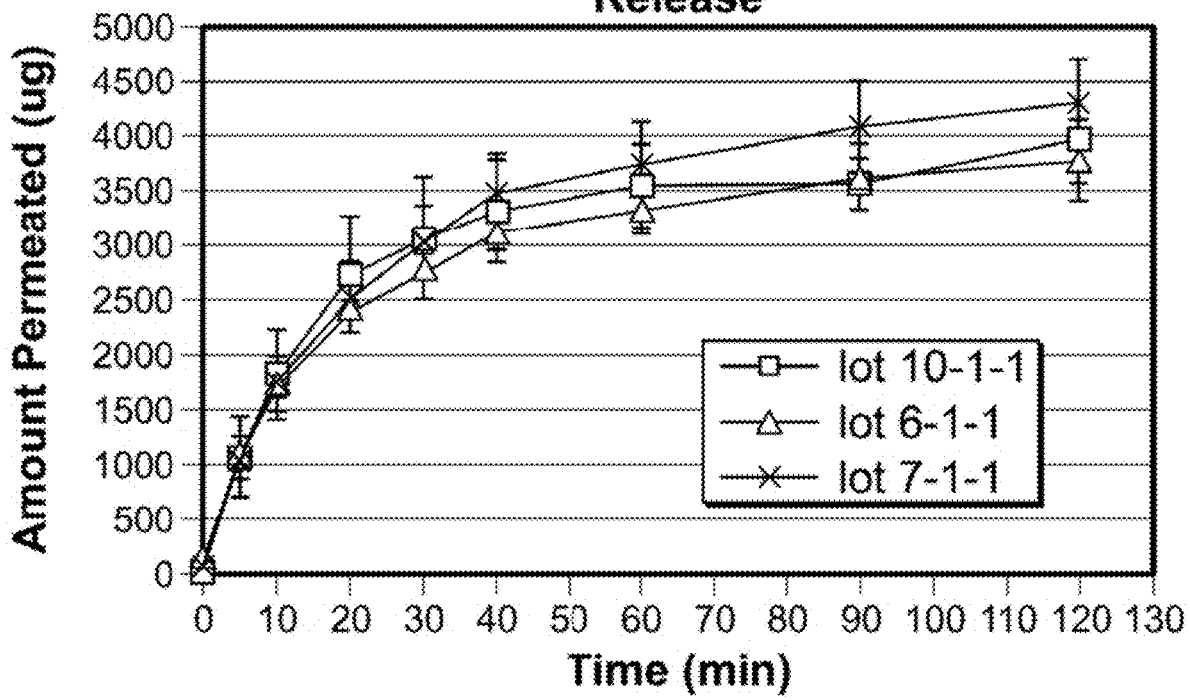

Referring to FIGS. 6A and 6B, these graphs show the release of epinephrine on polymer platforms and the effect of enhancers on its release, indicated as amount permeated (in μg) vs. time. FIG. 6A shows the epinephrine release from different polymer platforms. FIG. 6B shows the impact of enhancers on epinephrine release.

Figure 7:
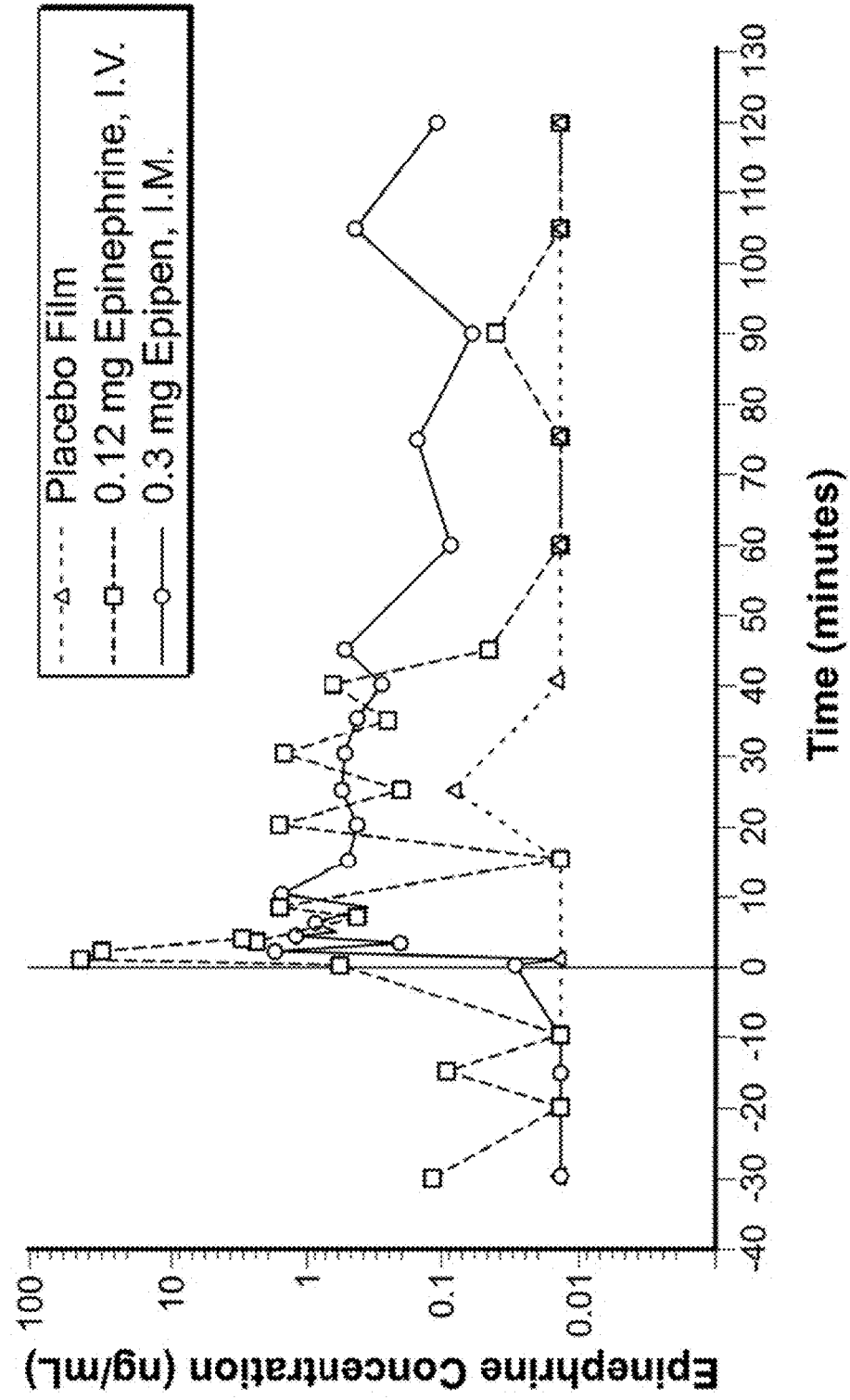
Referring to FIG. 7, this graph shows a pharmacokinetic model in the male Yucatan, miniature swine. The study compares a 0.3 mg Epipen, a 0.12 mg Epinephrine IV and a placebo film.

Referring to FIG. 7, this graph shows a pharmacokinetic model in the male Yucatan, miniature swine. The study compares a 0.3 mg Epipen, a 0.12 mg Epinephrine IV and a placebo film.

Figure 8:
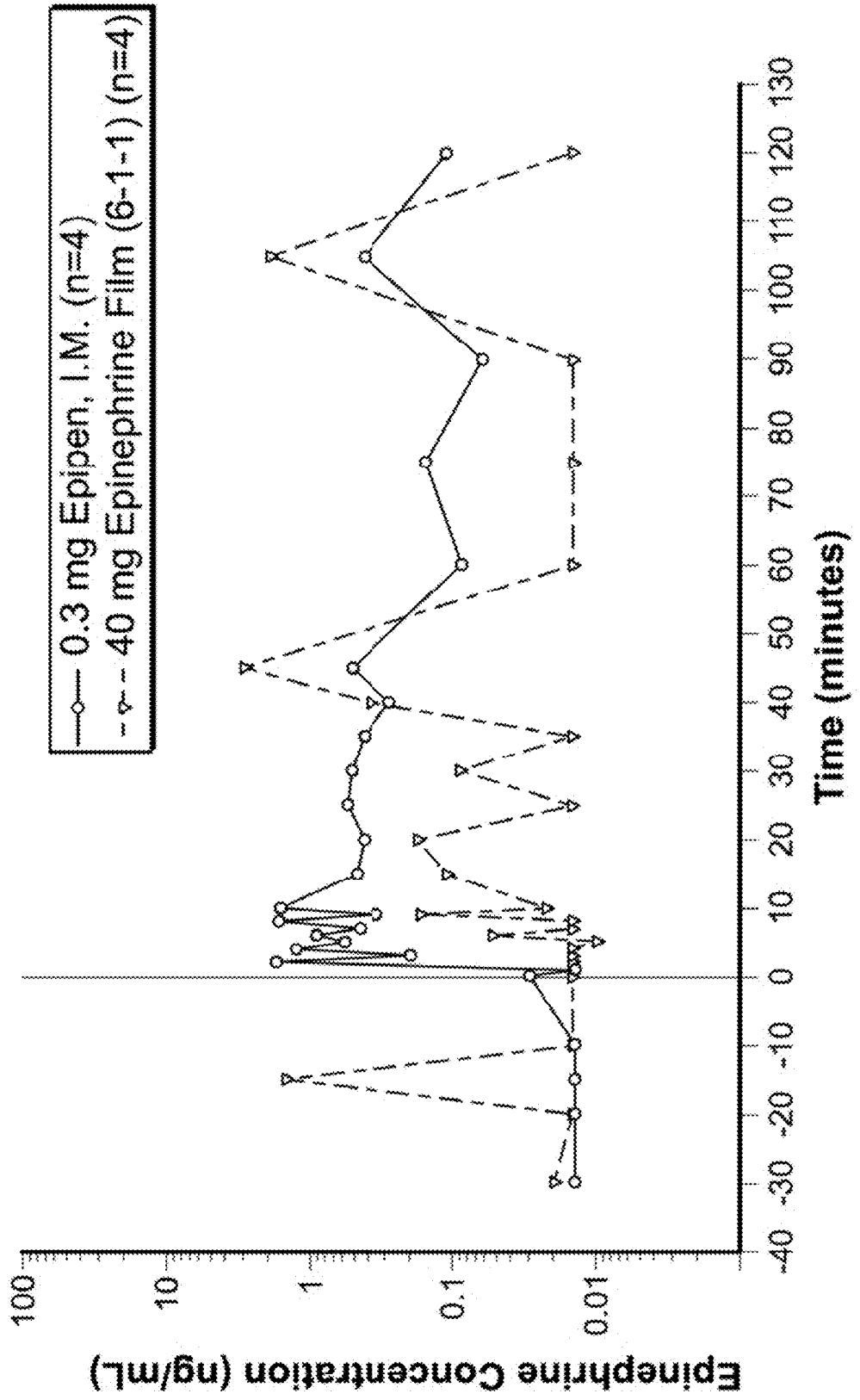
Referring to FIG. 8, this graph shows the impact of no enhancer on the concentration profiles of a 40 mg epinephrine film vs 0.3 mg Epipen.

Referring to FIG. 8, this graphs shows the impact of no enhancer on the concentration profiles of a 40 mg epinephrine film vs, a 0.3 mg Epipen.

Figure 9:
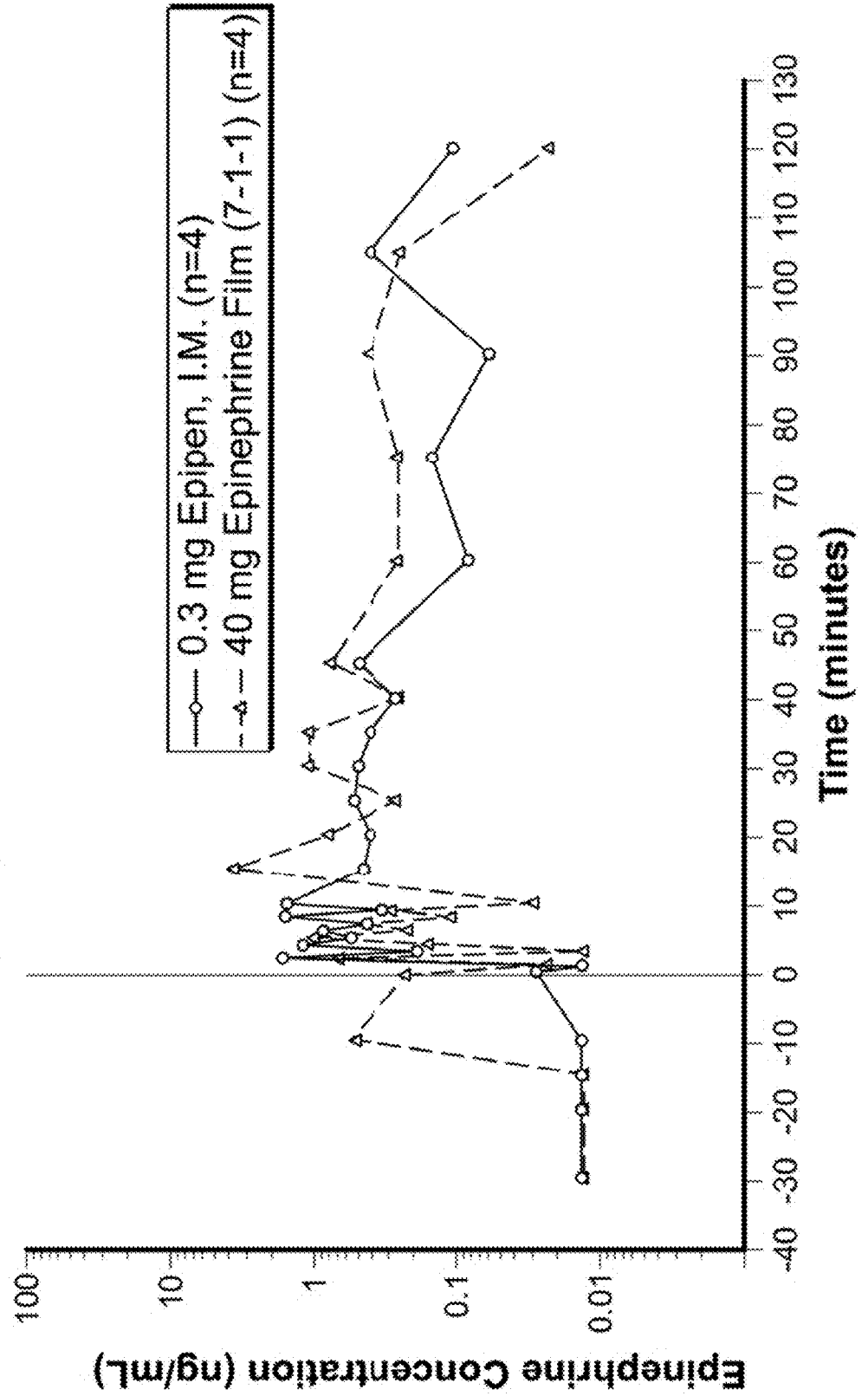
Referring to FIG. 9, this graph shows the impact of Enhancer A (Labrasol) on the concentration profiles of a 40 mg epinephrine film vs 0.3 mg Epipen.
Figure 10:
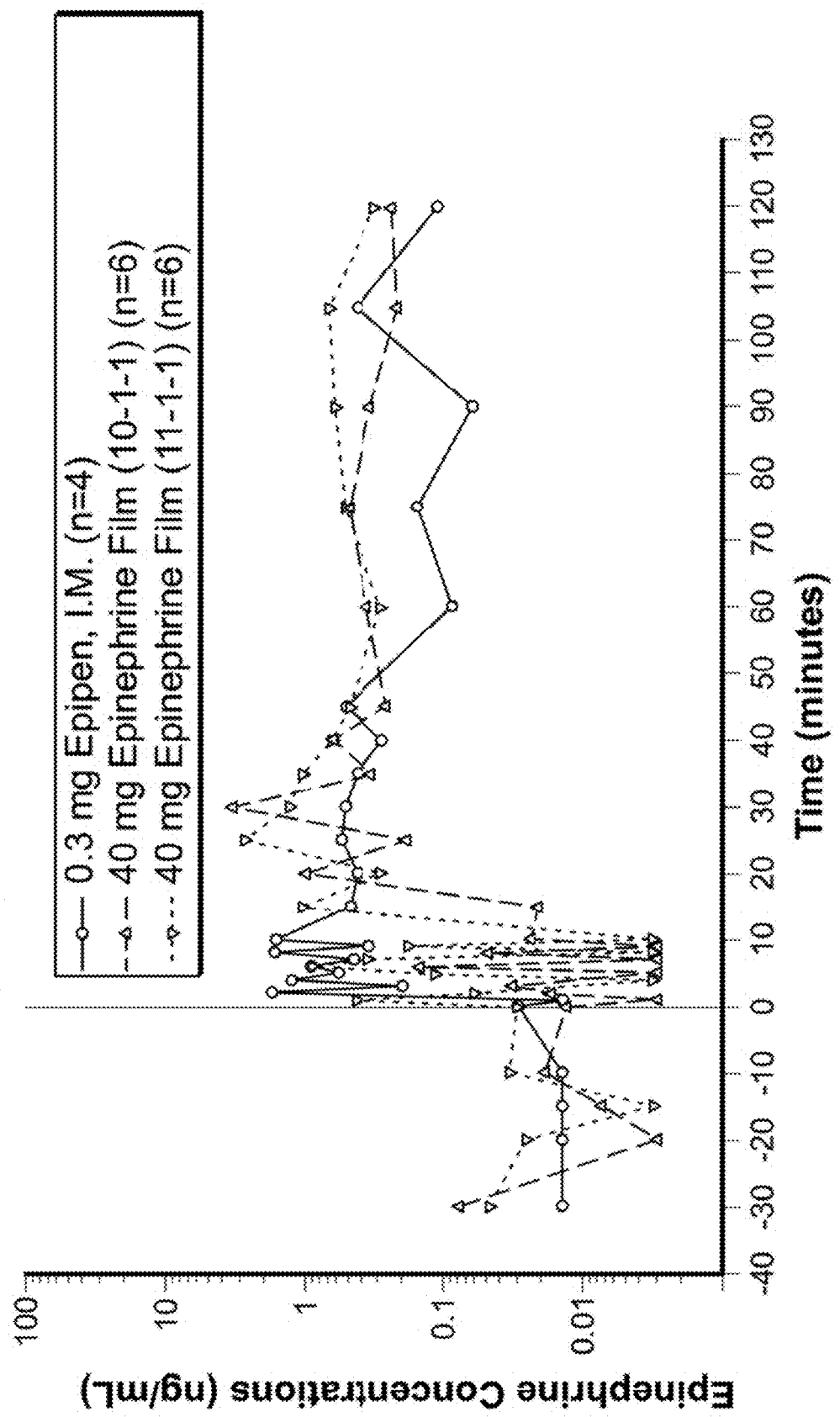
Referring to FIG. 10, this graph shows the impact of Enhancer L (clove oil) on the concentration profiles of two 40 mg Epinephrine films (10-1-1) and (11-1-1) vs. a 0.3 mg Epipen.

Referring to FIG. 9, this graph shows the impact of Enhancer A (Labrasol) on the concentration profiles of a 40 mg epinephrine film vs, a 0.3 mg Epipen. Referring to FIG. 10, this graph shows the impact of Enhancer L (clove oil) on the concentration profiles of two 40 mg Epinephrine films (10-1-1) and (11-1-1) vs. a 0.3 mg Epipen.

Figure 11:
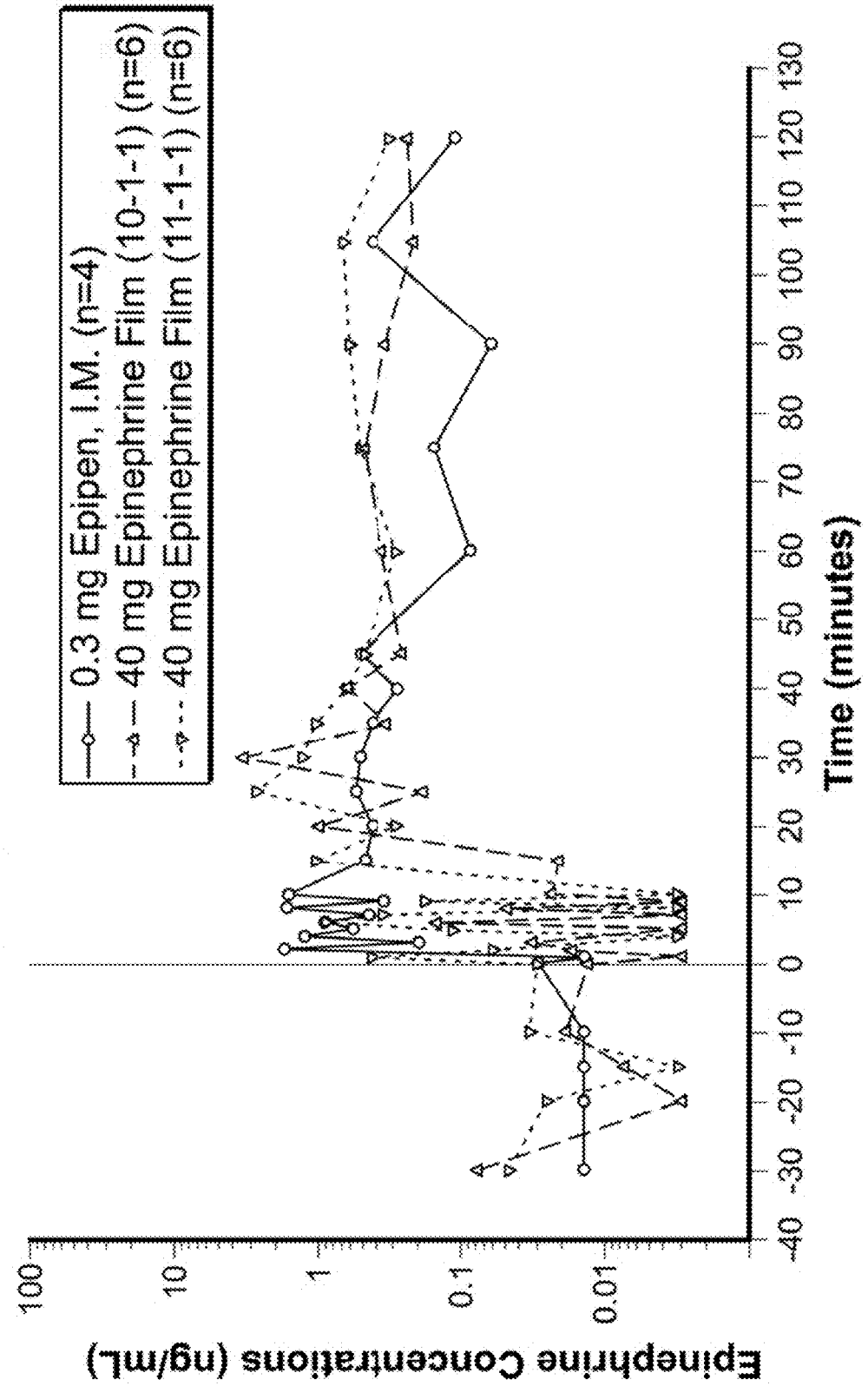
Referring to FIG. 11, this graph shows the impact of Enhancer L (clove oil) and film dimension (10-1-1 thinner, bigger film and 11-1-1 thicker, smaller film) on the concentration profiles of 40 mg Epinephrine films vs. a 0.3 mg Epipen.

Referring to FIG. 11, This graph shows the impact of Enhancer L (clove oil) and film dimension (10-1-1 thinner bigger film and 11-1-1 thicker smaller film) on the concentration profiles of 40 mg Epinephrine films vs. a 0.3 mg Epipen.

Figure 12:
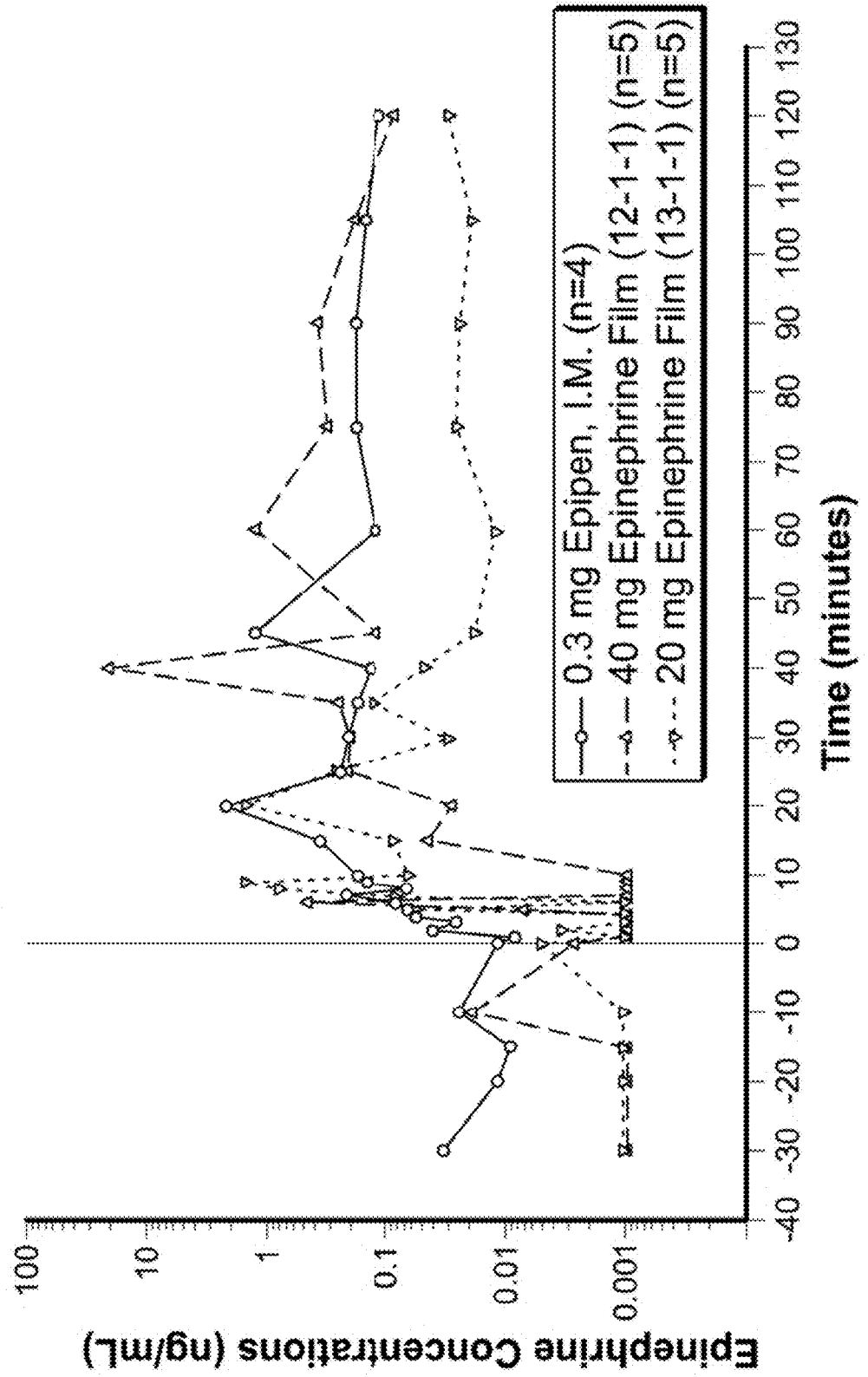
Referring to FIG. 12, this graph shows the concentration profiles for varying doses of Epinephrine films in a constant matrix for Enhancer L (clove oil) vs. a 0.3 mg Epipen.

Referring to FIG. 12, this graph shows the concentration profiles for varying doses of Epinephrine films in a constant matrix for Enhancer L (clove oil) vs. a 0.3 mg Epipen.

Figure 13:
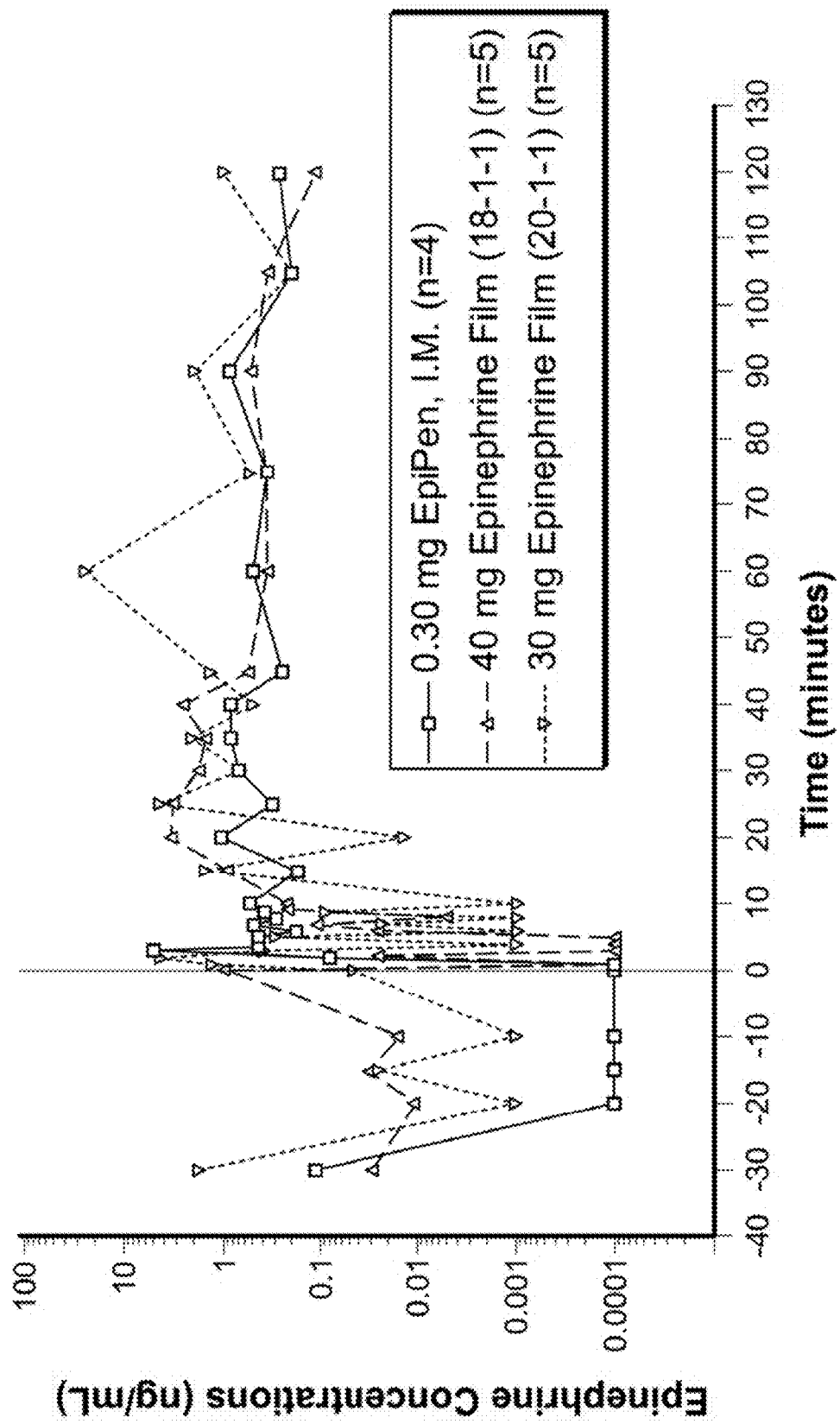
Referring to FIG. 13, this graph shows the concentration profiles for varying doses of epinephrine films in a constant matrix for Enhancer L (clove oil) vs. a 0.3 mg Epipen.

Referring to FIG. 13, the graph shows the concentration profiles for varying doses of Epinephrine films in a constant matrix for Enhancer L (clove oil) vs. a 0.3 mg Epipen.

Figure 14:
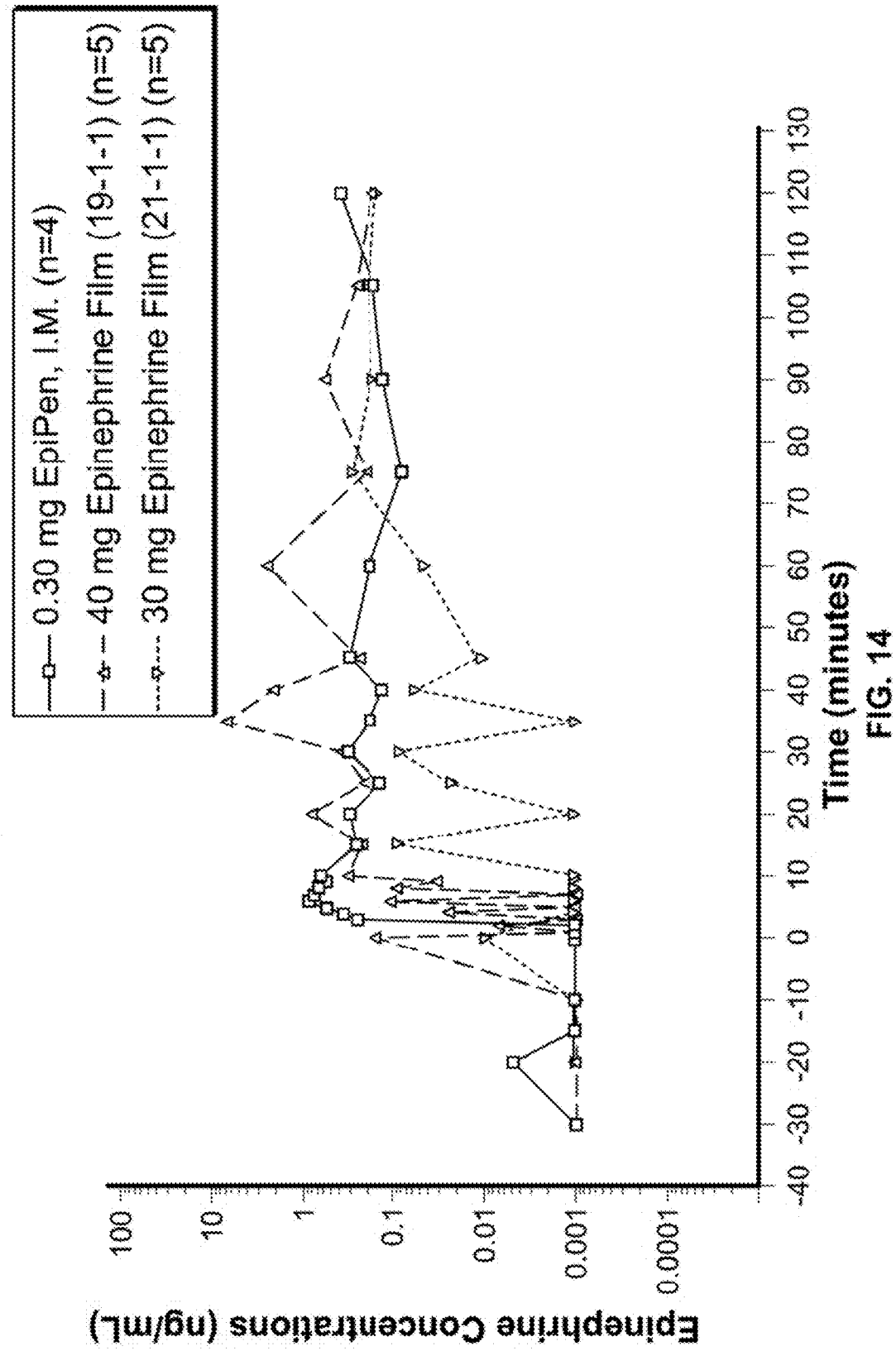
Referring to FIG. 14, this graph shows the concentration profiles for varying doses of epinephrine films in a constant matrix for Enhancer A (Labrasol) vs. a 0.3 mg Epipen.

Referring to FIG. 14, the graph shows the concentration profiles for varying doses of Epinephrine films in a constant matrix for Enhancer A (Labrasol) vs. a 0.3 mg Epipen.

Figure 15:
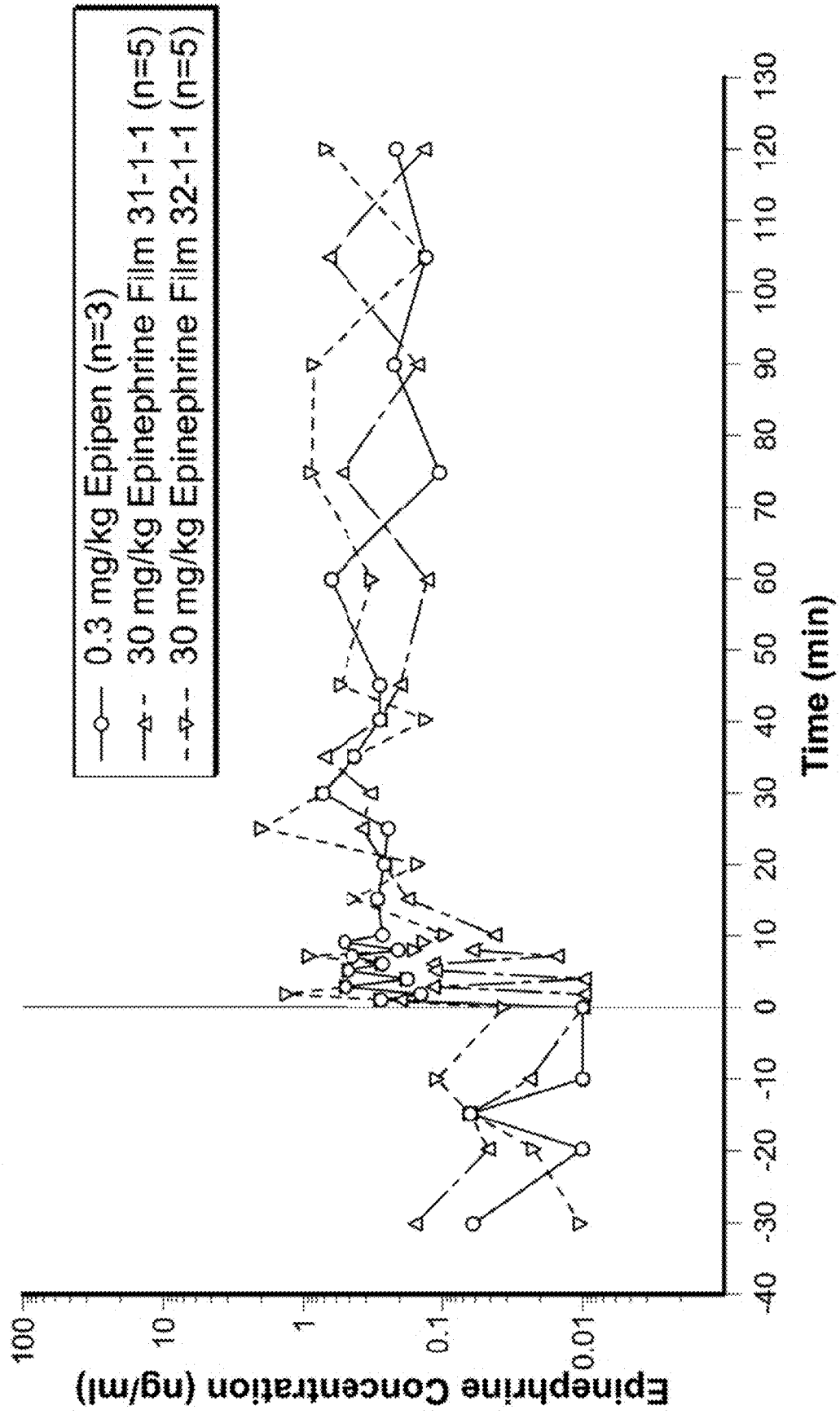
Referring to FIG. 15, this graph shows the impact of Farnesol and Farnesol in combination with Linoleic Acid on plasma concentration profiles of 40 mg Epinephrine Films vs. a 0.3 mg Epipen.

Referring to FIG. 15, this graph shows the impact of Farnesol and Farnesol in combination with Linoleic Acid on plasma concentration profiles of 40 mg Epinephrine Films vs. a 0.3 mg Epipen.

Figure 16:
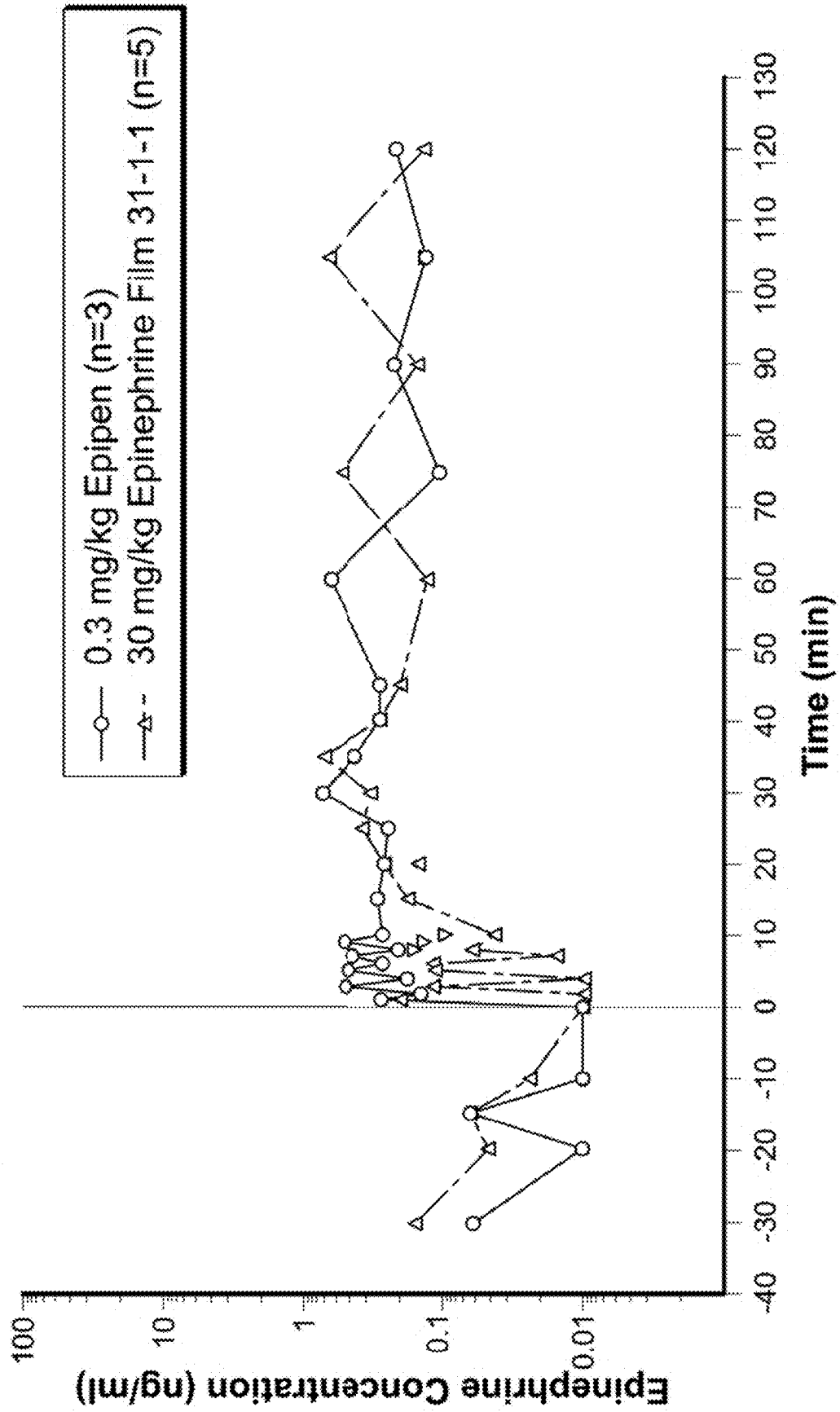
Referring to FIG. 16, this graph shows the impact of Farnesol on plasma concentration profiles of 40 mg epinephrine films vs a 0.3 mg Epipen.

Referring to FIG. 16, this graph shows the impact of Farnesol and Farnesol in combination with Linoleic Acid on plasma concentration profiles of 40 mg Epinephrine Films vs. a 0.3 mg Epipen.

Figure 17:
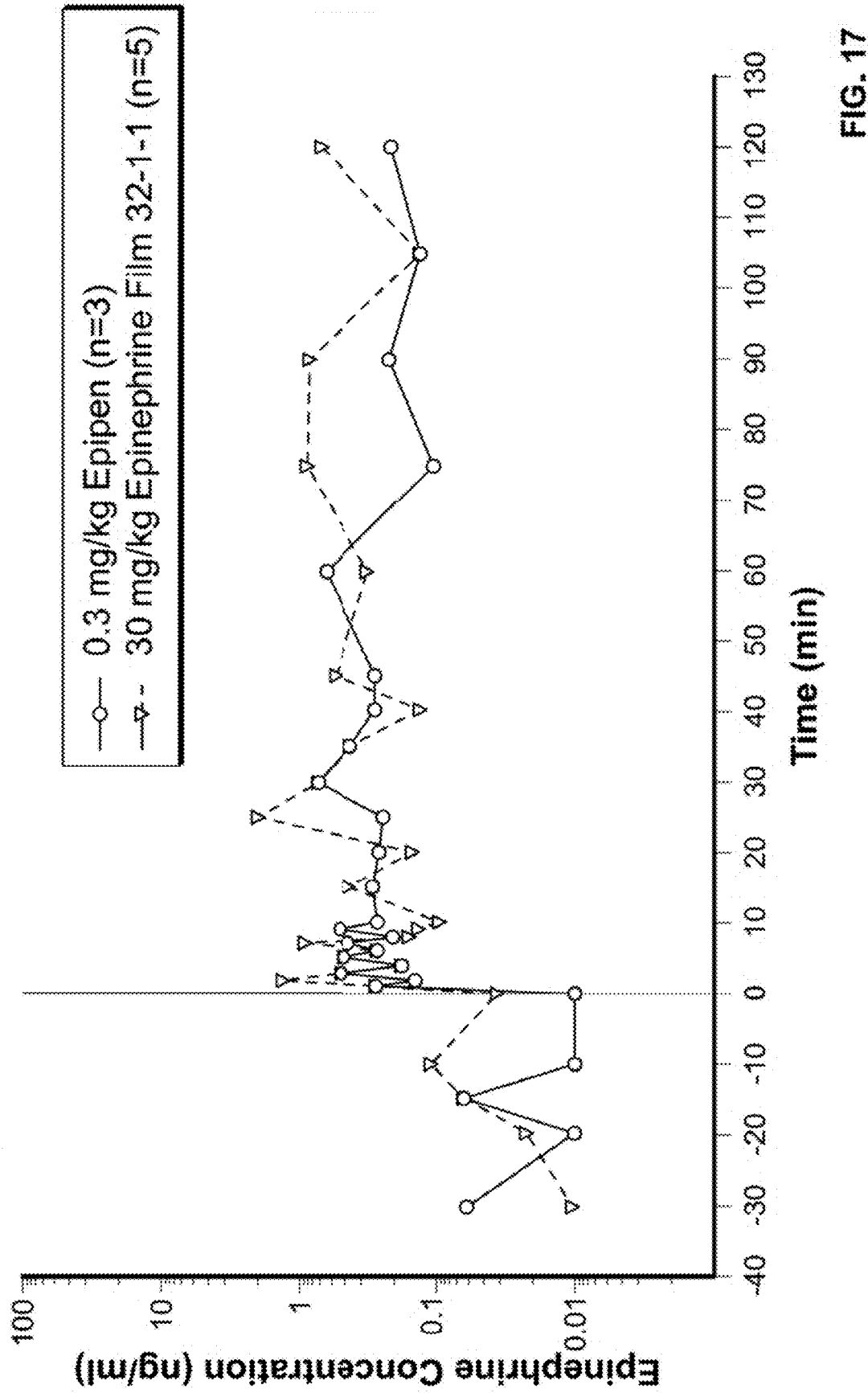
Referring to FIG. 17, this graph shows the impact of Farnesol in combination with Linoleic Acid on plasma concentration profiles of 40 mg epinephrine films vs. a 0.3 mg Epipen.

Referring to FIG. 17, this graph shows the impact of Farnesol in combination with Linoleic Acid on plasma concentration profiles of 40 mg Epinephrine Films vs. a 0.3 mg Epipen.

Figure 18:
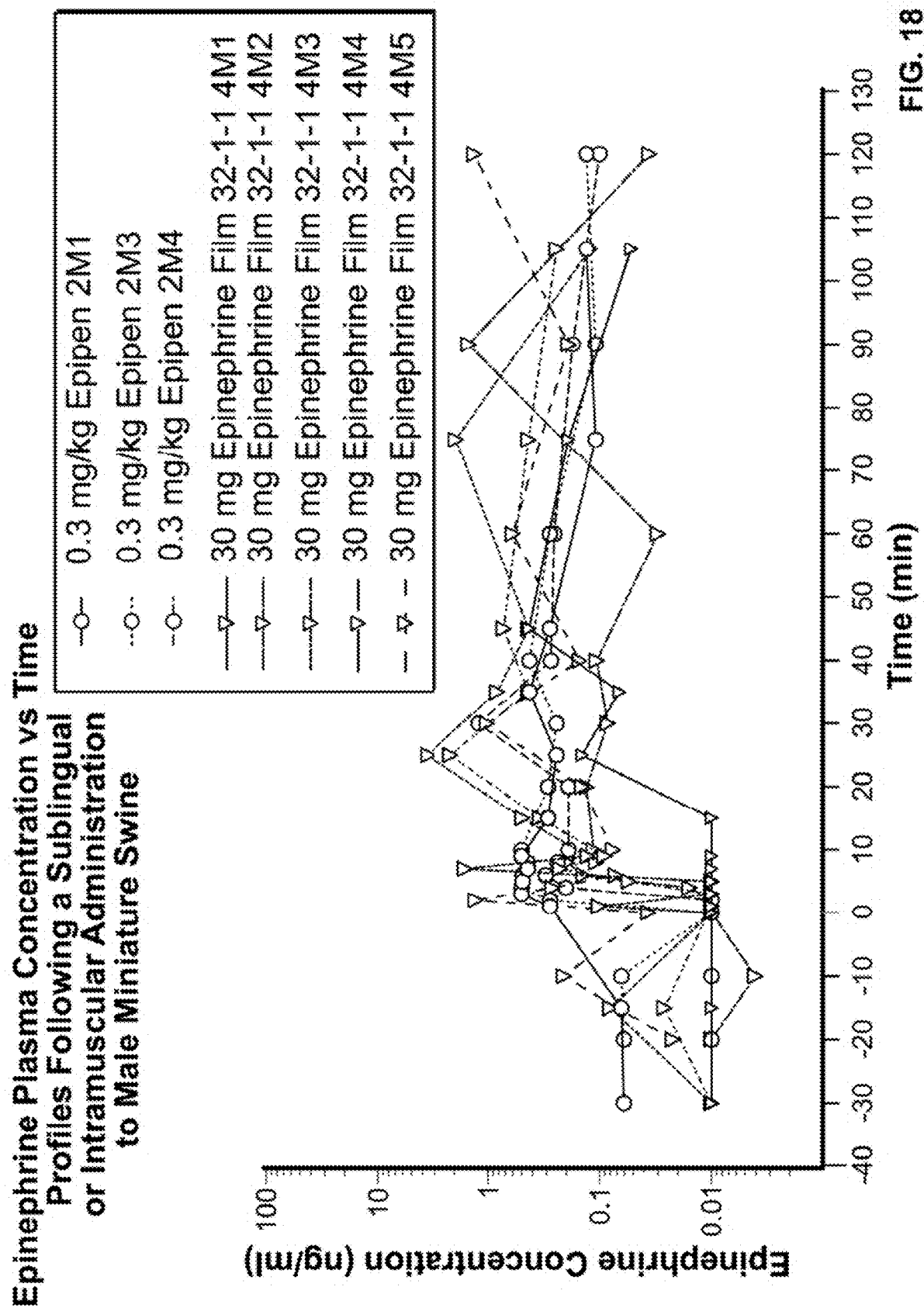
Referring to FIG. 18, this graph shows the impact of Farnesol and Farnesol in combination with Linoleic Acid on plasma concentration profiles of 40 mg Epinephrine Films vs. a 0.3 mg Epipen.

Referring to FIG. 18, this graph shows the impact of Farnesol and Farnesol in combination with Linoleic Acid on plasma concentration profiles of 40 mg Epinephrine Films vs. a 0.3 mg Epipen. The following examples are provided to illustrate pharmaceutical compositions, as well as, methods of making and using, pharmaceutical compositions and devices described herein.

EXAMPLES

Example 1

Permeation Enhancers—Epinephrine

Permeation enhancement was studied using a number of permeation enhancers with Epinephrine Bitartrate 16.00 mg/mL concentration. The results show flux enhancement represented in the data below. For 100% Eugenol and 100% Clove Oil, the results showed steady state flux reached significantly earlier along with an unexpectedly heightened % flux enhancement.

| Donor Solution (16.00 mg/mL Epinephrine Bitartrate + enhancer) | Average Steady State Flux (ug/cm2*min) | % Flux enhancement | Permeability Coefficient (cm/s) |
|---|---|---|---|
| Epinephrine Bitartrate, no enhancer | 1.3173 | N/A | 1.37E-06 |
| 3% Clove Oil | 8.2704 | 527.84 | 8.61E-06 |
| 3% Clove Oil Repeat | 5.3776 | 308.24 | 5.60E-06 |
| 3% Eugenol | 7.1311 | 441.35 | 7.43E-06 |
| 3% Eugenyl Acetate | 1.8945 | 43.82 | 1.97E-06 |
| 3% B-Caryophyllene | 3.5200 | 167.22 | 3.67E-06 |
| 0.3% Eugenol* | 3.9735 | 201.65 | 4.14E-06 |
| 100% Eugenol [1] | 36.8432 | 2696.92 | 3.84E-05 |
| 0.3% Clove Oil* | 3.6806 | 179.41 | 3.83E-06 |
| 100% Clove Oil [1] | 52.5304 | 3887.81 | 5.47E-05 |
| 3% Phenol | 4.5790 | 247.61 | 4.77E-06 |
| 3% Phenol Repeat | 4.1753 | 216.97 | 4.35E-06 |
| 3% Linoleic Acid | 2.1788 | 65.40 | 2.27E-06 |
| 50% Clove Oil | 2.5673 | 94.89 | 2.67E-06 |
| 0.3% Labrasol | 3.5221 | 167.38 | 3.67E-06 |
| 3% Vanillyl Alcohol + 6% Ethanol | 1.10243 | −16.31 | 1.15E-06 |
| 3% Safrole | 2.60634 | 97.86 | 2.71E-06 |
| 3% Oleic Acid | 2.06597 | 56.84 | 2.15E-06 |
| 3% Oleic Acid + 1% PEG200 | 2.73655 | 107.74 | 2.85E-06 |
| 3% Benzyl Alcohol | 1.38455 | 5.11 | 1.44E-06 |

[1] steady state flux reached at much earlier time point
*0.3% Eugenol vs 0.3% Clove—similar flux rates to one another For these examples, clove oil was obtained from clove leaf. Similar results may be obtained from clove oil from clove bud and/or clove stem. Based on this data, similar permeability enhancement results can be expected from pharmaceutical compounds structurally similar to epinephrine.

Example 2

General Permeation Procedure—Ex Vivo Permeation Study Protocol

In one example, a permeation procedure is conducted as follows. A temperature bath is set to 37° C., and receiver media is placed in a water bath to adjust the temperature and begin degassing. A franz diffusion cell is obtained and prepared. The franz diffusion cell includes a donor compound, a donor chamber, a membrane, sampling port, receptor chamber, stir bar, and a heater/circulator. A stir bar is inserted into a franz diffusion cell. Tissue is placed over the franz diffusion cell, and it is ensured that the tissue covers the entire area with an overlap onto a glass joint. The top of a diffusion cell is placed over the tissue, and the top of the cell is clamped to the bottom. About 5 mL of receptor media is loaded into the receiver area to ensure that no air bubbles are trapped in the received portion of the cell. This ensures that all 5 mL can fit into the receiver area. Stirring is begun, and temperature is allowed to equilibrate for about 20 minutes. Meanwhile, High Performance Liquid Chromatography (HPLC) vials are labelled by cell number and time point. One must then check again for air bubbles as the solution will degas during heating.

If testing films, one can perform the following next steps: (1) weigh films, punch to match diffusion area (or smaller), reweigh, record pre- and post-punching weight; (2) wet a donor area with approximately 100 μL of phosphate buffer; (3) place film on a donor surface, top with 400 μL of phosphate buffer, and start timers.

For solution studies, one can perform the following steps: (1) using a micropipette, dispense 500 μL of the solution into each donor cell, start the timers; (2) sample 200 μL at the following time points (time=0 min, 20 min, 40 min, 60 min, 120 min, 180 min, 240 min, 300 min, 360 min), and place in labelled HPLC vials, ensure no air is trapped in the bottom of the vial by tapping the closed vials; (3) replace each sample time with 200 μL of receptor media (to maintain 5 mL); (4) When all time points completed, disassemble the cells and dispose of all materials properly.

Example 3

Ex Vivo Permeation Evaluation

An exemplary ex vivo permeation evaluation is as follows.

1. Tissue is freshly excised and shipped (e.g. overnight) at 4° C.
2. The tissue is processed and frozen at −20° C. for up to three weeks prior to use.
3. The tissue is dermatomed to precise thickness.
4. Approximately 5 mL of receiving media is added to the receiving compartment. The media is selected to ensure sink conditions.
5. The tissue is placed in a franz diffusion cell, which includes a donor compound, a donor chamber, a membrane, sampling port, receptor chamber, stir bar, and a heater/circulator.
6. Approximately 0.5 mL of donor solution is applied or 8 mm circular film and wetted with 500 μL PBS buffer.
7. Samples are taken from the receiving chamber at given intervals and replaced with fresh media.

Example 4

Transbuccal Delivery of Doxepin

The following is an exemplary permeation study on the transbuccal delivery of doxepin. The studies were conducted under a protocol approved by the Animal Experimentation Ethics Committee of the University of Barcelona (Spain) and the Committee of Animal Experimentation of the regional autonomous government of Catalonia (Spain). Female pigs 3-4-months-old were used. The porcine buccal mucosa from the cheek region was excised immediately after the pigs were sacrificed in the animal facility at Bellvitge Campus (University of Barcelona, Spain) using an overdose of sodium thiopental anesthesia. The fresh buccal tissues were transferred from the hospital to the laboratory in containers filled with Hank's solution. The remaining tissue specimens were stored at −80° C. in containers with a PBS mixture containing 4% albumin and 10% DMSO as cryoprotective agents.

For the permeation studies, the porcine buccal mucosa was cut to 500+/−50 µm thick sheets, which contributes to the diffusional barrier (Buccal bioadhesive drug delivery—A promising option for orally less efficient drugs Sudhakar et al., *Journal of Controlled Release* 114 (2006) 15-40), using an electric dermatome (GA 630, Aesculap, Tuttlingen, Germany) and trimmed with surgical scissors in adequate pieces. The majority of the underlying connective tissue was removed with a scalpel.

Membranes were then mounted in specially designed membrane holders with a permeation orifice diameter of 9 mm (diffusion area 0.636 cm$^2$). Using the membrane holder, each porcine buccal membrane was mounted between the donor (1.5 mL) and the receptor (6 mL) compartments with the epithelium side facing the donor chamber and the connective tissue region facing the receiver of static Franz-type diffusion cells (Vidra Foc Barcelona, Spain) avoiding bubbles formation.

Infinite dose conditions were ensured by applying 100 µL as donor solution of a saturated doxepin solution into the receptor chamber and sealed by Parafilm immediately to prevent water evaporation. Prior to conducting the experiments, the diffusion cells were incubated for 1 h in a water bath to equalize the temperature in all cells (37°+/−° C.). Each cell contained a small Teflon1 coated magnetic stir bar which was used to ensure that the fluid in the receptor compartment remained homogenous during the experiments.

Sink conditions were ensured in all experiments by initial testing of doxepin saturation concentration in the receptor medium. Samples (300 µL) were drawn via syringe from the center of the receptor compartment at pre-selected time intervals (0.1, 0.2, 0.3, 0.7, 1, 2, 3, 4, 5 and 6 h) for 6 h. The removed sample volume was immediately replaced with the same volume of fresh receptor medium (PBS; pH 7.4) with great care to avoid trapping air beneath the membrane. Additional details can be found in A. Gimemo, et al. Transbuccal delivery of doxepin: Studies on permeation and histological evaluation, *International Journal of Pharmaceutics* 477 (2014), 650-654, which is incorporated by reference herein.

Example 5

Oral Transmucosal Delivery

Porcine oral mucosal tissue has similar histological characteristics to human oral mucosal tissue (Heaney T G, Jones R S, Histological investigation of the influence of adult porcine alveolar mucosal connective tissues on epithelial differentiation. *Arch Oral Biol* 23 (1978) 713-717, Squier C A, and Collins P, The relationship between soft tissue attachment, epithelial downgrowth and surface porosity. *Journal of Periodontal Research* 16 (1981) 434-440). Lesch et al. (The Permeability of Human Oral Mucosa and Skin to Water, *J Dent Res* 68 (9), 1345-1349, 1989) reported that the water permeability of porcine buccal mucosa was not significantly different from human buccal mucosa but the floor of the mouth was more permeable in human tissue than in pig tissue. Comparisons between fresh porcine tissue specimens and those stored at −80° C. revealed no significant effect on permeability as a result of freezing. Porcine buccal mucosal absorption has been studied for a wide range of drug molecules both in vitro and in vivo (see, e.g., Table 1 of M. Sattar, Oral transmucosal drug delivery—current status and future prospects, *International Journal of Pharmaceutics* 471 (2014) 498-506), which is incorporated by reference herein. Typically, in vitro studies involve mounting excised porcine buccal tissue in Ussing chambers, Franz cells or similar diffusion apparatus. The in vivo studies described in the literature involve the application of the drug as a solution, gel or composition to the buccal mucosa of pigs followed by plasma sampling.

Nicolazzo et al. (The Effect of Various in Vitro Conditions on the Permeability Characteristics of the Buccal Mucosa, Journal of Pharmaceutical Sciences 92(12) (2002) 2399-2410) investigated the effects of various in vitro conditions on the permeability of porcine buccal tissue using caffeine and oestradiol as model hydrophilic and lipophilic molecules. Drug permeation in the buccal mucosa was studied using modified Ussing chambers. Comparative permeation studies were performed through full thickness and epithelial tissues, fresh and frozen tissues. Tissue integrity was monitored by the absorption of the fluorescein isothiocyanate (FITC)-labeled dextran 20 kDa (FD20) and tissue viability was assessed using an MTT (3-[4,5-dimethylthiazol-2-yl]-2,5-diphenyltetrazolium bromide) biochemical assay and histological evaluation. Permeability through the buccal epithelium was 1.8-fold greater for caffeine and 16.7-fold greater for oestradiol compared with full thickness buccal tissue. Flux values for both compounds were comparable for fresh and frozen buccal epithelium although histological evaluation demonstrated signs of cellular death in frozen tissue. The tissue appeared to remain viable for up to 12 h postmortem using the MTT viability assay which was also confirmed by histological evaluation.

Kulkarni et al. investigated the relative contributions of the epithelium and connective tissue to the barrier properties of porcine buccal tissue. In vitro permeation studies were conducted with antipyrine, buspirone, bupivacaine and caffeine as model permeants. The permeability of the model diffusants across buccal mucosa with thickness of 250, 400, 500, 600, and 700 µm was determined. A bilayer membrane model was developed to delineate the relative contribution to the barrier function of the epithelium and the connective tissue. The relative contribution of the connective tissue region as a permeability barrier significantly increased with increasing mucosal tissue thickness. A mucosal tissue thickness of approximately 500 µm was recommended by the authors for in vitro transbuccal permeation studies as the epithelium represented the major permeability barrier for all diffusants at this thickness. The authors also investigated the effects of a number of biological and experimental variables on the permeability of the same group of model permeants in porcine buccal mucosa (Porcine buccal mucosa as in vitro model: effect of biological and experimental variables, Kulkarni et al., *J Pharm Sci.* 2010 99(3):1265-77). Significantly, higher permeability of the permeants was observed for the thinner region behind the lip (170-220 μm) compared with the thicker cheek (250-280 μm) region. Porcine buccal mucosa retained its integrity in Kreb's bicarbonate ringer solution at 4° C. for 24 h. Heat treatment to separate the epithelium from underlying connective tissue did not adversely affect its permeability and integrity characteristics compared with surgical separation.

Additional details can be found at M. Sattar, Oral transmucosal drug delivery—current status and future prospects, *International Journal of Pharmaceutics* 471 (2014) 498-506, which is incorporated by reference herein.

Example 6

Cryopreservation of Buccal Mucosa

Different areas of porcine buccal mucosa have different pattern of permeability, there is significantly higher permeability in the region behind the lips in comparison to cheek region, because in porcine buccal mucosa, the epithelium acts as a permeability barrier, and the thickness of the cheek epithelium is greater than that of the region behind the lips (Harris and Robinson, 1992). In exemplary permeation studies, the fresh or frozen porcine buccal mucosa from the same area was cut to 500±50 μm thick sheets, which contributes to the diffusional barrier (Sudhakar et al., 2006), were obtained using an electric dermatome (model GA 630, Aesculap, Tuttlingen, Germany) and trimmed with surgical scissors in adequate pieces. All devices utilized were previously sterilized. The majority of the underlying connective tissue was removed with a scalpel. Membranes were then mounted in specially designed membrane holders with a permeation orifice diameter of 9 mm (diffusion area 0.63 cm). Using the membrane holder, each porcine buccal membrane was mounted between the donor (1.5 mL) and the receptor (6 mL) compartments with the epithelium facing the donor chamber and the connective tissue region facing the receiver of static Franz-type diffusion cells (Vidra Foc, Barcelona, Spain) avoiding bubbles formation. Experiments were performed using PP, which has lipophilic characteristics (log P=1.16; n-octanol/PBS, pH 7.4), ionisable (pKa=9.50) and a MW=259.3 g/mol, as a model drug (Modamio et al., 2000).

Infinite dose conditions were ensured by applying 300 μL as a donor solution of a saturated solution of PP (CO=588005±5852 μg/mL at 37°±1° C., n=6), in PBS (pH 7.4) into the receptor chamber and sealed by Parafilm immediately to prevent water evaporation.

Prior to conducting the experiments, the diffusion cells were incubated for 1 h in a water bath to equilibrate the temperature in all cells (37°±1 C). Each cell contained a small Teflon coated magnetic stir bar which was used to ensure that the fluid in the receptor compartment remained homogenous during the experiments. Sink conditions were ensured in all experiments after initial testing of PP saturation concentration in the receptor medium.

Samples (300 μL) were drawn via syringe from the center of the receptor compartment at the following time intervals: 0.25, 0.5, 1, 2, 3, 4, 5 and 6 h. The removed sample volume was immediately replaced with the same volume of fresh receptor medium (PBS; pH 7.4) with great care to avoid trapping air beneath the dermis. Cumulative amounts of the drug (μg) penetrating the unit surface area of the mucosa membrane ($cm^2$) were corrected for sample removal and plotted versus time (h). The diffusion experiments were carried out 27 times for the fresh and 22 times for the frozen buccal mucosa.

Additional details can be found at S. Amores, An improved cryopreservation method for porcine buccal mucosa in ex vivo drug permeation studies using Franz diffusion cells, *European Journal of Pharmaceutical Sciences* 60 (2014) 49-54.

Example 7

Permeation of Quinine Across Sublingual Mucosa Sections

Since porcine and human oral membranes are similar in composition, structure and permeability measurements, porcine oral mucosa is a suitable model for human oral mucosa. Permeability across the porcine oral mucosa is not metabolically linked therefore it is not important for the tissue to be viable.

To prepare the porcine membranes, porcine floor of mouth and ventral (underside) tongue mucosa membranes were excised by blunt dissection using a scalpel. The excised mucosa were cut into approximately 1 cm squares and frozen on aluminium foil at −20° C. until used (<2 weeks). For non-frozen ventral surface of porcine tongue, the mucosa was used in the permeation studies within 3 h of excision.

The permeability of the membranes to quinine was determined using all-glass Franz diffusion cells with a nominal receptor volume of 3.6 mL and diffusional area of 0.2 $cm^2$. The cell flanges were greased with high performance vacuum grease and the membranes mounted between the receptor and donor compartments, with the mucosal surface uppermost. Clamps were used to hold the membranes into position before the receptor compartments were filled with degassed phosphate buffered saline (PBS), pH 7.4. Micromagnetic stirrer bars were added to the receptor compartments and the complete cells were placed in a water bath at 37° C. The membranes were equilibrated with PBS applied to the donor compartments for 20 min before being aspirated with a pipette. Aliquots of 5 μL of the quinine solution or 100 μL of the saturated solutions of Q/2-HP-β-CD complex in different vehicles were applied to each of the donor compartments. In the study to determine the effect of saliva on the permeation of quinine across the ventral surface of the tongue, 100 μL of sterile saliva was added to the donor compartments before adding 5 μL of the quinine solution.

At 2, 4, 6, 8, 10 and 12 h, the receptor phases were withdrawn from the sampling ports and aliquots of 1 mL samples were transferred to HPLC autosampler vials, before being replaced with fresh PBS stored at 37° C. Apart from the studies involving Q/2-HP-β-CD saturated solutions (where an infinite dose was applied at the start of the experiments), 5 μL of the respective quinine solution was reapplied to the donor phase up to 10 h. The purpose of this was to represent a hypothetical in-use finite dosing regimen based upon an interval of 2 h between doses. At least 3 replicates were carried out for each study.

Additional details can be found at C. Ong, Permeation of quinine across sublingual mucosa, in vitro, *International Journal of Pharmaceutics* 366 (2009) 58-64.

Example 8

Ex-Vivo Initial Study—Form of the API

In this example, the permeation of Epinephrine Base was tested—solubilized in situ vs. the inherently soluble Epinephrine Bitartrate and no differences were found. Epinephrine Bitartrate was selected for further development based on ease of processing. Flux was derived as slope of the amount permeated as a function of time. Steady state flux extrapolated from the plateau of flux vs time curve multiplied by the volume of receiver media. The graph in FIG. 2A shows average amount permeated vs. time, with 8.00 mg/mL Epinephrine bitartrate and 4.4 mg/mL Epinephrine base solubilized. The graph in FIG. 2B shows average flux vs. time, with 8.00 mg/mL Epinephrine bitartrate and 4.4 mg/mL Epinephrine base solubilized.

| Donor Solution | Average Steady State Flux (ug/cm2*min) |
|---|---|
| Epinephrine Base (conc 4.4 mg/mL) | 0.512 |
| Epinephrine Bitartrate (conc 8.00 mg/mL) | 0.466 |

Example 9

Concentration Dependence on Permeation/Flux

In this study, ex-vivo permeation of Epinephrine Bitartrate as a function of concentration was studied. FIG. 3 shows ex-vivo permeation of epinephrine bitartrate as a function of concentration. The study compared concentrations of 4 mg/mL, 8 mg/mL, 16 mg/mL and 100 mg/mL. Results showed that increasing concentration resulted in increased permeation, and level of enhancement diminishes at higher loading. The study compared concentrations of 4 mg/mL, 8 mg/mL, 16 mg/mL and 100 mg/mL.

| Donor Solution | Average Steady State Flux (ug/cm2*min) |
|---|---|
| Epinephrine Bitartrate (conc 4 mg/mL) | 0.167 |
| Epinephrine Bitartrate (conc 8 mg/mL) | 0.466 |
| Epinephrine Bitartrate (conc 16 mg/mL)* | 1.317 |
| Epinephrine Bitartrate (conc 100 mg/mL) | 2.942 |

| Donor Solution | Ratio of enhancement | Theoretical enhancement |
|---|---|---|
| Epinephrine Bitartrate (4.00 mg/mL) | N/A | N/A |
| Epinephrine Bitartrate (8.00 mg/mL) | 2.8 | 2 |
| Epinephrine Bitartrate (16.00 mg/mL) | 7.9 | 4 |
| Epinephrine Bitartrate (100.00 mg/mL) | 17.6 | 25 |

Example 10

Influence of pH

In this example, the permeation of Epinephrine Bitartrate as a function of solution pH was studied. In this example, acidic conditions were explored for the ability to promote stability. The results showed that pH 5 was slightly more favorable as compared to pH 3. The inherent pH of epinephrine bitartrate in solution in the concentration ranges explored is 4.5-5. No pH adjustment with buffers was required.

FIG. 4 shows permeation of epinephrine bitartrate as a function of solution pH. Acidic conditions were explored to promote stability. The results compared Epinephrine Bitartrate pH 3 buffer and Epinephrine Bitartrate pH 5 buffer, and found that the Epinephrine Bitartrate pH 5 buffer was slightly favorable.

Example 11

Influence of Enhancers on Permeation of Epinephrine

In this example, the permeation of epinephrine to test for transmucosal delivery was studied as the amount permeated (μg) vs. time (in minutes). The following enhancers were screened for concentration effects in a solution containing 16.00 mg/mL Epinephrine. The graph on FIG. 5 demonstrates the results of these enhancers as a function of time.

| Legend | Enhancer | Average Steady State Flux (μg/cm2*min) | Percent Enhancement |
|---|---|---|---|
| No Enhancer | None | 1.317 | N/A |
| Enhancer A | 3% Labrasol Caprylocaproyl polyoxyl-8 glycerides | 5.208 | 395 |
| Enhancer B | 3% Propylene glycol monocaprylate | 2.385 | 181 |
| Enhancer C | 3% Polyglyceryl-3 oleate | 1.482 | 112 |
| Enhancer D | 3% Oleoyl polyoxyl-6 glycerides | 0.281 | 21 |
| Enhancer E | 3% TDM | 2.642 | 201 |
| Enhancer F | 3% SGDC | 0.342 | 26 |
| Enhancer G | 3% Lauroyl polyoxyl-32 glycerides | 1.641 | 125 |
| Enhancer H | 3% Ethanol | 0.163 | 12 |
| Enhancer I | 6% Ethanol | 0.254 | 19 |
| Enhancer J | 6% Labrasol Caprylocaproyl polyoxyl-8 glycerides | 4.444 | 337 |
| Enhancer K | 6% Polyglyceryl-3 oleate | 0.306 | 23 |
| Enhancer L | 3% clove oil | 8.216 | 624 |

Enhancers were selected and designed with functionality influencing different barriers in the mucosa. While all tested enhancers did improve the amount permeated over time, clove oil and Labrasol, in particular have shown significantly and unexpectedly high enhancement of permeation.

| | Time (min) | set 2 (A, B, C) average amount permeated | std dev set 2 amount perm | set 2 (D, E, F) average flux (μg/cm2*min) | std dev set 2 | steady state flux average |
|---|---|---|---|---|---|---|
| 8.00 mg/0.500 mL | 30 | 0 | 0 | 0 | 0 | |
| 40 mg/strip | 45 | 2.5 | 4.33012702 | 0.260416667 | 0.4510549 | 1.317274 |
| no enhancer | 60 | 5.5 | 7.08872344 | 0.3125 | 0.3125 | |
| | 120 | 31.33333333 | 26.1549868 | 0.672743056 | 0.5050226 | |
| | 180 | 72.66666667 | 58.215834 | 1.076388889 | 0.8496863 | |
| | 240 | 112.1666667 | 80.1878004 | 1.028645833 | 0.5733604 | |
| | 300 | 160.1666667 | 103.254943 | 1.25 | 0.6036108 | |
| | 360 | 213.3333333 | 131.305306 | 1.384548611 | 0.7308311 | |

| | Time (min) | set 1 (A, B, C) average amount permeated (ug) | std dev set 1 amount perm | set 1 (A, B, C) average flux (μg/cm2*min) | std dev set 1 | steady state flux average |
|---|---|---|---|---|---|---|
| 8.00 mg/0.500 mL | 0 | 0 | 0 | 0 | 0 | |
| 40 mg/strip | 30 | 0.5 | 0.8660254 | 0.026041667 | 0.0451055 | 5.208333 |
| Labrasol | 45 | 2.666666667 | 0.28867513 | 0.225694444 | 0.0601407 | |
| | 60 | 4 | 1.80277564 | 0.138888889 | 0.1674245 | |
| | 120 | 28 | 16.3935963 | 0.625 | 0.3836177 | |
| | 180 | 98 | 53.3291665 | 1.822916667 | 0.9701176 | |
| | 240 | 238.1666667 | 93.0017921 | 3.650173611 | 1.136722 | |
| | 300 | 421.1666667 | 115.153521 | 4.765625 | 0.6675003 | |
| | 360 | 638.1666667 | 130.709921 | 5.651041667 | 0.4732495 | |

| | Time (min) | set 2 (A, B, C) average amount permeated | std dev set 2 amount perm | set 2 (D, E, F) average flux (μg/mL*min) | std dev set 2 | steady state flux average |
|---|---|---|---|---|---|---|
| 8.00 mg/0.500 mL | 0 | 0 | 0 | 0 | 0 | |
| 40 mg/strip | 30 | 0.00 | 0 | 0 | 0 | |
| capryol 90 | 45 | 0.00 | 0 | 0 | 0 | 1.931424 |
| | 60 | 0.00 | 0 | 0 | 0 | |
| | 120 | 9.17 | 5.79511288 | 0.238715278 | 0.1509144 | |
| | 180 | 38.67 | 16.7655401 | 0.768229167 | 0.2864583 | |
| | 240 | 88.50 | 30.2654919 | 1.297743056 | 0.4018216 | |
| | 300 | 150.67 | 39.6936183 | 1.618923611 | 0.3269068 | |
| | 360 | 236.83 | 51.9358579 | 2.243923611 | 0.4999616 | |

| | Time (min) | set 2 (A, B, C) average amount permeated | std dev set 2 amount perm | set 2 (D, E, F) average flux (μg/mL*min) | std dev set 2 | steady state flux average |
|---|---|---|---|---|---|---|
| 8.00 mg/0.500 mL | 0 | 0.8 | 1.78885438 | 0 | 0 | |
| 40 mg/strip | 30 | 10.80 | 13.325727 | 0.520833333 | 0.7186273 | |
| plurol oleique | 45 | 20.90 | 22.1624683 | 1.052083333 | 0.9356173 | 1.481771 |
| | 60 | 33.00 | 30.8058436 | 1.260416667 | 0.9319861 | |
| | 120 | 90.70 | 68.1951245 | 1.502604167 | 1.005753 | |
| | 180 | 157.00 | 107.373763 | 1.7265625 | 1.0427891 | |
| | 240 | 239.80 | 140.586539 | 2.15625 | 1.2085059 | |
| | 300 | 285.60 | 184.236397 | 1.192708333 | 1.484335 | |
| | 360 | 353.60 | 221.81676 | 1.770833333 | 0.993644 | |

| | Time (min) | set 2 (A, B, C) average amount permeated | std dev set 2 amount perm | set 2 (D, E, F) average flux (μg/mL*min) | std dev set 2 | steady state flux average |
|---|---|---|---|---|---|---|
| 8.00 mg/0.500 mL | 0 | 0.00 | 0.00 | 0.00 | 0.00 | |
| 40 mg/strip | 20 | 0.00 | 0.00 | 0.00 | 0.00 | |
| TDM | 40 | 3.00 | 2.43 | 0.23 | 0.32 | 2.642144 |
| | 60 | 8.83 | 4.86 | 0.46 | 0.35 | |
| | 120 | 41.33 | 15.08 | 0.85 | 0.49 | |
| | 180 | 99.75 | 30.17 | 1.52 | 0.79 | |
| | 240 | 179.92 | 48.30 | 2.09 | 0.98 | |
| | 300 | 276.92 | 72.35 | 2.53 | 1.19 | |
| | 360 | 382.83 | 102.02 | 2.76 | 1.38 | |

| | Time (min) | set 2 (A, B, C) average amount permeated | std dev set 2 amount perm | set 2 (D, E, F) average flux (μg/mL*min) | std dev set 2 | steady state flux average |
|---|---|---|---|---|---|---|
| 8.00 mg/0.500 mL | 0 | 0 | 0 | 0 | 0 | |
| 40 mg/strip | 30 | 0.00 | 0 | 0 | 0 | |

|  | Time (min) | set 2 (A, B, C) average amount permeated | std dev set 2 amount perm | set 2 (D, E, F) average flux (µg/mL*min) | std dev set 2 | steady state flux average |
|---|---|---|---|---|---|---|
| SGDC | 45 | 0.67 | 1.30384048 | 0.069444444 | 0.1261521 | 0.341797 |
|  | 60 | 1.58 | 1.94935887 | 0.095486111 | 0.1063147 |  |
|  | 120 | 7.00 | 9.44325156 | 0.141059028 | 0.1910856 |  |
|  | 180 | 16.17 | 22.0323626 | 0.238715278 | 0.316132 |  |
|  | 240 | 28.58 | 37.6191441 | 0.323350694 | 0.3977149 |  |
|  | 300 | 43.00 | 54.3927844 | 0.375434028 | 0.4112124 |  |
|  | 360 | 54.83 | 65.7976063 | 0.308159722 | 0.3008536 |  |

|  | Time (min) | set 2 (A, B, C) average amount permeated | std dev set 2 amount perm | set 2 (D, E, F) average flux (µg/mL*min) | std dev set 2 | steady state flux average |
|---|---|---|---|---|---|---|
| 8.00 mg/0.500 mL | 0 | 0.8 | 1.15108644 | 0 | 0 |  |
| 40 mg/strip | 30 | 1.10 | 1.51657509 | 0.015625 | 0.0232924 |  |
| Labrafil | 45 | 1.10 | 1.51657509 | 0 | 0 | 0.28125 |
|  | 60 | 1.10 | 1.51657509 | 0 | 0 |  |
|  | 120 | 4.00 | 4.89897949 | 0.075520833 | 0.0984775 |  |
|  | 180 | 9.10 | 10.9167303 | 0.1328125 | 0.1671035 |  |
|  | 240 | 15.20 | 18.7169709 | 0.158854167 | 0.2034753 |  |
|  | 300 | 25.70 | 29.8487856 | 0.2734375 | 0.2910091 |  |
|  | 360 | 36.80 | 43.3093523 | 0.2890625 | 0.3532943 |  |

|  | Time (min) | set 2 (A, B, C) average amount permeated | std dev set 2 amount perm | set 2 (D, E, F) average flux (µg/mL*min) | std dev set 2 | steady state flux average |
|---|---|---|---|---|---|---|
| 8.00 mg/0.500 mL | 0 | 0 | 0 | 0 | 0 |  |
| 40 mg/strip | 20 | 0.33 | 0.89442719 | 0.026041667 | 0.0637888 |  |
| Gelucire 44/14 | 40 | 3.83 | 5.94138031 | 0.2734375 | 0.378725 | 1.629774 |
|  | 60 | 11.50 | 17.1850225 | 0.598958333 | 0.8405853 |  |
|  | 120 | 41.58 | 48.5059275 | 0.783420139 | 0.8042794 |  |
|  | 180 | 91.92 | 82.5124233 | 1.310763889 | 0.9525224 |  |
|  | 240 | 150.17 | 118.949569 | 1.516927083 | 0.9914576 |  |
|  | 300 | 217.50 | 158.792947 | 1.753472222 | 1.0756081 |  |
|  | 360 | 275.33 | 189.967563 | 1.506076389 | 0.9083155 |  |

|  | Time (min) | set 2 (A, B, C) average amount permeated | std dev set 2 amount perm | set 2 (D, E, F) average flux (µg/cm2*min) | std dev set 2 | steady state flux average |
|---|---|---|---|---|---|---|
| 8.00 mg/0.500 mL | 0 | 0 | 0 | 0 | 0 |  |
| 40 mg/strip | 20 | 0 | 0 | 0 | 0 |  |
| clove oil | 40 | 28.66666667 | 27.360251 | 2.239583333 | 2.1375196 | 8.270399 |
|  | 60 | 96.5 | 79.5424415 | 5.299479167 | 4.0954816 |  |
|  | 120 | 389.6666667 | 278.072533 | 7.634548611 | 5.2070528 |  |
|  | 180 | 688.6666667 | 451.678628 | 7.786458333 | 4.5210426 |  |
|  | 240 | 1009.166667 | 603.252089 | 8.346354167 | 3.9590828 |  |
|  | 300 | 1333.5 | 759.653046 | 8.446180556 | 4.1168559 |  |
|  | 360 | 1644.333333 | 878.2762 | 8.094618056 | 3.2301203 |  |

|  | Time (min) | set 2 (A, B, C) average amount permeated | std dev set 2 amount perm | set 2 (D, E, F) average flux (µg/mL*min) | std dev set 2 | steady state flux average |
|---|---|---|---|---|---|---|
| 8.00 mg/0.500 mL | 0 | 0 | 0 | 0 | 0 |  |
| 40 mg/strip | 20 | 0 | 0 | 0 | 0 | 3.161892 |
| 3% Labrasol + | 40 | 1.666666667 | 2.88675135 | 0.130208333 | 0.2255274 |  |

-continued

| | Time (min) | set 2 (A, B, C) average amount permeated | std dev set 2 amount perm | set 2 (D, E, F) average flux (µg/mL*min) | std dev set 2 | steady state flux average |
|---|---|---|---|---|---|---|
| 1% TDM | 60 | 6.833333333 | 11.8356805 | 0.403645833 | 0.6991351 | |
| | 120 | 68.83333333 | 92.6907942 | 1.614583333 | 2.1084505 | |
| | 180 | 103.6666667 | 101.539812 | 0.907118056 | 0.3351021 | |
| | 240 | 180 | 130.184484 | 1.987847222 | 0.7476876 | |
| | 300 | 291.5 | 149.81572 | 2.903645833 | 0.5193664 | |
| | 360 | 422.8333333 | 164.032263 | 3.420138889 | 0.5530917 | |

Example 12

Impact of Enhancers on Epinephrine Release

Release profiles of epinephrine were studied to determine the impact of enhancers (Labrasol and clove oil) on epinephrine release. FIG. 6A shows the epinephrine release from different polymer platforms. FIG. 6B shows the impact of enhancers on epinephrine release. The results showed that the amount permeated leveled off after about 40 minutes to be between approximately 3250 and 4250 µg. The tested enhancers were shown not to restrict the release of epinephrine from the matrix.

Example 13

Accelerated Stability

The stabilizer loading variants were tested.

| Time (weeks) @ 40° C./ 75% R.H. | Formulation 10 EPI mg/film | Formulation 10 with 0.25% Stabilizer EPI mg/film | Formulation 10 with 1% Stabilizer EPI mg/film |
|---|---|---|---|
| 0 | 39.3 | 37.9 | 38.3 |
| 2 | 35.2 | 36.8 | 34.7 |
| 4 | 38.2 | 36.8 | 36.2 |
| 8 | 37.7 | 35.6 | 35.1 |
| 12 | 36.1 | 35.4 | 35.1 |

Example 14

Impact of Enhancer

A pharmacokinetic model in the male Yucatan, miniature swine was studied. The graph on FIG. 7 shows the results of a pharmacokinetic model in the male Yucatan, miniature swine. The study compares a 0.3 mg Epipen, a 0.12 mg Epinephrine IV and a placebo.

The impact of no enhancer is shown in FIG. 8 on the concentration profiles of a 0.3 mg Epipen and a 40 mg Epinephrine film with no enhancer The impact of enhancer 3% Labrasol is shown in FIG. 9, which shows the impact of Enhancer A (Labrasol) on the concentration profiles of a 40 mg Epinephrine film vs. a 0.3 mg Epipen. FIG. 10 shows the impact of Enhancer L (clove oil) on the concentration profiles of two 40 mg Epinephrine films (10-1-1) and (11-1-1) vs. a 0.3 mg Epipen.

In addition, the influence of film dimensions and impact of clove oil (3%) is also shown in FIG. 11. This study was carried out comparing 0.30 mg EpiPen (n=4), a 40 mg Epinephrine Film (10-1-1) (n=5) and a 40 mg Epinephrine Film (11-1-1) (n=5). The concentration vs. time profiles followed subligual or intramuscular epinephrine administration to male miniature swine.

Studies were performed to vary the ratio of ephinephrine to an enhancer. These studies were also concentration vs. time profiles following subligual or intramuscular epinephrine administration to male miniature swine. Varying the ratio of Epinephrine to clove oil (Enhancer L) produced the results shown in FIG. 12. This study was carried out comparing 0.30 mg EpiPen (n=4), a 40 mg Epinephrine Film (12-1-1) (n=5) and a 20 mg Epinephrine Film (13-1-1) (n=5).

Example 15

A varying dose was carried out in constant matrix with enhancer Labrasol (3%) and clove oil (3%) are shown in FIGS. 13 and 14 respectively. The study in FIG. 13 was carried out comparing 0.30 mg EpiPen (n=4), a 40 mg Epinephrine Film (18-1-1) (n=5) and a 30 mg Epinephrine Film (20-1-1) (n=5). The study in FIG. 14 was carried out comparing 0.30 mg EpiPen (n=4), a 40 mg Epinephrine Film (19-1-1) (n=5) and a 30 mg Epinephrine Film (21-1-1) (n=5). These studies were also concentration vs. time profiles following subligual or intramuscular epinephrine administration to male miniature swine.

Example 16

A pharmacokinetic model in the male miniature swine was studied to determine the impact of an enhancer (farnesol) on epinephrine concentration over time. The graph on FIG. 15 shows the epinephrine plasma concentration (in ng/mL) as a function of time (in minutes) following sublingual or intramuscular administration of a farnesol permeation enhancer. This study compares a 0.3 mg Epipen (n=3), a 30 mg Epinephrine Film 31-1-1 (n=5) and a 30 mg Epinephrine Film 32-1-1 (n=5) each Epinephrine Film being formulated with a farnesol enhancer. As shown in this figure, the 31-1-1 film demonstrates enhanced stability of epinephrine concentration starting at about 30-40 minutes until approximately 130 minutes.

The graph in FIG. 16 is taken from the same study as FIG. 17, but shows exclusively the data points comparing the 0.3 mg Epipen against the 30 mg Epinephrine Film 31-1-1 (n=5).

The graph in FIG. 17 is taken from the same study as FIG. 17, but shows exclusively the data points comparing the 0.3 mg Epipen against the 30 mg Epinephrine Film 32-1-1 (n=5).

Example 17

Referring to FIG. 18, this graph shows a pharmacokinetic model in the male miniature swine was studied to determine the impact of an enhancer (farnesol) on epinephrine concentration over time following sublingual or intramuscular administration. The epinephrine plasma concentration (in ng/mL) is shown as a function of time (in minutes) following sublingual or intramuscular administration of a farnesol permeation enhancer in Epinephrine films. The study compared data from three 0.3 mg Epipens against five 30 mg Epinephrine films (32-1-1). The data shows the Epinephrine films film having enhanced stability of epinephrine concentration starting at about 20-30 minutes until approximately 130 minutes.

Example 18

In one embodiment, an epinephrine pharmaceutical composition film can be made with the following formulation:

|  | Formulation A | | |
| --- | --- | --- | --- |
| MATERIAL | WT % dry | WT % wet | mg/Strip |
| EPINEPHRINE bitartrate | 46.40 | 18.56 | 54.56 |
| hydroxypropylmethyl cellulose | 11.54 | 4.61 | 13.57 |
| polyvinyl pyrrolidone | 27.92 | 11.17 | 32.84 |
| Glycerol monooleate | 0.58 | 0.23 | 0.68 |
| Polyethylene Oxide | 1.16 | 0.46 | 1.36 |
| Polysorbate | 0.58 | 0.23 | 0.68 |
| Phytoextract | 9.98 | 3.99 | 9.97 |
| Stabilizer | 0.12 | 0.05 | 0.14 |
| Buffer | 0.58 | 0.23 | 0.68 |
| Artificial sweetener | 1.16 | 0.46 | 1.36 |
| Linoleic acid | 0.0037 | 0.00 | 0.00 |
| Farnesol | | | |
| Yellow # 5 | | | |
| TOTAL | 100.00 | 40.00 | 115.84 |

Example 19

An epinephrine pharmaceutical film compositions was made with the following formulation:

|  | Formulation B | | |
| --- | --- | --- | --- |
| MATERIAL | WT % dry | WT % wet | mg/Strip |
| EPINEPHRINE bitartrate | 46.17 | 18.47 | 54.29 |
| Hydroxypropylmethyl cellulose | 11.48 | 4.59 | 13.50 |
| Polyvinyl pyrrolidone | 27.78 | 11.11 | 32.67 |
| Glycerol monooleate | 0.58 | 0.23 | 0.68 |
| Polyethylene Oxide | 1.15 | 0.46 | 1.35 |
| Polysorbate | 0.58 | 0.23 | 0.68 |
| Phytoextract | 9.93 | 3.97 | 9.92 |
| Stabilizer | 0.12 | 0.05 | 0.14 |
| Buffer | 0.58 | 0.23 | 0.68 |
| Artificial sweetener | 1.15 | 0.46 | 1.35 |
| Linoleic acid | 0.50 | 0.20 | 0.59 |
| Farnesol | | | |
| Yellow # 5 | | | |
| TOTAL | 100.00 | 40.00 | 115.85 |

Example 20

In another embodiment, pharmaceutical film compositions were made with the following formulation:

|  | Formulation C | | |
| --- | --- | --- | --- |
| MATERIAL | WT % dry | WT % wet | mg/Strip |
| EPINEPHRINE bitartrate | 46.35 | 18.54 | 54.51 |
| Hydroxypropylmethyl cellulose | 11.53 | 4.61 | 13.55 |
| Polyvinyl pyrrolidone | 27.90 | 11.16 | 32.80 |
| Glycerol monooleate | 0.58 | 0.23 | 0.68 |
| Polyethylene oxide | 1.16 | 0.46 | 1.36 |
| Polysorbate | 0.58 | 0.23 | 0.68 |
| Phytoextract | 9.97 | 3.99 | 9.96 |
| Stabilizer | 0.12 | 0.05 | 0.14 |
| Buffer | 0.58 | 0.23 | 0.68 |
| Artificial sweetener | 1.16 | 0.46 | 1.36 |
| Linoleic acid | | | |
| Farnesol | 0.10 | 0.04 | 0.06 |
| Yellow # 5 | | | |
| TOTAL | 100.00 | 40.00 | 115.78 |

Example 21

In another embodiment, pharmaceutical film compositions were made with the following formulation:

|  | Formulation D | | |
| --- | --- | --- | --- |
| MATERIAL | WT % dry | WT % wet | mg/Strip |
| EPINEPHRINE bitartrate | 46.07 | 18.43 | 54.52 |
| Hydroxypropylmethyl cellulose | 11.46 | 4.58 | 13.56 |
| Polyvinyl pyrrolidone | 27.73 | 11.09 | 32.81 |
| Glycerol monooleate | 0.57 | 0.23 | 0.68 |
| Polyethylene oxide | 1.15 | 0.46 | 1.36 |
| Polysorbate | 0.57 | 0.23 | 0.68 |
| Phytoextract | 9.91 | 3.96 | 9.96 |
| Stabilizer | 0.11 | 0.05 | 0.14 |
| Buffer | 0.57 | 0.23 | 0.68 |
| Artificial sweetener | 1.15 | 0.46 | 1.36 |
| Linoleic acid | 0.10 | 0.04 | 0.06 |
| Farnesol | 0.50 | 0.20 | 0.29 |
| Yellow # 5 | 0.10 | 0.04 | 0.06 |
| TOTAL | 100.00 | 40.00 | 116.16 |

Example 22

Figure 19:
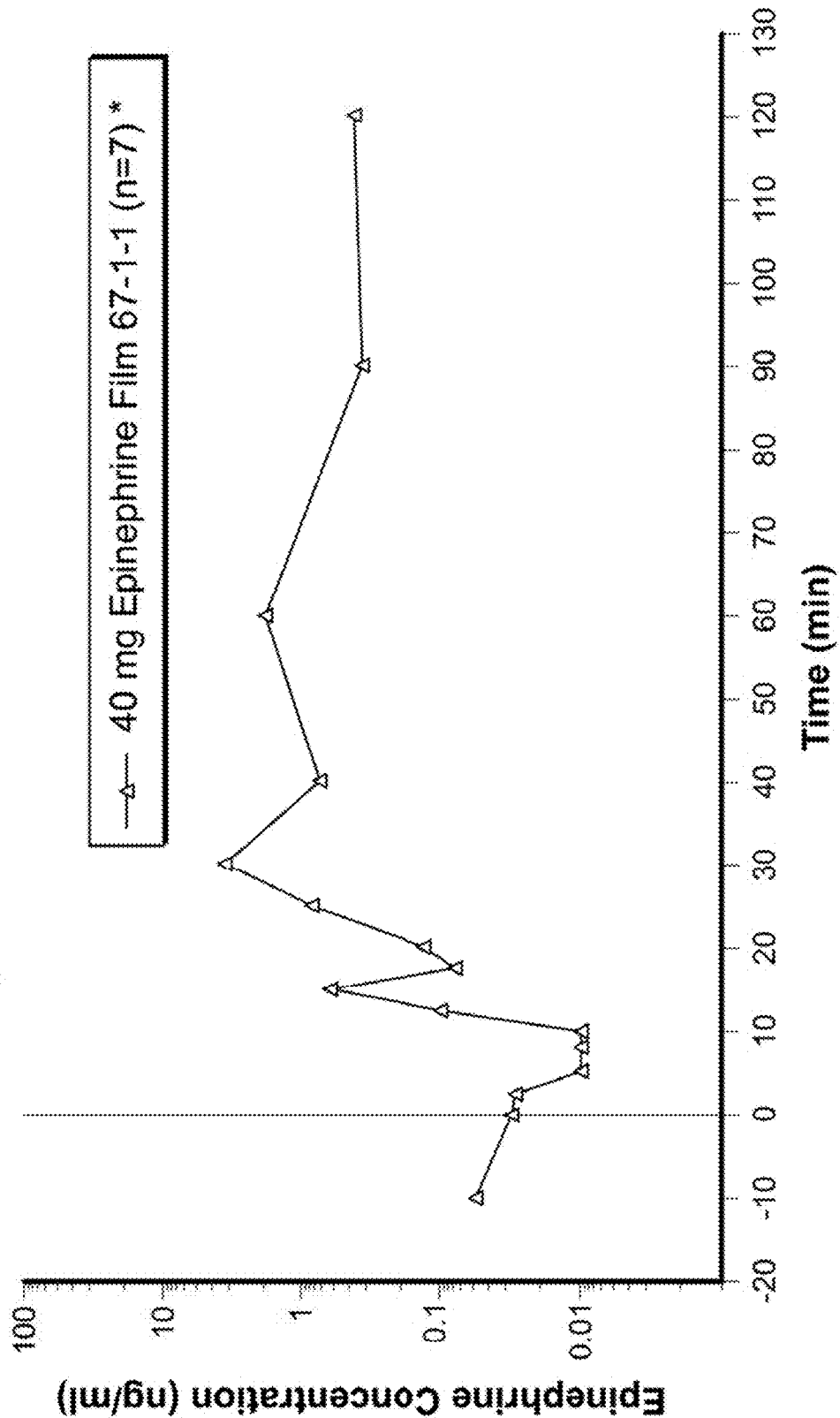
Referring to FIG. 19, this graph shows the impact of Enhancer A (Labrasol) in combination with Enhancer L (clove oil) on the concentration profiles of a 40 mg Epinephrine film (also shown in FIG. 20), in logarithmic view.

Referring to FIG. 19, this graph shows a pharmacokinetic model (logarithmic scale) in the male miniature swine studied to determine the impact of an enhancer (6% clove oil and 6% Labrasol) on epinephrine plasma concentration over time following sublingual or intramuscular administration. The epinephrine plasma concentration (in ng/mL) is shown as a function of time (in minutes) following sublingual or intramuscular administration of a farnesol permeation enhancer in Epinephrine films. The data shows the Epinephrine films film having enhanced stability of epinephrine concentration starting at just after the 10 minute time point through about 30 minutes, and until approximately 100 minutes.

Figure 20:
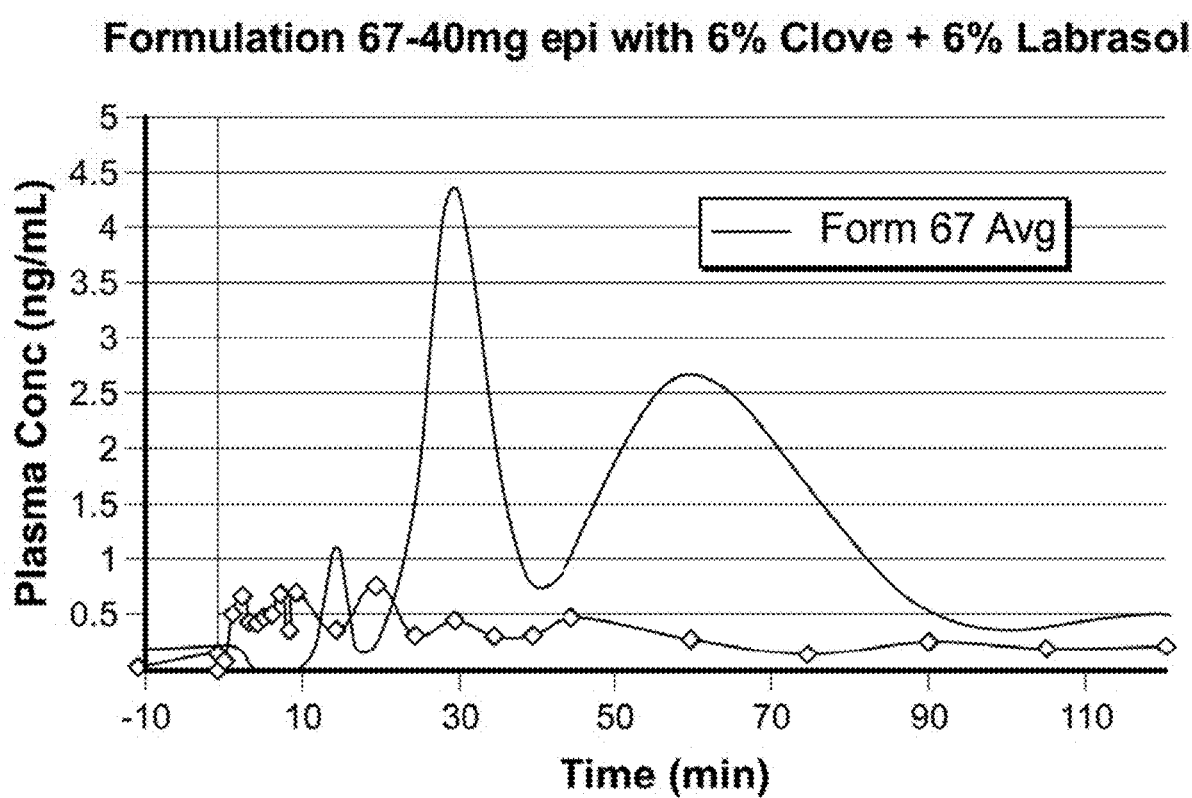
Referring to FIG. 20, this graph shows the impact of Enhancer A (Labrasol) in combination with Enhancer L (clove oil) on the concentration profiles of a 40 mg Epinephrine film vs. the average data collected from 0.3 mg Epipens.

Referring to FIG. 20, this graph shows a pharmacokinetic model of the Epinephrine film formulation in the male miniature swine as referenced in FIG. 19 compared against the average data collected from a 0.3 mg Epipen (indicated in diamond data points). As the data indicates, the average plasma concentration for the 0.3 mg Epipen peaked between 0.5 and 1 ng/mL. By contrast, the Epinephrine film formulation peaked between 4 and 4.5 ng/mL.

Example 23

Figure 21:
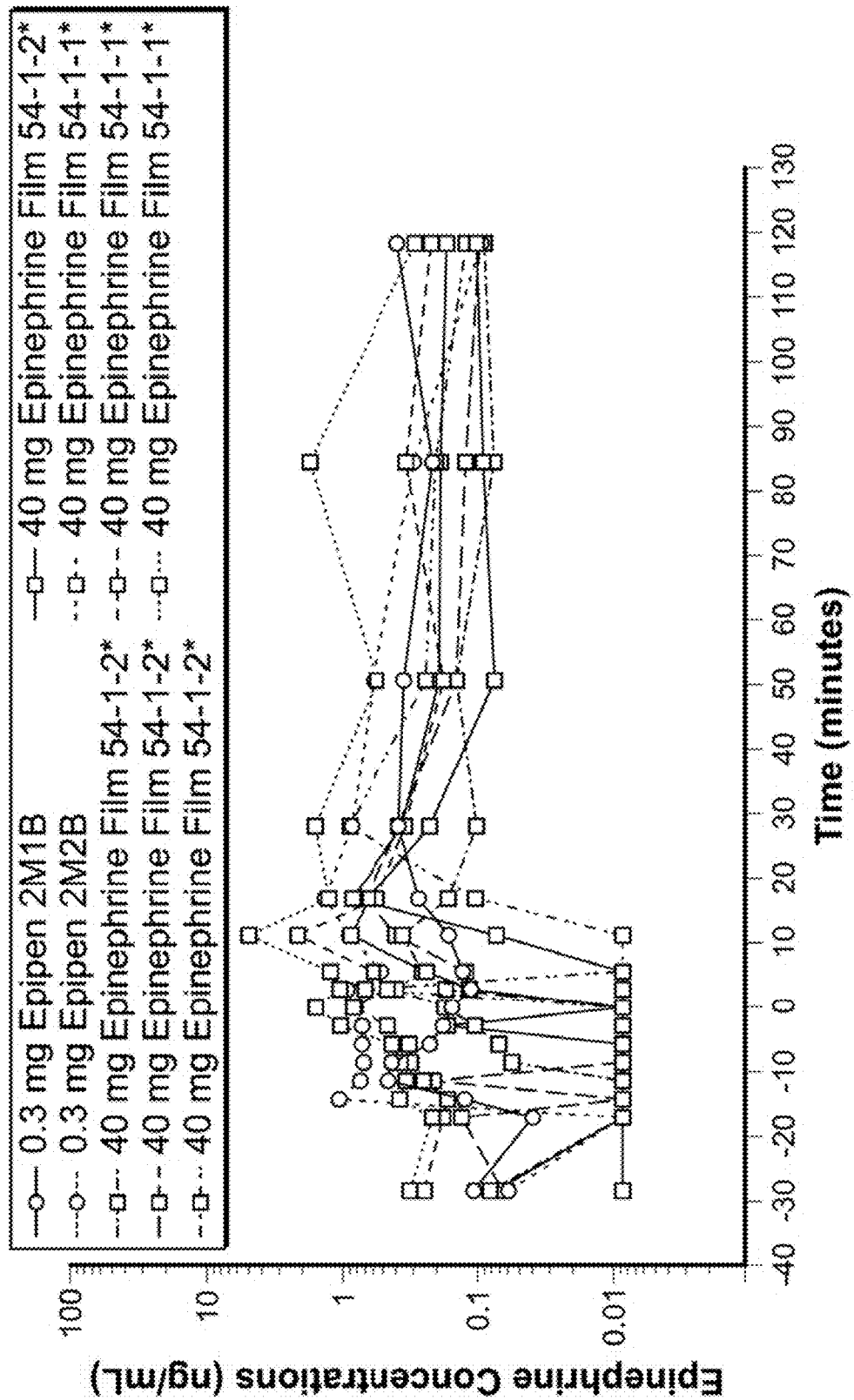
Referring to FIG. 21, this graph shows the impact of Enhancer A (Labrasol) in combination with Enhancer L (clove oil) on the concentration profiles of a 40 mg Epinephrine films, shown as separate animal subjects.

Referring to FIG. 21, this graph shows a pharmacokinetic model in the male miniature swine studied to determine the impact of an enhancer (9% clove+3% Labrasol) on epinephrine concentration over time following sublingual or intramuscular administration across 7 animal models. The general peak concentration was achieved between 10-30 minutes. All references cited herein are hereby incorporated by reference herein in their entirety.

Other embodiments are within the scope of the following claims.

What is claimed is:

1. A pharmaceutical composition, comprising:
   a polymeric matrix;
   pharmaceutically active component including epinephrine, or a pharmaceutically acceptable salt or ester thereof in the polymeric matrix; and
   an adrenergic receptor interacter.

2. The pharmaceutical composition of claim 1, wherein the pharmaceutically active component includes an ester of epinephrine.

3. The pharmaceutical composition of claim 1, wherein the polymeric matrix includes a mucoadhesive polymeric matrix.

4. The pharmaceutical composition of claim 1, wherein the adrenergic receptor interacter includes farnesol.

5. The pharmaceutical composition of claim 1, wherein the adrenergic receptor interacter includes linoleic acid.

6. The pharmaceutical composition of claim 1, wherein the adrenergic receptor interacter includes eugenol or eugenol acetate.

7. The pharmaceutical composition of claim 1, wherein the adrenergic receptor interacter includes a cinnamic acid, cinnamic acid ester, cinnamic aldehyde, or hydrocinnamic acid.

8. The pharmaceutical composition of claim 1, wherein the adrenergic receptor interacter includes chavicol.

9. The pharmaceutical composition of claim 1, wherein the adrenergic receptor interacter includes safrole.

10. The pharmaceutical composition of claim 1, wherein the adrenergic receptor interacter includes a phytoextract.

11. The pharmaceutical composition of claim 10, wherein the phytoextract includes an essential oil extract of a clove plant.

12. The pharmaceutical composition of claim 10, wherein the phytoextract includes an essential oil extract of a leaf of a clove plant.

13. The pharmaceutical composition of claim 10, wherein the phytoextract includes an essential oil extract of a flower bud of a clove plant.

14. The pharmaceutical composition of claim 10, wherein the phytoextract includes an essential oil extract of a stem of a clove plant.

15. The pharmaceutical composition of claim 10, wherein the phytoextract is synthetic or biosynthetic.

16. The pharmaceutical composition of claim 10, wherein the phytoextract includes 40-95% eugenol.

17. The pharmaceutical composition of claim 1, wherein the adrenergic receptor interacter includes a terpene, terpenoid, or a sesquiterpene.

18. The pharmaceutical composition of claim 1, wherein the pharmaceutical composition is a chewable or gelatin based dosage form, spray, gum, gel, cream, tablet, liquid, or film.

19. The pharmaceutical composition of claim 1, wherein the polymeric matrix includes a water soluble polymer.

20. The pharmaceutical composition of claim 1, wherein the polymeric matrix includes a polyethylene oxide.

21. The pharmaceutical composition of claim 1, wherein the polymeric matrix includes a cellulosic polymer selected from the group of: hydroxypropylmethyl cellulose, hydroxyethyl cellulose, hydroxyethylmethyl cellulose, hydroxypropyl cellulose, methylcellulose, and carboxymethyl cellulose.

22. The pharmaceutical composition of claim 1, wherein the polymeric matrix comprises a cellulosic polymer, polyethylene oxide and polyvinyl pyrrolidone, polyethylene oxide and a polysaccharide, polyethylene oxide, hydroxypropyl methylcellulose and a polysaccharide, or polyethylene oxide, hydroxypropyl methylcellulose, polysaccharide, and polyvinylpyrrolidone.

23. The pharmaceutical composition of claim 1, wherein the polymeric matrix comprises at least one polymer selected from the group of: pullulan, polyvinyl pyrrolidone, polyvinyl alcohol, sodium alginate, polyethylene glycol, xanthan gum, tragancanth gum, guar gum, acacia gum, arabic gum, polyacrylic acid, methylmethacrylate copolymer, carboxyvinyl copolymers, starch, pregelatinized starch, hydrogenated starch hydrolysate, water-soluble chemical derivatives of starch, gelatin, ethylene oxide-propylene oxide copolymers, collagen, albumin, poly-amino acids, polyphosphazenes, polysaccharides, chitin, and chitosan.

24. The pharmaceutical composition of claim 1, further comprising a stabilizer.

25. The pharmaceutical composition of claim 1, wherein the polymeric matrix comprises a dendritic polymer or a hyperbranched polymer.

26. The pharmaceutical composition of claim 1, wherein the adrenergic receptor interacter and the pharmaceutically active component are contained in discrete layers of a film.

27. The pharmaceutical composition of claim 1, further comprising sodium citrate, citric acid, or a combination thereof.

28. The pharmaceutical composition of claim 1, further comprising one or more of sodium citrate, citric acid, sodium metabisulfite, sodium bisulfite, glycerol, glycerol monoacetate, glycerol diacetate, glycerol triacetate, polysorbate, cetyl alcohol, propylene glycol sorbitan monostearate, sorbitan monooleate, sorbitan monopalmitate, sucralose, sorbitol, mannitol, or xylitol, or combinations thereof.

29. The pharmaceutical composition of claim 1, wherein the adrenergic receptor interacter is a compound that modifies and/or otherwise alters the action of an adrenergic receptor.

30. The pharmaceutical composition of claim 1, wherein the adrenergic receptor interacter is an adrenergic receptor blocker.

31. The pharmaceutical composition of claim 1, wherein the adrenergic receptor interacter is an a C3-C22 ester.

32. A method of making a pharmaceutical composition comprising:
    combining an adrenergic receptor interacter with a pharmaceutically active component including epinephrine, and
    forming a pharmaceutical composition including the adrenergic receptor interacter and the pharmaceutically active component, wherein the pharmaceutically active component being contained in a polymeric matrix.

33. A device comprising
a housing that holds an amount of a pharmaceutical composition of claim 1 and
an opening that dispenses a predetermined amount of the pharmaceutical composition.

\* \* \* \* \*